United States Patent
Ibrahim et al.

(10) Patent No.: US 10,494,657 B2
(45) Date of Patent: Dec. 3, 2019

(54) IN VITRO PRODUCTION OF CYCLIC PEPTIDES

(71) Applicants: The University Court of the University of Aberdeen, Aberdeen (GB); The University Court of the University of St. Andrews, St. Andrews (GB)

(72) Inventors: Wael Houssen Ibrahim, Aberdeen (GB); Marcel Jaspars, Aberdeen (GB); Margaret Smith, Aberdeen (GB); James Naismith, St. Andrews (GB); Jesko Koehnke, St. Andrews (GB); Andrew Bent, St. Andrews (GB); Nicholas Westwood, St. Andrews (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 15/683,266

(22) Filed: Aug. 22, 2017

(65) Prior Publication Data

US 2018/0179570 A1    Jun. 28, 2018

Related U.S. Application Data

(63) Continuation of application No. 14/410,939, filed as application No. PCT/GB2013/051735 on Jun. 28, 2013.

(30) Foreign Application Priority Data

Jun. 29, 2012    (GB) .................................. 1211617.4

(51) Int. Cl.
| | |
|---|---|
| A61K 38/08 | (2019.01) |
| C12P 21/00 | (2006.01) |
| G01N 33/68 | (2006.01) |
| C12Q 1/527 | (2006.01) |
| C07K 7/64 | (2006.01) |

(52) U.S. Cl.
CPC ............... *C12P 21/00* (2013.01); *C07K 7/64* (2013.01); *C12Q 1/527* (2013.01); *G01N 33/6818* (2013.01)

(58) Field of Classification Search
None
See application file for complete search history.

(56) References Cited

U.S. PATENT DOCUMENTS

| | | |
|---|---|---|
| 2003/0181381 A1 | 9/2003 | Himmelspach et al. |
| 2010/0209414 A1 | 8/2010 | Schmidt et al. |
| 2015/0322474 A1 | 11/2015 | Houssen Ibrahim et al. |

FOREIGN PATENT DOCUMENTS

| | | |
|---|---|---|
| WO | WO-2001/04146 A2 | 1/2001 |
| WO | WO-2007/103739 A2 | 9/2007 |

OTHER PUBLICATIONS

Lee, J. Am. Chem. Soc. 2009, 131, 2122-2124 (Year: 2009).*
McIntosh, J. Am. Chem. Soc., 2010, 132, 15499-15501 (Year: 2010).*
Donia et al. (2008) "A Global Assembly Line for Cyanobactins," *Nature Chemical Biology*, 4:341-343.
Lee et al. (2009) "Using Marine Natural Products to Discover a Protease that Catalyzes Peptide Macrocyclization of Diverse Substrates," *Journal of the American Chemical Society*, 131: 2122-2124.
McIntosh et al. (2010) "Circular Logic: Nonribosomal Peptide-like Macrocyclization with a Ribosomal Peptide Catalyst," *Journal of the American Chemical Society*, 132:15499-15501.
McIntosh et al. (2010) "Marine Molecular Machines: Heterocyclization in Cyanobactin Biosynthesis," ChemBioChem, 11:1413-1421.
Lee et al. (2009) Supporting Online Material for "Using Marine Natural Products to Discover a Protease that Catalyzes Peptide Macrocyclization of Diverse Substrates," *Journal of the American Chemical Society*, 131: 2122-2124 (S1-S9).
McIntosh et al. (2010) Supporting Online Material for "Circular Logic: Nonribosomal Peptide-like Macrocyclization with a Ribosomal Peptide Catalyst," *Journal of the American Chemical Society*, 132:15499-15501 (4 pages).

* cited by examiner

*Primary Examiner* — Satyanarayana R Gudibande
(74) *Attorney, Agent, or Firm* — Goodwin Procter LLP

(57) ABSTRACT

This invention relates to the in vitro production of cyclic peptides using cyanobacterial enzymes, such as patellamide biosynthesis enzymes. Linear peptide substrates are cyclized using an isolated cyanbacterial macrocyclase, such as PatG from *Prochloron* spp. Before cyclization, residues in the linear peptide substrates may be heterocyclized using isolated cyanbacterial heterocyclasses, such as PatD or TruD heterocyclase. Methods of the invention may be useful, for example, for the production of cyclic peptidyl molecules, including cyclotides, such as katalas, and cyanobactins, such as patellamides and telomestatins, for example for use in the development of therapeutics.

21 Claims, 31 Drawing Sheets

Specification includes a Sequence Listing.

SEQUENCE LISTING

<160> NUMBER OF SEQ ID NOS: 106

<210> SEQ ID NO 1
<211> LENGTH: 1191
<212> TYPE: PRT
<213> ORGANISM: Prochloron didemni

<400> SEQUENCE: 1

Met Phe Ser Ile Met Ile Thr Ile Asp Tyr Pro Phe Thr Val Ser Leu
1               5                   10                  15

Asn Arg Asp Ile Gln Val Thr Ser Thr Glu Asp Tyr Tyr Thr Leu Gln
            20                  25                  30

Val Thr Glu Ser Asp Pro Ser Ala Trp Leu Thr Phe Ala Thr Thr Pro
        35                  40                  45

Ala Met Asp Met Ala Phe Asp His Leu Lys Ala Gly Thr Thr Thr Glu
    50                  55                  60

Ser Leu Val Gln Thr Leu Ala Glu Leu Gly Gly Pro Ala Ala Arg Glu
65                  70                  75                  80

Gln Phe Ala Leu Thr Leu Gln Gln Leu Asp Glu Arg Gly Trp Leu Ser
                85                  90                  95

Tyr Ala Val Leu Pro Leu Ala Glu Ala Ile Pro Met Val Glu Ser Ala
            100                 105                 110

Glu Leu Asn Leu Pro Gly Asn Pro His Trp Met Glu Thr Gly Val Thr
        115                 120                 125

Leu Ser Arg Phe Ala Tyr Gln His Pro Tyr Glu Gly Thr Met Val Leu
130                 135                 140

Glu Ser Pro Leu Ser Lys Phe Arg Val Lys Leu Leu Asp Trp Arg Ala
145                 150                 155                 160

Ser Ala Leu Leu Ala Gln Leu Ala Gln Pro Gln Thr Leu Gly Thr Ile
                165                 170                 175

Ala Pro Pro Pro Tyr Leu Gly Pro Glu Thr Ala Tyr Gln Phe Leu Asn
            180                 185                 190

Leu Leu Trp Ala Thr Gly Phe Leu Ala Ser Asp His Glu Pro Val Ser
        195                 200                 205

Leu Gln Leu Trp Asp Phe His Asn Leu Leu Phe His Ser Arg Ser Arg
210                 215                 220

Leu Gly Arg His Asp Tyr Pro Gly Thr Asp Leu Asn Val Asp Asn Trp
225                 230                 235                 240

Ser Asp Phe Pro Val Val Lys Pro Pro Met Ser Asp Arg Ile Val Pro
                245                 250                 255

Leu Pro Arg Pro Asn Leu Glu Ala Leu Met Ser Asn Asp Ala Thr Leu
            260                 265                 270

Thr Glu Ala Ile Glu Thr Arg Lys Ser Val Arg Glu Tyr Asp Asp Asp
        275                 280                 285

Asn Pro Ile Thr Ile Glu Gln Leu Gly Glu Leu Tyr Arg Ala Ala
        290                 295                 300

Arg Val Thr Lys Leu Leu Ser Pro Glu Glu Arg Phe Gly Lys Leu Trp
305                 310                 315                 320

Gln Gln Asn Lys Pro Val Phe Glu Glu Ala Gly Val Asp Glu Gly Glu
                325                 330                 335

Phe Ser His Arg Pro Tyr Pro Gly Gly Ala Met Tyr Glu Leu Glu
            340                 345                 350

Ile Tyr Pro Val Val Arg Leu Cys Gln Gly Leu Ser Gln Gly Val Tyr
        355                 360                 365

```
His Tyr Asp Pro Leu Asn His Gln Leu Glu Gln Ile Val Glu Ser Lys
    370                 375                 380

Asp Asp Ile Phe Ala Val Ser Gly Ser Pro Leu Ala Ser Lys Leu Gly
385                 390                 395                 400

Pro His Val Leu Leu Val Ile Thr Ala Arg Phe Gly Arg Leu Phe Arg
                405                 410                 415

Leu Tyr Arg Ser Val Ala Tyr Ala Leu Val Leu Lys His Val Gly Val
            420                 425                 430

Leu Gln Gln Asn Leu Tyr Leu Val Ala Thr Asn Met Gly Leu Ala Pro
        435                 440                 445

Cys Ala Gly Gly Ala Gly Asp Ser Asp Ala Phe Ala Gln Val Thr Gly
450                 455                 460

Ile Asp Tyr Val Glu Glu Ser Ala Val Gly Glu Phe Ile Leu Gly Ser
465                 470                 475                 480

Leu Ala Ser Glu Val Glu Ser Asp Val Glu Gly Glu Asp Glu Ile
                485                 490                 495

Glu Ser Ala Gly Val Ser Ala Ser Glu Val Glu Ser Ser Ala Thr Lys
                500                 505                 510

Gln Lys Val Ala Leu His Pro His Asp Leu Asp Glu Arg Ile Pro Gly
            515                 520                 525

Leu Ala Asp Leu His Asn Gln Thr Leu Gly Asp Pro Gln Ile Thr Ile
        530                 535                 540

Val Ile Ile Asp Gly Asp Pro Asp Tyr Thr Leu Ser Cys Phe Glu Gly
545                 550                 555                 560

Ala Glu Val Ser Lys Val Phe Pro Tyr Trp His Glu Pro Ala Glu Pro
                565                 570                 575

Ile Thr Pro Glu Asp Tyr Ala Ala Phe Gln Ser Ile Arg Asp Gln Gly
            580                 585                 590

Leu Lys Gly Lys Glu Lys Glu Ala Leu Glu Ala Val Ile Pro Asp
        595                 600                 605

Thr Lys Asp Arg Ile Val Leu Asn Asp His Ala Cys His Val Thr Ser
    610                 615                 620

Thr Ile Val Gly Gln Glu His Ser Pro Val Phe Gly Ile Ala Pro Asn
625                 630                 635                 640

Cys Arg Val Ile Asn Met Pro Gln Asp Ala Val Ile Arg Gly Asn Tyr
                645                 650                 655

Asp Asp Val Met Ser Pro Leu Asn Leu Ala Arg Ala Ile Asp Leu Ala
            660                 665                 670

Leu Glu Leu Gly Ala Asn Ile Ile His Cys Ala Phe Cys Arg Pro Thr
        675                 680                 685

Gln Thr Ser Glu Gly Glu Glu Ile Leu Val Gln Ala Ile Lys Lys Cys
    690                 695                 700

Gln Asp Asn Asn Val Leu Ile Val Ser Pro Thr Gly Asn Asn Ser Asn
705                 710                 715                 720

Glu Ser Trp Cys Leu Pro Ala Val Leu Pro Gly Thr Leu Ala Val Gly
                725                 730                 735

Ala Ala Lys Val Asp Gly Thr Pro Cys His Phe Ser Asn Trp Gly Gly
            740                 745                 750

Asn Asn Thr Lys Glu Gly Ile Leu Ala Pro Gly Glu Gly Ile Leu Gly
        755                 760                 765

Ala Gln Pro Cys Thr Glu Glu Pro Val Arg Leu Thr Gly Thr Ser Met
    770                 775                 780

Ala Ala Pro Val Met Thr Gly Ile Ser Ala Leu Leu Met Ser Leu Gln
```

-continued

```
            785                 790                 795                 800
    Val Gln Gln Gly Lys Pro Val Asp Ala Glu Ala Val Arg Thr Ala Leu
                        805                 810                 815

Leu Lys Thr Ala Ile Pro Cys Asp Pro Glu Val Val Glu Pro Glu
                    820                  825                 830

Arg Cys Leu Arg Gly Phe Val Asn Ile Pro Gly Ala Met Lys Val Leu
                    835                  840                 845

Phe Gly Gln Pro Ser Val Thr Val Ser Phe Ala Gly Gly Gln Ala Thr
                    850                  855                 860

Arg Thr Glu His Pro Gly Tyr Ala Thr Val Ala Pro Ala Ser Ile Pro
    865                 870                 875                 880

Glu Pro Met Ala Glu Arg Ala Thr Pro Ala Val Gln Ala Ala Thr Ala
                        885                 890                 895

Thr Glu Met Val Ile Ala Pro Ser Thr Glu Pro Ala Asn Pro Ala Thr
                        900                 905                 910

Val Glu Ala Ser Thr Ala Phe Ser Gly Asn Val Tyr Ala Leu Gly Thr
                        915                 920                 925

Ile Gly Tyr Asp Phe Gly Asp Glu Ala Arg Arg Asp Thr Phe Lys Glu
                    930                  935                 940

Arg Met Ala Asp Pro Tyr Asp Ala Arg Gln Met Val Asp Tyr Leu Asp
    945                 950                 955                 960

Arg Asn Pro Asp Glu Ala Arg Ser Leu Ile Trp Thr Leu Asn Leu Glu
                    965                  970                 975

Gly Asp Val Ile Tyr Ala Leu Asp Pro Lys Gly Pro Phe Ala Thr Asn
                    980                  985                 990

Val Tyr Glu Ile Phe Leu Gln Met  Leu Ala Gly Gln Leu  Glu Pro Glu
                    995                 1000                1005

Thr Ser  Ala Asp Phe Ile Glu  Arg Leu Ser Val Pro  Ala Arg Arg
                1010                1015                1020

Thr Thr  Arg Thr Val Glu Leu  Phe Ser Gly Glu Val  Met Pro Val
                1025                1030                1035

Val Asn  Val Arg Asp Pro Arg  Gly Met Tyr Gly Trp  Asn Val Asn
                1040                1045                1050

Ala Leu  Val Asp Ala Ala Leu  Ala Thr Val Glu Tyr  Glu Glu Ala
                1055                1060                1065

Asp Glu  Asp Ser Leu Arg Gln  Gly Leu Thr Ala Phe  Leu Asn Arg
                1070                1075                1080

Val Tyr  His Asp Leu His Asn  Leu Gly Gln Thr Ser  Arg Asp Arg
                1085                1090                1095

Ala Leu  Asn Phe Thr Val Thr  Asn Thr Phe Gln Ala  Ala Ser Thr
                1100                1105                1110

Phe Ala  Gln Ala Ile Ala Ser  Gly Arg Gln Leu Asp  Thr Ile Glu
                1115                1120                1125

Val Asn  Lys Ser Pro Tyr Cys  Arg Leu Asn Ser Asp  Cys Trp Asp
                1130                1135                1140

Val Leu  Leu Thr Phe Tyr Asp  Pro Glu His Gly Arg  Arg Ser Arg
                1145                1150                1155

Arg Val  Phe Arg Phe Thr Leu  Asp Val Val Tyr Val  Leu Pro Val
                1160                1165                1170

Thr Val  Gly Ser Ile Lys Ser  Trp Ser Leu Pro Gly  Lys Gly Thr
                1175                1180                1185

Val Ser  Lys
                1190
```

<210> SEQ ID NO 2
<211> LENGTH: 702
<212> TYPE: PRT
<213> ORGANISM: Prochloron didemni

<400> SEQUENCE: 2

```
Met Asn Arg Asp Ile Leu Arg Thr Leu Ser Leu Lys Gly Asp His Asn
1               5                   10                  15

Ile Arg Val Ala Ile Leu Asp Gly Pro Val Asp Ile Ala His Pro Cys
            20                  25                  30

Phe Gln Gly Ala Asp Leu Thr Val Leu Pro Thr Leu Ala Pro Thr Ala
        35                  40                  45

Ala Arg Ser Asp Gly Phe Met Ser Ala His Gly Thr His Val Ala Ser
50                  55                  60

Ile Ile Phe Gly Gln Pro Glu Thr Ser Val Pro Gly Ile Ala Pro Gln
65                  70                  75                  80

Cys Arg Gly Leu Ile Val Pro Ile Phe Ser Asp Asp Arg Arg Arg Ile
                85                  90                  95

Thr Gln Leu Asp Leu Ala Arg Gly Ile Glu Arg Ala Val Asn Ala Gly
            100                 105                 110

Ala His Ile Ile Asn Ile Ser Gly Gly Glu Leu Thr Asp Phe Gly Glu
        115                 120                 125

Ala Asp Gly Trp Leu Glu Asn Ala Val Ser Leu Cys Arg Gln Asn Asn
130                 135                 140

Val Leu Leu Val Ala Ala Gly Asn Asn Gly Cys Asp Cys Leu His
145                 150                 155                 160

Val Pro Ala Ala Leu Pro Ala Val Leu Ala Val Gly Ala Met Asp Asp
                165                 170                 175

His Gly His Pro Leu Asp Phe Ser Asn Trp Gly Ser Thr Tyr Glu Gln
            180                 185                 190

Gln Gly Ile Leu Ala Pro Gly Glu Asp Ile Leu Gly Ala Lys Pro Gly
        195                 200                 205

Gly Gly Thr Glu Arg Leu Ser Gly Thr Ser Phe Ala Thr Pro Ile Val
210                 215                 220

Ser Gly Val Ala Ala Leu Leu Leu Ser Glu Gln Val Arg Arg Gly Glu
225                 230                 235                 240

Thr Pro Asp Pro Gln Lys Val Arg Gln Leu Leu Leu Gln Ser Ala Leu
                245                 250                 255

Pro Cys Asp Asp Asp Ala Pro Glu Gln Ala Arg Arg Cys Leu Ala Gly
            260                 265                 270

Arg Leu Asn Val Ser Gly Ala Phe Thr Leu Leu Lys Gly Gly Asn Met
        275                 280                 285

Ser Glu Glu Leu Ala Thr Ala Ser Phe Pro Ser Val Glu Ala Ser Cys
290                 295                 300

Gly Cys Asn Gly Gly Leu Val Ala Ala Glu Pro Thr Thr Asn Ser Gly
305                 310                 315                 320

Ser Met Pro Ala Leu Ser Val Ser Ser Phe Ala Gly Ala Ser Pro Ala
                325                 330                 335

Thr Met Glu Ala Ala Gly Pro Leu Asp Glu Pro Gln Pro Leu Pro Ser
            340                 345                 350

Pro Ala Gln Pro Leu Thr Gln Met Pro Ala Gln Pro Leu Pro Ser Pro
        355                 360                 365

Ala Gln Pro Leu Thr Gln Met Pro Ala Gln Pro Leu Pro Phe Pro Ala
```

```
            370                 375                 380
Gln Pro Leu Thr Gln Met Pro Ala Gln Pro Leu Thr Gln Met Pro Ala
385                 390                 395                 400

Pro Thr Gln Thr Leu Ser Met Thr Thr Asn Gln Val Thr Pro Ser Gln
                405                 410                 415

Ala Pro Ser Glu Leu Ala Asn Ser Gln Phe Ala Tyr Val Leu Gly Thr
            420                 425                 430

Leu Gly Tyr Asp Phe Gly Thr Glu Ala Arg Arg Asp Thr Phe Lys Gln
        435                 440                 445

Leu Met Pro Pro Phe Asp Phe Ala Gly Asn Met Val Pro Ala Asn Pro
    450                 455                 460

Tyr Asp Ala Arg Gln Met Val Asp Tyr Leu Gly Asn Asn Ile Ser Glu
465                 470                 475                 480

Ala Arg Ser Leu Ile Trp Thr Val Asn Ile Glu Leu Thr Pro Val Tyr
                485                 490                 495

Ala Ile Asp Pro Thr Gly Pro Phe Ala Ser Ser Thr Tyr His Ala Leu
            500                 505                 510

Gln Glu Leu Leu Ser Gly Gln Ile Gln Ala Glu Asp Asn Glu Glu Tyr
        515                 520                 525

Val Glu Arg Val Ser Ile Pro Gly Val Leu Thr Asn Arg Ser Val Lys
    530                 535                 540

Leu Phe Ser Gly Gln Val Val Pro Val Val Glu Pro Gln Ser Thr Arg
545                 550                 555                 560

Gly Leu Tyr Gly Trp Lys Val Asn Gly Leu Val Asn Ala Ala Leu Glu
                565                 570                 575

Ala Val Arg Ala Glu Gly Gly Asp Ala Gly Glu Ala Arg Ile Arg Gln
            580                 585                 590

Thr Leu Asp Gly Phe Leu Asn Arg Ile Tyr Tyr Asp Leu Arg Asn Leu
        595                 600                 605

Gly Thr Thr Ser Gln Asp Arg Ala Leu Asn Phe Ala Val Thr Asn Ala
    610                 615                 620

Phe Gln Ala Ala Gln Thr Phe Ser Gln Ser Val Ala Ala Gly Met Glu
625                 630                 635                 640

Leu Asp Ser Val Thr Val Glu Lys Ser Pro Phe Cys Arg Leu Asp Ser
                645                 650                 655

Asp Cys Trp Asp Ile Lys Leu Lys Phe Phe Asp Pro Glu Asn Asn Arg
            660                 665                 670

Arg Ala Lys Lys Ile Tyr Arg Phe Thr Ile Asp Val Ser Asp Leu Val
        675                 680                 685

Pro Val Thr Met Gly Glu Val Arg Ser Trp Ser Ser Ser Tyr
    690                 695                 700

<210> SEQ ID NO 3
<211> LENGTH: 784
<212> TYPE: PRT
<213> ORGANISM: Prochloron didemni

<400> SEQUENCE: 3

Met Gln Pro Thr Ala Leu Gln Ile Lys Pro His Phe His Val Glu Ile
1               5                   10                  15

Ile Glu Pro Lys Gln Val Tyr Leu Leu Gly Glu Gln Gly Asn His Ala
            20                  25                  30

Leu Thr Gly Gln Leu Tyr Cys Gln Ile Leu Pro Phe Leu Asn Gly Glu
        35                  40                  45
```

-continued

```
Tyr Thr Arg Glu Gln Ile Val Glu Lys Leu Asp Gly Gln Val Pro Glu
 50                  55                  60
Glu Tyr Ile Asp Phe Val Leu Ser Arg Leu Val Glu Lys Gly Tyr Leu
 65                  70                  75                  80
Thr Glu Val Ala Pro Glu Leu Ser Leu Glu Val Ala Ala Phe Trp Ser
                 85                  90                  95
Glu Leu Gly Ile Ala Pro Ser Val Val Ala Glu Gly Leu Lys Gln Pro
                100                 105                 110
Val Thr Val Thr Thr Ala Gly Lys Gly Ile Arg Glu Gly Ile Val Ala
                115                 120                 125
Asn Leu Ala Ala Ala Leu Glu Glu Ala Gly Ile Gln Val Ser Asp Pro
130                 135                 140
Lys Ala Pro Lys Ala Pro Lys Ala Gly Asp Ser Thr Ala Gln Leu Gln
145                 150                 155                 160
Val Val Leu Thr Asp Asp Tyr Leu Gln Pro Glu Leu Ala Ala Ile Asn
                165                 170                 175
Lys Glu Ala Leu Glu Arg Gln Gln Pro Trp Leu Leu Val Lys Pro Val
                180                 185                 190
Gly Ser Ile Leu Trp Leu Gly Pro Leu Phe Val Pro Gly Glu Thr Gly
                195                 200                 205
Cys Trp His Cys Leu Ala Gln Arg Leu Arg Gly Asn Arg Glu Val Glu
                210                 215                 220
Ala Ser Val Leu Gln Gln Lys Arg Ala Leu Gln Glu Arg Asn Gly Gln
225                 230                 235                 240
Asn Lys Asn Gly Ala Val Ser Cys Leu Pro Thr Ala Arg Ala Thr Leu
                245                 250                 255
Pro Ser Thr Leu Gln Thr Gly Leu Gln Trp Ala Ala Thr Glu Ile Ala
                260                 265                 270
Lys Trp Met Val Lys Arg His Leu Asn Ala Ile Ala Pro Gly Thr Ala
                275                 280                 285
Arg Phe Pro Thr Leu Ala Gly Lys Ile Phe Thr Phe Asn Gln Thr Thr
                290                 295                 300
Leu Glu Leu Lys Ala His Pro Leu Ser Arg Arg Pro Gln Cys Pro Thr
305                 310                 315                 320
Cys Gly Asp Gln Glu Ile Leu Gln Arg Arg Gly Phe Glu Pro Leu Lys
                325                 330                 335
Leu Glu Ser Arg Pro Lys His Phe Thr Ser Asp Gly Gly His Arg Ala
                340                 345                 350
Thr Thr Pro Glu Gln Thr Val Gln Lys Tyr Gln His Leu Ile Gly Pro
                355                 360                 365
Ile Thr Gly Val Val Thr Glu Leu Val Arg Ile Ser Asp Pro Ala Asn
370                 375                 380
Pro Leu Val His Thr Tyr Arg Ala Gly His Ser Phe Gly Ser Ser Ala
385                 390                 395                 400
Gly Ser Leu Arg Gly Leu Arg Asn Thr Leu Arg Tyr Lys Ser Ser Gly
                405                 410                 415
Lys Gly Lys Thr Asp Ser Gln Ser Arg Ala Ser Gly Leu Cys Glu Ala
                420                 425                 430
Ile Glu Arg Tyr Ser Gly Ile Phe Leu Gly Asp Glu Pro Arg Lys Arg
                435                 440                 445
Ala Thr Leu Ala Glu Leu Gly Asp Leu Ala Ile His Pro Glu Gln Cys
450                 455                 460
Leu His Phe Ser Asp Arg Gln Tyr Asp Asn Arg Asp Ala Leu Asn Ala
```

-continued

Glu Gly Ser Ala Ala Tyr Arg Trp Ile Pro His Arg Phe Ala Ala
465                 470                 475                 480
            485                 490                 495

Ser Gln Ala Ile Asp Trp Thr Pro Leu Trp Ser Leu Thr Glu Gln Lys
            500                 505                 510

His Lys Tyr Val Pro Thr Ala Ile Cys Tyr Tyr Asn Tyr Leu Leu Pro
            515                 520                 525

Pro Ala Asp Arg Phe Cys Lys Ala Asp Ser Asn Gly Asn Ala Ala Gly
        530                 535                 540

Asn Ser Leu Glu Glu Ala Ile Leu Gln Gly Phe Met Glu Leu Val Glu
545                 550                 555                 560

Arg Asp Ser Val Ala Leu Trp Trp Tyr Asn Arg Leu Arg Arg Pro Glu
                565                 570                 575

Val Glu Leu Ser Ser Phe Glu Glu Pro Tyr Phe Leu Gln Leu Gln Gln
            580                 585                 590

Phe Tyr Arg Ser Gln Asn Arg Glu Leu Trp Val Leu Asp Leu Thr Ala
        595                 600                 605

Asp Leu Gly Ile Pro Ala Phe Ala Gly Leu Ser Arg Arg Thr Val Gly
610                 615                 620

Ser Ser Glu Arg Val Ser Ile Gly Phe Gly Ala His Leu Asp Pro Lys
625                 630                 635                 640

Ile Ala Ile Leu Arg Ala Leu Thr Glu Val Ser Gln Val Gly Leu Glu
                645                 650                 655

Leu Asp Lys Val Pro Asp Glu Lys Leu Asp Gly Glu Ser Lys Asp Trp
            660                 665                 670

Met Leu Glu Val Thr Leu Glu Thr His Pro Cys Leu Ala Pro Asp Pro
        675                 680                 685

Ser Gln Pro Arg Lys Thr Ala Asn Asp Tyr Pro Lys Arg Trp Ser Asp
        690                 695                 700

Asp Ile Tyr Thr Asp Val Met Ala Cys Val Glu Met Ala Lys Val Ala
705                 710                 715                 720

Gly Leu Glu Thr Leu Val Leu Asp Gln Thr Arg Pro Asp Ile Gly Leu
                725                 730                 735

Asn Val Val Lys Val Met Ile Pro Gly Met Arg Thr Phe Trp Ser Arg
            740                 745                 750

Tyr Gly Pro Gly Arg Leu Tyr Asp Val Pro Val Gln Leu Gly Trp Leu
        755                 760                 765

Lys Glu Pro Leu Ala Glu Ala Glu Met Asn Pro Thr Asn Ile Pro Phe
        770                 775                 780

<210> SEQ ID NO 4
<211> LENGTH: 781
<212> TYPE: PRT
<213> ORGANISM: Prochloron didemni

<400> SEQUENCE: 4

Met Gln Pro Thr Ala Leu Gln Ile Lys Pro His Phe His Val Glu Ile
1               5                   10                  15

Ile Glu Pro Lys Gln Val Tyr Leu Leu Gly Glu Gln Gly Asn His Ala
            20                  25                  30

Leu Thr Gly Gln Leu Tyr Cys Gln Ile Leu Pro Phe Leu Asn Gly Glu
        35                  40                  45

Tyr Thr Arg Glu Gln Ile Val Glu Lys Leu Asp Gly Gln Val Pro Glu
    50                  55                  60

```
Glu Tyr Ile Asp Phe Val Leu Ser Arg Leu Val Lys Gly Tyr Leu
 65                  70                  75                  80

Thr Glu Val Ala Pro Glu Leu Ser Leu Glu Val Ala Ala Phe Trp Ser
                 85                  90                  95

Glu Leu Gly Ile Ala Pro Ser Val Val Ala Glu Gly Leu Lys Gln Pro
                100                 105                 110

Val Thr Val Thr Thr Ala Gly Lys Gly Ile Arg Glu Gly Ile Val Ala
                115                 120                 125

Asn Leu Ala Ala Ala Leu Glu Ala Gly Ile Gln Val Ser Asp Pro
130                 135                 140

Arg Asp Pro Lys Ala Pro Lys Ala Gly Asp Ser Thr Ala Gln Leu Gln
145                 150                 155                 160

Val Val Leu Thr Asp Asp Tyr Leu Gln Pro Glu Leu Ala Ala Ile Asn
                165                 170                 175

Lys Glu Ala Leu Glu Arg Gln Gln Pro Trp Leu Leu Val Lys Pro Val
                180                 185                 190

Gly Ser Ile Leu Trp Leu Gly Pro Leu Phe Val Pro Gly Glu Thr Gly
                195                 200                 205

Cys Trp His Cys Leu Ala Gln Arg Leu Gln Gly Asn Arg Glu Val Glu
210                 215                 220

Ala Ser Val Leu Gln Gln Lys Arg Ala Leu Gln Glu Arg Asn Gly Gln
225                 230                 235                 240

Asn Lys Asn Gly Ala Val Ser Cys Leu Pro Thr Ala Arg Ala Thr Leu
                245                 250                 255

Pro Ser Thr Leu Gln Thr Gly Leu Gln Trp Ala Ala Thr Glu Ile Ala
                260                 265                 270

Lys Trp Met Val Lys Arg His Leu Asn Ala Ile Ala Pro Gly Thr Ala
                275                 280                 285

Arg Phe Pro Thr Leu Ala Gly Lys Ile Phe Thr Phe Asn Gln Thr Thr
                290                 295                 300

Leu Glu Leu Lys Ala His Pro Leu Ser Arg Arg Pro Gln Cys Pro Thr
305                 310                 315                 320

Cys Gly Asp Arg Glu Thr Leu Gln Arg Arg Gly Phe Glu Pro Leu Lys
                325                 330                 335

Leu Glu Ser Arg Pro Lys His Phe Thr Ser Asp Gly Gly His Arg Ala
                340                 345                 350

Met Thr Pro Glu Gln Thr Val Gln Lys Tyr Gln His Leu Ile Gly Pro
                355                 360                 365

Ile Thr Gly Val Val Thr Glu Leu Val Arg Ile Ser Asp Pro Ala Asn
                370                 375                 380

Pro Leu Val His Thr Tyr Arg Ala Gly His Ser Phe Gly Ser Ala Thr
385                 390                 395                 400

Ser Leu Arg Gly Leu Arg Asn Val Leu Arg His Lys Ser Ser Gly Lys
                405                 410                 415

Gly Lys Thr Asp Ser Gln Ser Arg Ala Ser Gly Leu Cys Glu Ala Ile
                420                 425                 430

Glu Arg Tyr Ser Gly Ile Phe Gln Gly Asp Glu Pro Arg Lys Arg Ala
                435                 440                 445

Thr Leu Ala Glu Leu Gly Asp Leu Ala Ile His Pro Glu Gln Cys Leu
                450                 455                 460

His Phe Ser Asp Arg Gln Tyr Asp Asn Arg Glu Ser Ser Asn Glu Arg
465                 470                 475                 480

Ala Thr Val Thr His Asp Trp Ile Pro Gln Arg Phe Asp Ala Ser Lys
```

-continued

```
                485                 490                 495
Ala His Asp Trp Thr Pro Val Trp Ser Leu Thr Glu Gln Thr His Lys
            500                 505                 510

Tyr Leu Pro Thr Ala Leu Cys Tyr Tyr Arg Tyr Pro Phe Pro Pro Glu
            515                 520                 525

His Arg Phe Cys Arg Ser Asp Ser Asn Gly Asn Ala Ala Gly Asn Thr
            530                 535                 540

Leu Glu Glu Ala Ile Leu Gln Gly Phe Met Glu Leu Val Glu Arg Asp
545                 550                 555                 560

Ser Val Cys Leu Trp Trp Tyr Asn Arg Val Ser Arg Pro Ala Val Asp
            565                 570                 575

Leu Ser Ser Phe Asp Glu Pro Tyr Phe Leu Gln Leu Gln Gln Phe Tyr
            580                 585                 590

Gln Thr Gln Asn Arg Asp Leu Trp Val Leu Asp Leu Thr Ala Asp Leu
            595                 600                 605

Gly Ile Pro Ala Phe Val Gly Val Ser Asn Arg Lys Ala Gly Ser Ser
            610                 615                 620

Glu Arg Ile Ile Leu Gly Phe Gly Ala His Leu Asp Pro Thr Val Ala
625                 630                 635                 640

Ile Leu Arg Ala Leu Thr Glu Val Asn Gln Ile Gly Leu Glu Leu Asp
            645                 650                 655

Lys Val Ser Asp Glu Ser Leu Lys Asn Asp Ala Thr Asp Trp Leu Val
            660                 665                 670

Asn Ala Thr Leu Ala Ala Ser Pro Tyr Leu Val Ala Asp Ala Ser Gln
            675                 680                 685

Pro Leu Lys Thr Ala Lys Asp Tyr Pro Arg Arg Trp Ser Asp Asp Ile
            690                 695                 700

Tyr Thr Asp Val Met Thr Cys Val Glu Ile Ala Lys Gln Ala Gly Leu
705                 710                 715                 720

Glu Thr Leu Val Leu Asp Gln Thr Arg Pro Asp Ile Gly Leu Asn Val
            725                 730                 735

Val Lys Val Ile Val Pro Gly Met Arg Phe Trp Ser Arg Phe Gly Ser
            740                 745                 750

Gly Arg Leu Tyr Asp Val Pro Val Lys Leu Gly Trp Arg Glu Gln Pro
            755                 760                 765

Leu Ala Glu Ala Gln Met Asn Pro Thr Pro Met Pro Phe
            770                 775                 780

<210> SEQ ID NO 5
<211> LENGTH: 320
<212> TYPE: PRT
<213> ORGANISM: Prochloron didemni

<400> SEQUENCE: 5

Met Asp Leu Ile Asp Arg Leu Gln Asn Asn Gln Arg Lys Asp Arg Arg
1               5                   10                  15

Leu Gln Phe Val Arg Thr His Gln Glu Ala Phe Asp Val Lys Pro Thr
            20                  25                  30

Phe Pro Leu Pro Leu Phe Glu Glu Ala Ile Leu Glu Ile Glu Gly Ser
        35                  40                  45

Cys Ser Val Glu Ser Ser Cys Gln Val Glu Gly Asp Arg Leu Gln Gly
    50                  55                  60

Gly Arg Tyr Glu Val Cys Asn Asn Gln Gly Thr Thr Trp Pro Glu Ser
65                  70                  75                  80
```

```
Leu Thr His Ala Phe Lys Leu Leu Asp Lys Ile Asp Ser Gln Leu Gly
            85                  90                  95

Val Arg Ile Asn Arg Asp Ser Phe Asp Arg Phe Ala Ala Ala His Val
        100                 105                 110

Asn Ser Arg Lys Ile Ile Asn Asn Thr Ile Gly Val His Leu Gly Ser
        115                 120                 125

Lys Leu Glu Asp Ser Ser Val Met Leu Tyr Ile His Ile Lys Pro Glu
        130                 135                 140

Glu Asp Thr Glu Glu Leu Ala Arg Thr Ala Leu Val Leu Asp Gly Gly
145                 150                 155                 160

Arg Tyr Ser Asp Glu Leu Thr Arg Val Leu Leu Arg Asp Thr Met Val
                165                 170                 175

Ile Gly Phe Glu Leu Phe Phe Asp Gly Arg Ser Arg Val Asp Leu Gly
                180                 185                 190

Pro Cys Ala Pro Gly Lys Ser Gly Thr Leu Lys Met Lys Gly Lys His
                195                 200                 205

Leu Glu Gln Tyr Thr Gln Lys Asn Leu Ser Arg Lys Val Asn Ser Ile
        210                 215                 220

Phe Arg Glu Gly Tyr Leu Phe Gly Ala Phe Phe Ser Lys Thr Arg Val
225                 230                 235                 240

Glu Pro Ile Leu Phe Phe Tyr His Ser Ile Ile Lys Asp Leu Pro Lys
                245                 250                 255

Tyr Phe Thr Phe Asn Ser Leu Gly Asp Lys Ile Tyr Asn Phe Cys Gln
                260                 265                 270

Ser Gln Gly Cys Ile Thr Asp Val Ala Ile Ala Val Thr Glu Thr Glu
        275                 280                 285

Leu Glu Lys Ser Arg Leu Glu Asn Phe Cys Phe Tyr Tyr Asp Gln Trp
        290                 295                 300

Asp Glu Cys Lys Pro Ser Ser Asp Tyr Asp Thr Glu Arg His Leu His
305                 310                 315                 320

<210> SEQ ID NO 6
<211> LENGTH: 5
<212> TYPE: PRT
<213> ORGANISM: Artificial sequence
<220> FEATURE:
<223> OTHER INFORMATION: Synthetic sequence
<220> FEATURE:
<223> OTHER INFORMATION: N-term heterocycle or may be absent
<220> FEATURE:
<221> NAME/KEY: MOD_RES
<222> LOCATION: (1)..(1)
<223> OTHER INFORMATION: Pro or may be absent
<220> FEATURE:
<223> OTHER INFORMATION: See specification as filed for detailed
      description of substitutions and preferred embodiments

<400> SEQUENCE: 6

Xaa Ala Tyr Asp Gly
1               5

<210> SEQ ID NO 7
<211> LENGTH: 326
<212> TYPE: PRT
<213> ORGANISM: Prochloron didemni

<400> SEQUENCE: 7

Ile Pro Gly Leu Ala Asp Leu His Asn Gln Thr Leu Gly Asp Pro Gln
1               5                   10                  15

Ile Thr Ile Val Ile Ile Asp Gly Asp Pro Asp Tyr Thr Leu Ser Cys
```

```
            20                  25                  30
Phe Glu Gly Ala Glu Val Ser Lys Val Phe Pro Tyr Trp His Glu Pro
         35                  40                  45

Ala Glu Pro Ile Thr Pro Glu Asp Tyr Ala Ala Phe Gln Ser Ile Arg
 50                  55                  60

Asp Gln Gly Leu Lys Gly Lys Glu Lys Glu Ala Leu Glu Ala Val
 65                  70                  75                  80

Ile Pro Asp Thr Lys Asp Arg Ile Val Leu Asn Asp His Ala Cys His
                 85                  90                  95

Val Thr Ser Thr Ile Val Gly Gln Glu His Ser Pro Val Phe Gly Ile
             100                 105                 110

Ala Pro Asn Cys Arg Val Ile Asn Met Pro Gln Asp Ala Val Ile Arg
         115                 120                 125

Gly Asn Tyr Asp Asp Val Met Ser Pro Leu Asn Leu Ala Arg Ala Ile
     130                 135                 140

Asp Leu Ala Leu Glu Leu Gly Ala Asn Ile Ile His Cys Ala Phe Cys
145                 150                 155                 160

Arg Pro Thr Gln Thr Ser Glu Gly Glu Glu Ile Leu Val Gln Ala Ile
                165                 170                 175

Lys Lys Cys Gln Asp Asn Val Leu Ile Val Ser Pro Thr Gly Asn
             180                 185                 190

Asn Ser Asn Glu Ser Trp Cys Leu Pro Ala Val Leu Pro Gly Thr Leu
         195                 200                 205

Ala Val Gly Ala Ala Lys Val Asp Gly Thr Pro Cys His Phe Ser Asn
     210                 215                 220

Trp Gly Gly Asn Asn Thr Lys Glu Gly Ile Leu Ala Pro Gly Glu Glu
225                 230                 235                 240

Ile Leu Gly Ala Gln Pro Cys Thr Glu Glu Pro Val Arg Leu Thr Gly
                245                 250                 255

Thr Ser Met Ala Ala Pro Val Met Thr Gly Ile Ser Ala Leu Leu Met
             260                 265                 270

Ser Leu Gln Val Gln Gln Gly Lys Pro Val Asp Ala Glu Ala Val Arg
         275                 280                 285

Thr Ala Leu Leu Lys Thr Ala Ile Pro Cys Asp Pro Glu Val Val Glu
     290                 295                 300

Glu Pro Glu Arg Cys Leu Arg Gly Phe Val Asn Ile Pro Gly Ala Met
305                 310                 315                 320

Lys Val Leu Phe Gly Gln
                325

<210> SEQ ID NO 8
<211> LENGTH: 335
<212> TYPE: PRT
<213> ORGANISM: Nostoc spongiaeforme

<400> SEQUENCE: 8

Ile Pro Gly Leu Ala Gln Leu His Asn Gln Thr Leu Gly Asp Pro Arg
1               5                  10                  15

Ile Thr Ile Val Ile Ile Asp Gly Asp Pro Asp His Thr Leu Ser Cys
             20                  25                  30

Phe Ala Arg Ala Glu Val Ser Lys Val Phe Pro Tyr Trp His Glu Pro
         35                  40                  45

Ala Glu Pro Ile Ser Pro Glu His Tyr Ala Ser Phe Gln Ala Ile Arg
     50                  55                  60
```

```
Asp Lys Gly Leu Lys Gly Lys Glu Lys Glu Gln Ala Ile Asp Ala Ala
 65                  70                  75                  80

Leu Pro Lys Asn Val Lys Thr Arg Ile Glu Ile Asn Asp His Ala Cys
                 85                  90                  95

His Ile Thr Ser Ile Ile Val Gly Gln Glu His Ser Pro Val Phe Gly
            100                 105                 110

Ile Ala Pro Lys Cys Arg Val Ile Asn Met Pro His Asp Ala Leu Ala
        115                 120                 125

Asn His Asp Asp Ile Gln Ser Pro Leu Glu Asn Tyr Asp Asp Ile Ile
130                 135                 140

Ser Pro Leu Asn Leu Ala Arg Ala Phe Glu Leu Ala Leu Glu Leu Gly
145                 150                 155                 160

Ala Asn Ile Ile His Cys Ala Phe Cys Arg Pro Thr Arg Thr Ser Val
                165                 170                 175

Gly Glu Glu Ile Leu Val Lys Ala Ile Lys Lys Cys Leu Asp Asn Asn
            180                 185                 190

Ile Leu Ile Val Ala Pro Val Gly Asn Ser Asn Lys Asn Trp Cys
        195                 200                 205

Leu Pro Ala Val Leu Pro Gly Ile Leu Ala Val Gly Ala Ala Lys Val
210                 215                 220

Asp Gly Thr Pro Ala His Phe Ser Asn Trp Gly Gly Asn Asn Thr Gln
225                 230                 235                 240

Glu Gly Ile Leu Ala Pro Gly Val Asp Val Leu Gly Ala Gln Pro Cys
                245                 250                 255

Thr Glu Lys Pro Val Arg Gln Thr Gly Ser Ser Met Ala Ala Pro Val
            260                 265                 270

Ile Thr Gly Ile Ser Ala Leu Leu Met Ser Leu Gln Leu Gln Arg
        275                 280                 285

Lys Pro Val Asp Ala Glu Ala Ile Arg Ala Ala Leu Leu Asn Thr Ala
290                 295                 300

Ile Pro Cys Asp Pro Lys Val Val Glu Pro Glu Gln Cys Leu Arg
305                 310                 315                 320

Gly Phe Val Asn Ile Pro Gly Ala Met Lys Met Leu Phe Gly Gln
                325                 330                 335

<210> SEQ ID NO 9
<211> LENGTH: 333
<212> TYPE: PRT
<213> ORGANISM: Prochloron sp.

<400> SEQUENCE: 9

Ile Pro Gly Leu Val Glu Leu His Asn Gln Thr Leu Gly Asp Pro Arg
1               5                   10                  15

Ile Thr Ile Val Val Ile Asp Gly Glu Pro Asp Tyr Ser Leu Ser Cys
            20                  25                  30

Leu Gln Gly Ala Glu Val Ser Lys Ala Phe Pro Tyr Trp His Glu Pro
        35                  40                  45

Ala Glu Ala Ile Pro Gln Glu Asp Tyr Ala Thr Phe Gln Glu Ile Arg
    50                  55                  60

Asp Gln Gly Leu Lys Gly Lys Ala Lys Gln Glu Ala Leu Glu Ala Ala
65                  70                  75                  80

Ile Pro Glu Thr Arg Asn Arg Val Glu Leu Asn Asp His Ser Cys His
                85                  90                  95

Val Thr Ser Ile Ile Val Gly Gln Glu His Ser Pro Val Phe Gly Ile
            100                 105                 110
```

```
Ala Pro Arg Cys Arg Val Ile Asn Met Pro His Asp Ala Val Ile Lys
            115                 120                 125

Pro Asp Asn Gly Val Glu Ser Ser Gly Tyr Ser Asp Met Leu Ser Pro
130                 135                 140

Leu Asn Met Ala Arg Ala Leu Glu Phe Ala Leu Glu Leu Gly Ala Asp
145                 150                 155                 160

Ile Ile His Cys Gly Phe Cys Arg Pro Thr Gln Thr Gly Glu Gly Glu
                165                 170                 175

Glu Leu Leu Val Gln Ala Val Lys Lys Cys Gln Asp Asn Asn Val Leu
            180                 185                 190

Ile Val Ser Pro Thr Gly Asn Asn Leu Gly Glu Cys Trp Cys Met Pro
        195                 200                 205

Ala Val Leu Pro Gly Thr Leu Gly Val Gly Ala Ala Lys Val Asp Gly
    210                 215                 220

Thr Pro Cys His Phe Ser Asn Trp Gly Gly Asn Asn Ala Glu Glu Gly
225                 230                 235                 240

Ile Leu Ala Pro Gly Glu Asp Val Leu Gly Ala Gln Pro Tyr Thr Asp
                245                 250                 255

Lys Pro Val Arg Leu Thr Gly Thr Ser Met Ser Ala Pro Val Met Thr
            260                 265                 270

Gly Ile Ser Ala Leu Leu Met Ser Leu Gln Val Gln Gln Gly Lys Pro
        275                 280                 285

Val Asp Ala Glu Ala Val Arg Thr Ala Leu Leu Lys Thr Ala Ile Pro
    290                 295                 300

Cys Asp Pro Glu Val Val Glu Glu Pro Glu Arg Cys Leu Arg Gly Phe
305                 310                 315                 320

Val Asn Ile Pro Gly Ala Met Lys Val Leu Phe Gly Gln
                325                 330

<210> SEQ ID NO 10
<211> LENGTH: 333
<212> TYPE: PRT
<213> ORGANISM: Microcystis aeruginosa

<400> SEQUENCE: 10

Ile Pro Gly Leu Ala Glu Leu His Asn Gln Thr Leu Gly Asp Pro Arg
1               5                   10                  15

Ile Thr Ile Val Ile Leu Asp Gly Asn Pro Asp His Thr Leu Ser Cys
            20                  25                  30

Phe Ala Gly Ala Asn Val Ser Lys Val Phe Pro Tyr Trp His Glu Pro
        35                  40                  45

Ala Asp Pro Ile Ser Pro Glu Asp Tyr Ala Thr Phe Gln Ala Ile Arg
    50                  55                  60

Asp Gln Gly Leu Lys Gly Lys Ala Lys Gln Glu Ala Leu Glu Ser Ala
65                  70                  75                  80

Ile Pro Asp Thr Ile Asn Arg Val Glu Leu Asn Asp His Ala Cys His
                85                  90                  95

Val Thr Ser Thr Ile Val Gly Gln Glu His Ser Pro Val Phe Gly Ile
            100                 105                 110

Ala Pro Asn Cys Arg Val Ile Asn Met Pro His Asp Ala Val Val Thr
        115                 120                 125

Ser Asp Asn Gly Ile Ala Leu Ser Gly Tyr Asn Glu Val Leu Ser Pro
    130                 135                 140

Leu Asn Leu Ala Arg Ala Phe Asp Leu Ala Leu Glu Leu Gly Ala Asn
```

-continued

```
                145                 150                 155                 160

Ile Ile His Cys Ala Phe Cys Arg Pro Thr Gln Thr Gly Glu Gly Glu
            165                 170                 175

Glu Ile Leu Val Lys Ala Ile Lys Lys Cys Ile Asp Asn Asn Ile Leu
            180                 185                 190

Ile Val Ser Pro Thr Gly Asn Asn Leu Gly Glu Cys Trp Cys Met Pro
            195                 200                 205

Ala Val Leu Pro Gly Thr Leu Ala Val Gly Ala Ala Lys Val Asp Gly
            210                 215                 220

Thr Pro Cys His Phe Ser Asn Trp Gly Gly Asn Asn Gly Glu Glu Gly
225                 230                 235                 240

Ile Leu Ala Pro Gly Glu Asp Ile Leu Gly Ala Gln Pro Cys Thr Glu
            245                 250                 255

Lys Pro Val Arg Leu Thr Gly Thr Ser Met Ala Ala Pro Val Met Thr
            260                 265                 270

Gly Ile Ala Ala Leu Leu Met Ser Leu Gln Val Gln Gln Gly Lys Pro
            275                 280                 285

Val Asp Ala Glu Ala Val Arg Thr Ala Leu Leu Asn Thr Ala Ile Pro
            290                 295                 300

Cys Asp Pro Asn Val Val Glu Glu Ala Glu Arg Cys Leu Arg Gly Phe
305                 310                 315                 320

Val Asn Ile Pro Gly Ala Met Lys Val Leu Phe Gly Gln
            325                 330

<210> SEQ ID NO 11
<211> LENGTH: 333
<212> TYPE: PRT
<213> ORGANISM: Microcystis aeruginosa

<400> SEQUENCE: 11

Ile Pro Gly Leu Ala Glu Leu His Asn Gln Thr Leu Gly Asp Pro Arg
1               5                   10                  15

Ile Thr Ile Val Ile Leu Asp Gly Asn Pro Asp His Thr Leu Ser Cys
            20                  25                  30

Phe Ala Gly Ala Asn Val Ser Lys Val Phe Pro Tyr Trp His Glu Pro
            35                  40                  45

Ala Asp Pro Ile Ser Pro Glu Asp Tyr Ala Thr Phe Gln Ala Ile Arg
        50                  55                  60

Asp Gln Gly Leu Lys Gly Lys Ala Lys Gln Glu Ala Leu Glu Ser Ala
65                  70                  75                  80

Ile Pro Asp Thr Ile Asn Arg Val Glu Leu Asn Asp His Ala Cys His
            85                  90                  95

Val Thr Ser Thr Ile Val Gly Gln Glu His Ser Pro Val Phe Gly Ile
            100                 105                 110

Ala Pro Asn Cys Arg Val Ile Asn Met Pro His Asp Ala Val Val Thr
            115                 120                 125

Ser Asp Asn Gly Ile Ala Leu Ser Gly Tyr Asn Glu Val Leu Ser Pro
130                 135                 140

Leu Asn Leu Ala Arg Ala Phe Glu Leu Ala Ile Glu Leu Gly Ala Asn
145                 150                 155                 160

Val Ile His Cys Ala Phe Cys Arg Pro Thr Gln Thr Gly Glu Gly Glu
            165                 170                 175

Glu Ile Leu Val Lys Ala Ile Lys Lys Cys Ile Asp Asn Asn Ile Leu
            180                 185                 190
```

```
Ile Val Ser Pro Thr Gly Asn Asn Leu Gly Glu Cys Trp Cys Met Pro
            195                 200                 205

Ala Val Leu Pro Gly Thr Leu Ala Val Gly Ala Ala Lys Val Asp Gly
    210                 215                 220

Thr Pro Cys His Phe Ser Asn Trp Gly Gly Asn Asn Gly Glu Glu Gly
225                 230                 235                 240

Ile Leu Ala Pro Gly Glu Asp Ile Leu Gly Ala Gln Pro Cys Thr Glu
                245                 250                 255

Lys Pro Val Arg Leu Thr Gly Thr Ser Met Ala Ala Pro Val Met Thr
            260                 265                 270

Gly Ile Ala Ala Leu Leu Met Ser Leu Gln Val Gln Gln Gly Lys Pro
        275                 280                 285

Val Asp Ala Glu Ala Val Arg Thr Ala Leu Leu Asn Thr Ala Ile Pro
290                 295                 300

Cys Asp Pro Asn Val Val Glu Glu Pro Glu Arg Cys Leu Arg Gly Phe
305                 310                 315                 320

Val Asn Ile Pro Gly Ala Met Lys Val Leu Phe Gly Gln
                325                 330

<210> SEQ ID NO 12
<211> LENGTH: 326
<212> TYPE: PRT
<213> ORGANISM: Lyngbya sp.

<400> SEQUENCE: 12

Ile Pro Gly Leu Ala Glu Leu His Asn Gln Thr Leu Gly Asp Pro Arg
1               5                   10                  15

Ile Thr Ile Val Ile Leu Asp Gly Asn Pro Asp His Thr Leu Ser Cys
            20                  25                  30

Phe Gln Gly Ala Asp Val Ser Lys Val Phe Pro Tyr Trp His Glu Ile
        35                  40                  45

Pro Glu Pro Ile Ser Pro Glu Asp Tyr Ala Thr Tyr Leu Glu Ile Asp
    50                  55                  60

Asn Gly Asn Leu Lys Gly Glu Ala Lys Lys Ala Ala Leu Glu Ala Ala
65              70                  75                  80

Leu Pro Glu Pro Ile Leu His Arg Ile Gln Gly Asp Tyr His Ala Cys
                85                  90                  95

Leu Val Thr Ser Val Ile Val Gly Gln Glu Asn Thr Pro Val Pro Gly
            100                 105                 110

Ile Ala Pro Lys Cys Arg Val Ile Asn Ile Pro Leu Asn Ser Met Gly
        115                 120                 125

Arg Ile Asp Glu Glu Ala Ile Ser Pro Leu Asn Leu Ala Arg Ala Phe
    130                 135                 140

Asp Leu Ala Leu Glu Leu Gly Ala Asn Ile Ile His Cys Ala Met Cys
145                 150                 155                 160

Arg Pro Thr Gln Thr Gly Lys Gly Glu Glu Leu Leu Thr Gln Ala Val
                165                 170                 175

Lys Lys Cys Gln Asp Asn Asn Ile Leu Ile Val Ser Pro Thr Gly Asn
            180                 185                 190

Asp Lys Gly Glu Cys Trp Cys Leu Pro Ala Val Leu Pro Gly Thr Leu
        195                 200                 205

Ala Val Gly Ala Ala Lys Val Asp Gly Thr Pro Cys His Phe Ser Asn
    210                 215                 220

Trp Gly Gly Asn Asn Ala Glu Glu Gly Ile Leu Ala Pro Gly Glu Asp
225                 230                 235                 240
```

Ile Leu Gly Ala Gln Pro Cys Thr Glu Glu Pro Val Arg Lys Thr Gly
                    245                 250                 255

Thr Ser Leu Ala Ala Pro Val Met Thr Gly Ile Ser Ala Leu Leu Met
                260                 265                 270

Ser Leu Gln Val Gln Gln Gly Lys Thr Val Asp Ala Glu Ala Val Arg
            275                 280                 285

Thr Ala Leu Leu Asn Thr Ala Ile Pro Cys Asp Pro Asn Val Val Glu
        290                 295                 300

Glu Pro Glu Arg Cys Leu Arg Gly Phe Val Asn Ile Pro Gly Ala Met
305                 310                 315                 320

Lys Val Leu Phe Gly Gln
                325

<210> SEQ ID NO 13
<211> LENGTH: 323
<212> TYPE: PRT
<213> ORGANISM: Trichodesmium erythraeum

<400> SEQUENCE: 13

Ile Pro Gly Leu Thr Lys Leu Trp Thr His Thr Lys Gly Asp Pro Arg
1               5                   10                  15

Ile Thr Val Ala Leu Leu Asp Gly Thr Ala Asp Ile Glu Arg Gly Cys
            20                  25                  30

Phe Gln Gly Ala Asn Val Thr Lys Ile Asn Ser Tyr Trp Gln Glu Ala
        35                  40                  45

Ile Glu Leu Asp Pro Lys Asp Ile Asp Thr Tyr Arg Glu Ile Gln Asn
    50                  55                  60

Ser Asp Glu Lys Ser Glu Val Lys Gln Ala Lys Leu Lys Glu Ala Ile
65                  70                  75                  80

Pro Asp Glu Ile Thr Leu Gln Ile Leu Gly Ala Ala Phe His Ala Thr
                85                  90                  95

His Val Phe Ser Asn Ile Phe Gly Gln Pro Gly Thr Pro Val Glu Gly
            100                 105                 110

Ile Ala Tyr Lys Cys Arg Gly Ile Asn Ile Pro Leu Gly Tyr Gly Asn
        115                 120                 125

Asp Tyr Tyr Ile Asp Pro Ile Asn Leu Ala Arg Gly Ile Asn Leu Ala
    130                 135                 140

Val Asp Leu Gly Ala Asn Ile Ile His Cys Ala Ala Cys Arg Pro Asn
145                 150                 155                 160

Gln Thr Gly Ile Gly His Glu Ile Leu Glu Lys Ala Val Arg Gln Ala
                165                 170                 175

Gln Glu Asn Asn Val Leu Ile Val Ala Pro Thr Gly Asn Asn Lys Gly
            180                 185                 190

Glu Cys Trp Cys Leu Pro Ala Ile Leu Pro Gly Val Met Ser Val Gly
        195                 200                 205

Ala Met Lys Asp Asn Gly Gln Val Phe Lys Phe Ser Asn Trp Gly Gly
    210                 215                 220

Gln Tyr Gln Gln Gln Gly Ile Ile Ala Pro Gly Glu Asn Ile Leu Gly
225                 230                 235                 240

Ala Gln Pro Gly Thr Glu Glu Thr Val Arg Gln Lys Gly Thr Ser Cys
                245                 250                 255

Ala Ala Pro Met Val Thr Ala Ile Ser Ala Leu Leu Met Ser Leu Gln
            260                 265                 270

Leu Gln Gln Gly Ala Ser Pro Asp Ala Glu Ala Val Arg Ala Ala Leu

```
                    275                 280                 285
Thr Asn Ser Ala Ile Pro Cys Thr Leu Glu Asp Thr Glu Glu Ile Glu
    290                 295                 300

Arg Cys Met Leu Gly Lys Leu Asn Val Ala Gly Ala Tyr Gln Leu Leu
305                 310                 315                 320

Thr Gly Lys

<210> SEQ ID NO 14
<211> LENGTH: 325
<212> TYPE: PRT
<213> ORGANISM: Oscillatoria sp.

<400> SEQUENCE: 14

Leu Pro Gly Leu Tyr Asp Leu Trp Ala His Thr Lys Gly Asp His Glu
1               5                   10                  15

Ile Thr Ile Val Ile Leu Asp Gly Asn Ala Asp Leu Glu Arg Ser Cys
                20                  25                  30

Phe Gln Gly Ala Asn Ile Ser Lys Ile Phe Pro Tyr Trp His Glu Thr
            35                  40                  45

Pro Glu Pro Ile Ala Leu Glu Tyr Tyr Glu Ala Phe Leu Glu Ile Glu
        50                  55                  60

Lys Ser Gly Glu Lys Gly Glu Ala Lys Ala Lys Leu Gln Ala Ala
65                  70                  75                  80

Val Pro Glu Ala Ile Leu Asn Arg Leu Lys Gly Asn Phe His Ala Thr
                    85                  90                  95

His Ile Ile Ser Thr Ile Ile Gly Gln His Gly Ser Pro Val Pro Gly
                100                 105                 110

Ile Ala Pro Arg Cys Arg Ala Ile Asn Ile Pro Ile Asn Thr Thr Gly
            115                 120                 125

Asp Asn Gly Glu Phe Ile Ser Pro Ile Asn Leu Thr Arg Ala Phe Glu
        130                 135                 140

Leu Ala Met Lys Leu Gly Ala Asn Ile Ile His Cys Ala Ala Cys Cys
145                 150                 155                 160

Ala Thr Gln Thr Gly Ile Ala His Asp Leu Leu Ala Arg Ala Val Lys
                165                 170                 175

Asn Cys Gln Asp Asn Asn Ile Leu Ile Val Ala Pro Thr Gly Asn Asp
            180                 185                 190

Lys Gly Glu Cys Trp Cys Ile Pro Ala Ile Leu Pro Gly Val Leu Gly
        195                 200                 205

Ala Gly Met Met Lys Asp Asn Gly Lys Pro Ala Asn Tyr Ser Asn Trp
    210                 215                 220

Gly Gly Asn Tyr Gln His Asp Gly Ile Leu Ala Pro Gly Glu Asn Ile
225                 230                 235                 240

Leu Gly Ala Gln Pro Thr Thr Glu Thr Lys Leu Ser Gln Gly Thr
                245                 250                 255

Ser Cys Ala Ala Pro Ile Val Thr Gly Val Ser Ala Leu Phe Leu Ser
            260                 265                 270

Leu Gln Leu Gln Arg Gly Glu Lys Pro Asn Ala Glu Ala Val Arg Gln
        275                 280                 285

Ala Ile Leu Asn Ser Ala Ile Pro Cys Asp Pro Glu Glu Ile Glu Glu
    290                 295                 300

Pro Glu Arg Cys Leu Arg Gly Lys Leu Asn Ile Pro Gly Ala Tyr Gln
305                 310                 315                 320

Leu Leu Thr Gly Lys
```

<210> SEQ ID NO 15
<211> LENGTH: 325
<212> TYPE: PRT
<213> ORGANISM: Arthrospira platensis

<400> SEQUENCE: 15

```
Ile Pro Gly Leu Ala Glu Leu Arg Asn Gln Thr Leu Gly Asp Pro Arg
1               5                   10                  15

Ile Thr Ile Val Ile Leu Asp Gly Asn Pro Asp His Thr Leu Ser Cys
            20                  25                  30

Phe Glu Gly Ala Glu Val Ser Lys Val Phe Pro Tyr Trp His Pro Pro
        35                  40                  45

Ala Glu Pro Val Pro Thr Glu Ala Tyr His Gln Phe Gln Ala Ile Gly
    50                  55                  60

Asn Asp Asp Thr Leu Asp Lys Asp Gln Lys Ala Glu Ala Gln Lys Ala
65                  70                  75                  80

Ala Leu Ser Glu Pro Leu Leu Lys Arg Ile His Gly Asp Asn His Ala
                85                  90                  95

Cys His Ile Thr Ser Thr Ile Val Gly Gln Glu Asn Thr Pro Ser Pro
            100                 105                 110

Gly Leu Ala Pro Arg Cys Arg Val Ile Asn Ile Pro Leu Asn Thr Thr
        115                 120                 125

Gly Thr Asp Glu Glu Phe Ile Ser Pro Leu Ser Leu Ala Arg Ala Phe
    130                 135                 140

Glu Leu Gly Leu Asn Leu Gly Ala Asn Ile Ile His Cys Ala Ala Cys
145                 150                 155                 160

Arg Pro Thr Gln Thr Gly Glu Gly Glu Leu Leu Leu Gln Ala Leu
                165                 170                 175

Lys Lys Cys Gln Asp Asn Asn Ile Leu Ile Val Ala Pro Ala Gly Asn
            180                 185                 190

Asn Lys Gly Glu Cys Trp Cys Met Pro Ala Ser Leu Pro Gly Val Leu
        195                 200                 205

Ser Val Gly Ala Leu Lys Pro Asp Gly Thr Pro Tyr Lys Phe Ser Asn
    210                 215                 220

Trp Gly Gly Asn Asn Ala Leu Glu Gly Ile Met Ala Pro Gly Gly Glu
225                 230                 235                 240

Ile Leu Gly Ala Gln Pro Ala Asn Glu Ala Pro Val Arg Leu Gln Gly
                245                 250                 255

Thr Ser Met Ala Ala Pro Val Met Thr Gly Leu Cys Ser Leu Leu Met
            260                 265                 270

Ser Leu Gln Leu Gln Gln Gly Lys Pro Val Asp Ala Glu Ala Val Arg
        275                 280                 285

Ala Ala Leu Leu Asn Thr Ala Ile Pro Cys Thr Pro Asp Asp Thr Asp
    290                 295                 300

Glu Pro Glu Arg Cys Leu Arg Gly Lys Val Asn Leu Pro Gly Ala Met
305                 310                 315                 320

Gly Leu Leu Phe Gly
                325
```

<210> SEQ ID NO 16
<211> LENGTH: 325
<212> TYPE: PRT
<213> ORGANISM: Arthrospira platensis

<400> SEQUENCE: 16

Ile Pro Gly Leu Ala Glu Leu Arg Asn Gln Thr Leu Gly Asp Pro Arg
1               5                   10                  15

Ile Thr Ile Val Ile Leu Asp Gly Asn Pro Asp His Thr Leu Ser Cys
            20                  25                  30

Phe Glu Gly Ala Glu Val Ser Lys Val Phe Pro Tyr Trp His Pro Pro
        35                  40                  45

Ala Glu Pro Val Pro Thr Glu Ala Tyr His Gln Phe Gln Ala Ile Gly
    50                  55                  60

Asn Asp Asp Thr Leu Asp Lys Asp Gln Lys Ala Glu Ala Gln Lys Ala
65                  70                  75                  80

Ala Leu Ser Glu Pro Leu Leu Lys Arg Ile His Gly Asp Asn His Ala
                85                  90                  95

Cys His Ile Thr Ser Thr Ile Val Gly Gln Glu Asn Thr Pro Ser Pro
            100                 105                 110

Gly Leu Ala Pro Arg Cys Arg Val Ile Asn Ile Pro Leu Asn Thr Thr
        115                 120                 125

Gly Thr Asp Glu Glu Phe Ile Ser Pro Leu Ser Leu Ala Arg Ala Phe
130                 135                 140

Glu Leu Gly Leu Asn Leu Gly Ala Asn Ile Ile His Cys Ala Ala Cys
145                 150                 155                 160

Arg Pro Thr Gln Thr Gly Glu Gly Glu Leu Leu Leu Gln Ala Leu
                165                 170                 175

Lys Lys Cys Gln Asp Asn Asn Ile Leu Ile Val Ala Pro Ala Gly Asn
            180                 185                 190

Asn Lys Gly Glu Cys Trp Cys Met Pro Ala Ser Leu Pro Gly Val Leu
        195                 200                 205

Ser Val Gly Ala Leu Lys Pro Asp Gly Thr Pro Tyr Lys Phe Ser Asn
    210                 215                 220

Trp Gly Gly Asn Asn Ala Leu Glu Gly Ile Met Ala Pro Gly Gly Glu
225                 230                 235                 240

Ile Leu Gly Ala Gln Pro Ala Asn Glu Ala Pro Val Arg Leu Gln Gly
                245                 250                 255

Thr Ser Met Ala Ala Pro Val Met Thr Gly Leu Cys Ser Leu Leu Met
            260                 265                 270

Ser Leu Gln Leu Gln Gln Gly Lys Pro Val Asp Ala Glu Ala Val Arg
        275                 280                 285

Ala Ala Leu Leu Asn Thr Ala Ile Pro Cys Thr Pro Asp Asp Thr Asp
    290                 295                 300

Glu Pro Glu Arg Cys Leu Arg Gly Lys Val Asn Leu Pro Gly Ala Met
305                 310                 315                 320

Gly Leu Leu Phe Gly
                325

<210> SEQ ID NO 17
<211> LENGTH: 336
<212> TYPE: PRT
<213> ORGANISM: Nodularia spumigena

<400> SEQUENCE: 17

Ile Pro Gly Ile Ser Gln Ile Trp Thr Arg Thr Lys Gly Asp Pro Arg
1               5                   10                  15

Ile Lys Ile Ala Ile Leu Asp Gly Ala Ala Asp Leu Glu Arg Ser Cys
            20                  25                  30

Phe Gln Gly Ala Asn Phe Ser Gln Phe Gln Pro Tyr Trp Ser Glu Asp
            35                  40                  45

Ile Glu Leu Asn Glu Glu Tyr Phe Tyr Tyr Leu Asn Leu Ser Leu Glu
 50                  55                  60

Phe Asn Gln Gln Gln Lys Asp Lys Lys Asp Asp Pro Asp His Asp Lys
 65                  70                  75                  80

Glu Glu Ala Lys Lys Glu Arg Glu Ala Phe Phe Ala Pro Phe Pro Pro
                 85                  90                  95

Ala Ile Arg Gln Arg Ile Glu Leu Ser Ser His Ala Thr His Ile Ser
            100                 105                 110

Ser Thr Ile Leu Gly Gln His Gly Thr Pro Ala Pro Gly Ile Ala Pro
        115                 120                 125

Leu Cys Thr Ala Leu Asn Ile Pro Ile Ser Phe Ala Gly Asp Asp Phe
130                 135                 140

Ile Ser Pro Ile Asn Leu Thr His Ala Ile Asn Thr Ala Leu Gln Trp
145                 150                 155                 160

Gly Ala Asn Ile Ile His Ile Ala Ala Cys His Pro Thr Gln Thr Gly
                165                 170                 175

Val Ala Pro Asp Leu Phe Ala Arg Ala Val Lys Gln Cys Gln Glu Asn
            180                 185                 190

Asn Met Leu Ile Val Ala Pro Gly Gly Asn Asp Lys Gly Glu Cys Trp
        195                 200                 205

Cys Ile Pro Ser Ile Leu Pro Gly Val Ile Thr Val Gly Ala Met Arg
210                 215                 220

Asp Asp Gly Gln Pro Phe Lys Phe Ser Asn Tyr Gly Gly Glu Tyr Gln
225                 230                 235                 240

Asn Lys Gly Val Met Ala Asn Gly Glu Asn Ile Leu Gly Ala Gln Pro
                245                 250                 255

Gly Thr Glu Glu Pro Ile Arg Glu Lys Gly Thr Ser Cys Ala Ala Pro
            260                 265                 270

Ile Val Thr Gly Ile Ser Ala Leu Leu Met Ser Met Gln Leu Gln Arg
        275                 280                 285

Gly Glu Gln Pro Asn Ala Glu Ala Val Arg Gln Ala Ile Leu Asn Ser
290                 295                 300

Ala Ile Pro Cys Asn Pro Glu Thr Val Glu Glu Pro Glu Arg Cys Leu
305                 310                 315                 320

Leu Gly Lys Phe Asn Ile Pro Gly Ala Phe Gln Leu Leu Thr Gly Glu
                325                 330                 335

<210> SEQ ID NO 18
<211> LENGTH: 336
<212> TYPE: PRT
<213> ORGANISM: Anabaena sp.

<400> SEQUENCE: 18

Ile Pro Gly Ile Ser Gln Ile Trp Thr Arg Thr Lys Gly Asp Pro Arg
 1               5                  10                  15

Ile Lys Ile Ala Ile Leu Asp Gly Ala Ala Asp Leu Glu Arg Ser Cys
            20                  25                  30

Phe Gln Gly Ala Lys Phe Ser Gln Phe Lys Pro Tyr Trp Ser Glu Asp
        35                  40                  45

Ile Glu Leu Asn Asp Glu Tyr Tyr Tyr Tyr Leu Asn Leu Tyr Leu Asp
 50                  55                  60

Phe Asn Gln Gln Gln Lys Asp Lys Lys Asp Asp Pro Asp His Asp Lys
 65                  70                  75                  80

Glu Glu Ser Lys Lys Glu Arg Glu Ala Phe Phe Ala Pro Phe Pro Pro
                85                  90                  95

Ala Ile Arg Gln Arg Ile Glu Leu Ser Gly His Ala Thr His Ile Ser
            100                 105                 110

Ser Thr Ile Leu Gly Gln His Gly Thr Pro Ala Pro Gly Ile Ala Pro
            115                 120                 125

Leu Cys Thr Ala Leu Asn Ile Pro Ile Ser Phe Ala Asn Asp Asp Phe
        130                 135                 140

Ile Ser Pro Ile Asn Leu Thr His Ala Val Asn Thr Ala Trp Gln Trp
145                 150                 155                 160

Gly Ala Asn Ile Ile His Ile Ala Ala Cys His Pro Thr Gln Thr Gly
                165                 170                 175

Val Ala Pro Asp Leu Phe Ala Arg Ala Val Lys Gln Cys Gln Asp Asn
            180                 185                 190

Asn Met Leu Ile Val Ala Pro Gly Gly Asn Asp Lys Gly Glu Cys Trp
            195                 200                 205

Cys Ile Pro Ser Ile Leu Pro Gly Val Ile Thr Val Gly Ala Met Arg
        210                 215                 220

Asp Asp Gly Gln Pro Phe Lys Phe Ser Asn Tyr Gly Gly Glu Tyr Gln
225                 230                 235                 240

Asn Lys Gly Val Met Ala Asn Gly Glu Asn Ile Leu Gly Ala Gln Pro
                245                 250                 255

Gly Thr Glu Glu Pro Ile Arg Gln Lys Gly Thr Ser Cys Ala Ala Pro
            260                 265                 270

Ile Val Thr Gly Ile Ser Ala Leu Leu Met Ser Leu Gln Leu Gln Arg
        275                 280                 285

Gly Glu Gln Pro Asn Ala Glu Ala Val Arg Glu Ala Ile Leu Asn Ser
        290                 295                 300

Ala Ile Pro Cys Asn Pro Glu Glu Val Glu Pro Glu Arg Cys Leu
305                 310                 315                 320

Leu Gly Lys Leu Asn Ile Pro Gly Ala Phe Gln Leu Thr Gly Glu
                325                 330                 335

<210> SEQ ID NO 19
<211> LENGTH: 336
<212> TYPE: PRT
<213> ORGANISM: Planktothrix agardhii

<400> SEQUENCE: 19

Ile Pro Gly Ile Pro Glu Leu Trp Thr Gln Thr Lys Gly Asp Ser Arg
1               5                   10                  15

Ile Lys Ile Ala Ile Leu Asp Gly Ala Ala Asp Leu Glu Arg Ala Cys
            20                  25                  30

Phe Lys Gly Ala Lys Ile Thr Gln Phe Lys Pro Tyr Trp Ala Glu Asp
        35                  40                  45

Ile Glu Leu Asn Asp Glu Tyr Tyr His Tyr Leu Lys Leu Ala Thr Glu
    50                  55                  60

Phe Asn Gln Gln Gln Lys Ala Lys Lys Glu Asp Pro Asp His Asp Lys
65                  70                  75                  80

Glu Glu Ala Lys Lys Glu Arg Glu Ala Phe Phe Lys Asp Phe Pro Glu
                85                  90                  95

Asp Ile Lys Arg Arg Ile Asp Leu Ser Ser His Ala Thr His Ile Ser
            100                 105                 110

Ser Thr Ile Leu Gly Gln His Gly Ser Pro Val Glu Gly Ile Ala Pro

```
                    115                 120                 125
Asn Cys Thr Ala Ile Asn Ile Pro Ile Ser Phe Ala Gly Asp Asp Phe
        130                 135                 140
Ile Ser Phe Val Asn Leu Thr His Ala Ile Asn Glu Ala Leu Lys Ala
145                 150                 155                 160
Glu Val Asn Ile Val His Ile Ala Ala Cys His Pro Thr Gln Ser Gly
                165                 170                 175
Met Ala Gln Glu Ile Phe Ala Arg Ala Val Lys Gln Cys Gln Asp Ser
            180                 185                 190
Asn Ile Leu Ile Val Ala Pro Gly Gly Asn Asp Lys Gly Glu Cys Trp
        195                 200                 205
Cys Ile Pro Ser Ile Leu Pro Asp Val Leu Thr Val Gly Ala Met Arg
    210                 215                 220
Asp Asp Gly Gln Pro Phe Lys Phe Ser Asn Tyr Gly Gly Glu Tyr Gln
225                 230                 235                 240
His Lys Gly Val Met Ala Asn Gly Glu Asn Ile Leu Gly Ala Asn Pro
                245                 250                 255
Gly Thr Asp Glu Pro Val Arg Glu Lys Gly Thr Ser Cys Ala Ala Pro
            260                 265                 270
Ile Val Thr Gly Ile Ser Ala Leu Leu Met Ser Met Gln Leu Gln Arg
        275                 280                 285
Gly Glu Lys Pro Asn Ala Glu Thr Val Arg Gln Ala Ile Leu Lys Ser
    290                 295                 300
Ala Ile Pro Cys Asp Gln Asn Glu Val Glu Pro Glu Arg Cys Leu
305                 310                 315                 320
Leu Gly Lys Leu Asn Ile Pro Gly Ala Tyr Asn Leu Leu Thr Gly Glu
                325                 330                 335

<210> SEQ ID NO 20
<211> LENGTH: 4
<212> TYPE: PRT
<213> ORGANISM: Artificial sequence
<220> FEATURE:
<223> OTHER INFORMATION: Synthetic sequence: Cyclisation sequence

<400> SEQUENCE: 20

Ala Tyr Asp Gly
1

<210> SEQ ID NO 21
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 21

Ile Thr Ala Cys Ile Thr Phe Cys
1               5

<210> SEQ ID NO 22
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 22

Ile Thr Ala Cys Ile Ser Phe Cys
1               5
```

```
<210> SEQ ID NO 23
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 23

Ile Cys Ala Cys Ile Thr Phe Cys
1               5

<210> SEQ ID NO 24
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 24

Ile Ala Ala Cys Ile Thr Phe Cys
1               5

<210> SEQ ID NO 25
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 25

Ile Thr Ala Cys Ile Thr Tyr Cys
1               5

<210> SEQ ID NO 26
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 26

Ile Thr Ala Cys Ile Thr Ala Cys
1               5

<210> SEQ ID NO 27
<211> LENGTH: 8
<212> TYPE: PRT
<213> ORGANISM: Artificial sequence
<220> FEATURE:
<223> OTHER INFORMATION: Synthetic sequence: Target peptide sequence.
<220> FEATURE:
<221> NAME/KEY: SITE
<222> LOCATION: (4, 8)
<223> OTHER INFORMATION: Xaa is SeCys

<400> SEQUENCE: 27

Ile Thr Ala Xaa Ile Thr Phe Xaa
1               5

<210> SEQ ID NO 28
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 28
```

```
Ile Met Ala Cys Ile Met Ala Cys
1               5

<210> SEQ ID NO 29
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 29

Ile Asp Ala Cys Ile Asp Phe Cys
1               5

<210> SEQ ID NO 30
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 30

Ile Thr Val Cys Ile Thr Val Cys
1               5

<210> SEQ ID NO 31
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 31

Ile Thr Ala Ala Ile Thr Phe Cys
1               5

<210> SEQ ID NO 32
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 32

Val Pro Ala Pro Ile Pro Phe Pro
1               5

<210> SEQ ID NO 33
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 33

Val Thr Val Cys Val Thr Val Cys
1               5

<210> SEQ ID NO 34
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 34
```

```
Val Gly Ala Gly Ile Gly Phe Pro
1               5

<210> SEQ ID NO 35
<211> LENGTH: 6
<212> TYPE: PRT
<213> ORGANISM: Artificial sequence
<220> FEATURE:
<223> OTHER INFORMATION: Synthetic sequence: Target peptide sequence.

<400> SEQUENCE: 35

Ala Cys Ile Met Ala Cys
1               5

<210> SEQ ID NO 36
<211> LENGTH: 7
<212> TYPE: PRT
<213> ORGANISM: Artificial sequence
<220> FEATURE:
<223> OTHER INFORMATION: Synthetic sequence: Target peptide sequence.

<400> SEQUENCE: 36

Ile Ala Cys Ile Met Ala Cys
1               5

<210> SEQ ID NO 37
<211> LENGTH: 9
<212> TYPE: PRT
<213> ORGANISM: Artificial sequence
<220> FEATURE:
<223> OTHER INFORMATION: Synthetic sequence: Target peptide sequence.

<400> SEQUENCE: 37

Ile Ile Thr Ala Cys Ile Met Ala Cys
1               5

<210> SEQ ID NO 38
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 38

Ala Thr Ala Cys Ile Thr Phe Cys
1               5

<210> SEQ ID NO 39
<211> LENGTH: 8
<212> TYPE: PRT
<213> ORGANISM: Artificial sequence
<220> FEATURE:
<223> OTHER INFORMATION: Synthetic sequence: Target peptide sequence.

<400> SEQUENCE: 39

Gly Val Ala Gly Ile Gly Phe Pro
1               5

<210> SEQ ID NO 40
<211> LENGTH: 29
<212> TYPE: PRT
<213> ORGANISM: Viola odorata

<400> SEQUENCE: 40

Gly Leu Pro Val Cys Gly Glu Thr Cys Val Gly Gly Thr Cys Asn Thr
1               5                   10                  15
```

```
Pro Gly Cys Thr Cys Ser Trp Pro Val Cys Thr Arg Asn
            20                  25
```

<210> SEQ ID NO 41
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 41

```
Gly Leu Glu Ala Ser
1               5
```

<210> SEQ ID NO 42
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 42

```
Gly Val Glu Pro Ser
1               5
```

<210> SEQ ID NO 43
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 43

```
Gly Val Glu Pro Pro
1               5
```

<210> SEQ ID NO 44
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 44

```
Gly Val Asp Ala Ser
1               5
```

<210> SEQ ID NO 45
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 45

```
Gly Val Gly Ala Ser
1               5
```

<210> SEQ ID NO 46
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 46

```
Gly Ala Gly Ala Ser
```

```
1               5

<210> SEQ ID NO 47
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 47

Gly Ala Glu Ala Ser
1               5

<210> SEQ ID NO 48
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 48

Gln Val Gln Ala Gln
1               5

<210> SEQ ID NO 49
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 49

Gln Val Glu Ala Gln
1               5

<210> SEQ ID NO 50
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 50

Gln Val Gln Ala Leu
1               5

<210> SEQ ID NO 51
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 51

Gln Val Thr Ala Gln
1               5

<210> SEQ ID NO 52
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 52

Gln Val Thr Ala His
1               5
```

```
<210> SEQ ID NO 53
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 53

Gln Val Thr Pro His
1               5

<210> SEQ ID NO 54
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 54

Gly Pro Gly Pro Ser
1               5

<210> SEQ ID NO 55
<211> LENGTH: 5
<212> TYPE: PRT
<213> ORGANISM: Artificial sequence
<220> FEATURE:
<223> OTHER INFORMATION: Synthetic sequence: Protease recognition SITE

<400> SEQUENCE: 55

Arg Val Thr Val Gln
1               5

<210> SEQ ID NO 56
<211> LENGTH: 6
<212> TYPE: PRT
<213> ORGANISM: Artificial sequence
<220> FEATURE:
<223> OTHER INFORMATION: Synthetic sequence: Heterologous protease SITE

<400> SEQUENCE: 56

Leu Val Pro Arg Gly Ser
1               5

<210> SEQ ID NO 57
<211> LENGTH: 7
<212> TYPE: PRT
<213> ORGANISM: Artificial sequence
<220> FEATURE:
<223> OTHER INFORMATION: Synthetic sequence: Heterologous protease SITE
<220> FEATURE:
<221> NAME/KEY: VARIANT
<222> LOCATION: (7)..(7)
<223> OTHER INFORMATION: Xaa is Gly or Ser

<400> SEQUENCE: 57

Glu Asn Leu Tyr Phe Gln Xaa
1               5

<210> SEQ ID NO 58
<211> LENGTH: 6
<212> TYPE: PRT
<213> ORGANISM: Artificial sequence
<220> FEATURE:
<223> OTHER INFORMATION: Synthetic sequence: Heterologous protease SITE

<400> SEQUENCE: 58
```

```
Glu Asn Leu Tyr Phe Gln
1               5

<210> SEQ ID NO 59
<211> LENGTH: 6
<212> TYPE: PRT
<213> ORGANISM: Artificial sequence
<220> FEATURE:
<223> OTHER INFORMATION: Synthetic sequence

<400> SEQUENCE: 59

Gly Leu Glu Ala Ser Lys
1               5

<210> SEQ ID NO 60
<211> LENGTH: 11
<212> TYPE: PRT
<213> ORGANISM: Artificial sequence
<220> FEATURE:
<223> OTHER INFORMATION: Synthetic sequence

<400> SEQUENCE: 60

Gly Leu Glu Ala Ser Glu Asn Leu Tyr Phe Gln
1               5                   10

<210> SEQ ID NO 61
<211> LENGTH: 10
<212> TYPE: PRT
<213> ORGANISM: Artificial sequence
<220> FEATURE:
<223> OTHER INFORMATION: Synthetic sequence: Purification tag

<400> SEQUENCE: 61

Met Arg Gly Ser His His His His His His
1               5                   10

<210> SEQ ID NO 62
<211> LENGTH: 8
<212> TYPE: PRT
<213> ORGANISM: Artificial sequence
<220> FEATURE:
<223> OTHER INFORMATION: Synthetic sequence: FLAG Purification tag

<400> SEQUENCE: 62

Asp Tyr Lys Asp Asp Asp Asp Lys
1               5

<210> SEQ ID NO 63
<211> LENGTH: 15
<212> TYPE: PRT
<213> ORGANISM: Artificial sequence
<220> FEATURE:
<223> OTHER INFORMATION: Synthetic sequence: Purification tag

<400> SEQUENCE: 63

Lys Glu Thr Ala Ala Ala Lys Phe Glu Arg Gln His Met Asp Ser
1               5                   10                  15

<210> SEQ ID NO 64
<211> LENGTH: 8
<212> TYPE: PRT
<213> ORGANISM: Artificial sequence
<220> FEATURE:
<223> OTHER INFORMATION: Synthetic sequence: Strept-tag II purification
      tag

<400> SEQUENCE: 64
```

```
Trp Ser His Pro Gln Phe Glu Lys
1               5

<210> SEQ ID NO 65
<211> LENGTH: 10
<212> TYPE: PRT
<213> ORGANISM: Artificial sequence
<220> FEATURE:
<223> OTHER INFORMATION: Synthetic sequence: c-myc purification tag

<400> SEQUENCE: 65

Glu Gln Lys Leu Ile Ser Glu Glu Asp Leu
1               5                   10

<210> SEQ ID NO 66
<211> LENGTH: 12
<212> TYPE: PRT
<213> ORGANISM: Artificial sequence
<220> FEATURE:
<223> OTHER INFORMATION: Synthetic sequence: Cruz tag 09

<400> SEQUENCE: 66

Met Lys Ala Glu Phe Arg Arg Gln Glu Ser Asp Arg
1               5                   10

<210> SEQ ID NO 67
<211> LENGTH: 12
<212> TYPE: PRT
<213> ORGANISM: Artificial sequence
<220> FEATURE:
<223> OTHER INFORMATION: Synthetic sequence: Cruz tag 22

<400> SEQUENCE: 67

Met Arg Asp Ala Leu Asp Arg Leu Asp Arg Leu Ala
1               5                   10

<210> SEQ ID NO 68
<211> LENGTH: 12
<212> TYPE: PRT
<213> ORGANISM: Artificial sequence
<220> FEATURE:
<223> OTHER INFORMATION: Synthetic sequence

<400> SEQUENCE: 68

Val Gly Ala Gly Ile Gly Phe Pro Ala Tyr Asp Gly
1               5                   10

<210> SEQ ID NO 69
<211> LENGTH: 12
<212> TYPE: PRT
<213> ORGANISM: Artificial sequence
<220> FEATURE:
<223> OTHER INFORMATION: Synthetic sequence: Peptide substrate

<400> SEQUENCE: 69

Val Gly Ala Gly Ile Gly Phe Pro Ala Tyr Arg Gly
1               5                   10

<210> SEQ ID NO 70
<211> LENGTH: 8
<212> TYPE: PRT
<213> ORGANISM: Artificial sequence
<220> FEATURE:
<223> OTHER INFORMATION: Synthetic sequence

<400> SEQUENCE: 70
```

Val Gly Ala Gly Ile Gly Phe Pro
1               5

<210> SEQ ID NO 71
<211> LENGTH: 61
<212> TYPE: PRT
<213> ORGANISM: Artificial sequence
<220> FEATURE:
<223> OTHER INFORMATION: Synthetic sequence: Engineered PatE
      pre-pro-peptide

<400> SEQUENCE: 71

Met Asp Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Ile Thr Ala Cys Ile Thr
        35                  40                  45

Phe Cys Ala Tyr Asp Gly Glu His His His His His His
    50                  55                  60

<210> SEQ ID NO 72
<211> LENGTH: 62
<212> TYPE: PRT
<213> ORGANISM: Artificial sequence
<220> FEATURE:
<223> OTHER INFORMATION: Synthetic sequence: Engineered PatE
      pre-pro-peptide

<400> SEQUENCE: 72

Met Asp Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Lys Ile Thr Ala Cys Ile
        35                  40                  45

Thr Phe Cys Ala Tyr Asp Gly Glu His His His His His His
    50                  55                  60

<210> SEQ ID NO 73
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (2, 6)
<223> OTHER INFORMATION: Xaa is MeOxn
<220> FEATURE:
<221> NAME/KEY: SITE
<222> LOCATION: (4, 8)
<223> OTHER INFORMATION: Xaa is Thn

<400> SEQUENCE: 73

Ile Xaa Ala Xaa Ile Xaa Phe Xaa
1               5

<210> SEQ ID NO 74
<211> LENGTH: 8
<212> TYPE: PRT
<213> ORGANISM: Artificial sequence
<220> FEATURE:
<223> OTHER INFORMATION: Synthetic sequence: Cassette

<400> SEQUENCE: 74

```
Ile Thr Phe Cys Ile Thr Ala Cys
1               5
```

<210> SEQ ID NO 75
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (4, 8)
<223> OTHER INFORMATION: Xaa is Thn

<400> SEQUENCE: 75

```
Ile Thr Phe Xaa Ile Thr Ala Xaa
1               5
```

<210> SEQ ID NO 76
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (2, 6)
<223> OTHER INFORMATION: Xaa is MeOxn
<220> FEATURE:
<221> NAME/KEY: SITE
<222> LOCATION: (4, 8)
<223> OTHER INFORMATION: Xaa is Thn

<400> SEQUENCE: 76

```
Ile Xaa Val Xaa Ile Xaa Val Xaa
1               5
```

<210> SEQ ID NO 77
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (4, 8)
<223> OTHER INFORMATION: Xaa is Thn

<400> SEQUENCE: 77

```
Ile Thr Ala Xaa Ile Thr Phe Xaa
1               5
```

<210> SEQ ID NO 78
<211> LENGTH: 71
<212> TYPE: PRT
<213> ORGANISM: Prochloron didemni

<400> SEQUENCE: 78

```
Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Val Thr Ala Cys Ile Thr
        35                  40                  45

Phe Cys Ala Tyr Asp Gly Val Glu Pro Ser Ile Thr Val Cys Ile Ser
    50                  55                  60
```

Val Cys Ala Tyr Asp Gly Glu
65                  70

<210> SEQ ID NO 79
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (4, 8)
<223> OTHER INFORMATION: Xaa is Thn

<400> SEQUENCE: 79

Ile Thr Val Xaa Ile Thr Val Xaa
1               5

<210> SEQ ID NO 80
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: SITE
<222> LOCATION: (2, 6)
<223> OTHER INFORMATION: Xaa is MeOxz
<220> FEATURE:
<221> NAME/KEY: SITE
<222> LOCATION: (4, 8)
<223> OTHER INFORMATION: Xaa is Thz

<400> SEQUENCE: 80

Ile Xaa Val Xaa Ile Xaa Val Xaa
1               5

<210> SEQ ID NO 81
<211> LENGTH: 8
<212> TYPE: PRT
<213> ORGANISM: Artificial sequence
<220> FEATURE:
<223> OTHER INFORMATION: Synthetic sequence: Cyclic peptide

<400> SEQUENCE: 81

Val Gly Ile Cys Ala Gly Phe Pro
1               5

<210> SEQ ID NO 82
<211> LENGTH: 12
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (8)..(8)
<223> OTHER INFORMATION: Dpr

<400> SEQUENCE: 82

Ile Thr Ala Ser Ile Thr Phe Ser Ala Tyr Asp Gly
1               5                   10

<210> SEQ ID NO 83
<211> LENGTH: 6
<212> TYPE: PRT
<213> ORGANISM: Artificial sequence
<220> FEATURE:
<223> OTHER INFORMATION: Synthetic sequence: Additional residues
      allowing cleavage by Tobacco etch virus (TEV) protease

<400> SEQUENCE: 83

Glu Asn Leu Tyr Phe Gln
1               5

<210> SEQ ID NO 84
<211> LENGTH: 12
<212> TYPE: PRT
<213> ORGANISM: Artificial sequence
<220> FEATURE:
<223> OTHER INFORMATION: Synthetic sequence

<400> SEQUENCE: 84

Gly Val Ala Gly Ile Gly Phe Pro Ala Tyr Arg Gly
1               5                   10

<210> SEQ ID NO 85
<211> LENGTH: 12
<212> TYPE: PRT
<213> ORGANISM: Artificial sequence
<220> FEATURE:
<223> OTHER INFORMATION: Synthetic sequence

<400> SEQUENCE: 85

Val Pro Ala Pro Ile Pro Phe Pro Ala Tyr Asp Gly
1               5                   10

<210> SEQ ID NO 86
<211> LENGTH: 9
<212> TYPE: PRT
<213> ORGANISM: Artificial sequence
<220> FEATURE:
<223> OTHER INFORMATION: Synthetic sequence

<400> SEQUENCE: 86

Pro Ile Pro Phe Pro Ala Tyr Asp Gly
1               5

<210> SEQ ID NO 87
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (4, 8)
<223> OTHER INFORMATION: Xaa is Thn

<400> SEQUENCE: 87

Ile Thr Ala Xaa Ile Thr Tyr Xaa
1               5

<210> SEQ ID NO 88
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (2, 6)
<223> OTHER INFORMATION: Xaa is MeOxn
<220> FEATURE:
<221> NAME/KEY: SITE
<222> LOCATION: (4, 8)
<223> OTHER INFORMATION: Xaa is Thn

<400> SEQUENCE: 88

```
Ile Xaa Ala Xaa Ile Xaa Tyr Xaa
1               5

<210> SEQ ID NO 89
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (4, 8)
<223> OTHER INFORMATION: Xaa is Thn

<400> SEQUENCE: 89

Ile Met Ala Xaa Ile Met Ala Xaa
1               5

<210> SEQ ID NO 90
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (4, 8)
<223> OTHER INFORMATION: Xaa is Thn

<400> SEQUENCE: 90

Ile Asp Ala Xaa Ile Asp Phe Xaa
1               5

<210> SEQ ID NO 91
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (4, 8)
<223> OTHER INFORMATION: Xaa is Thn

<400> SEQUENCE: 91

Val Thr Val Xaa Val Thr Val Xaa
1               5

<210> SEQ ID NO 92
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (2, 6)
<223> OTHER INFORMATION: Xaa is MeOxn
<220> FEATURE:
<221> NAME/KEY: SITE
<222> LOCATION: (4, 8)
<223> OTHER INFORMATION: Xaa is Thn

<400> SEQUENCE: 92

Val Xaa Val Xaa Val Xaa Val Xaa
1               5

<210> SEQ ID NO 93
<211> LENGTH: 8
```

```
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (4, 8)
<223> OTHER INFORMATION: Xaa is Sen

<400> SEQUENCE: 93

Ile Thr Ala Xaa Ile Thr Phe Xaa
1               5

<210> SEQ ID NO 94
<211> LENGTH: 6
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (2, 6)
<223> OTHER INFORMATION: Xaa is Thn

<400> SEQUENCE: 94

Ala Xaa Ile Met Ala Xaa
1               5

<210> SEQ ID NO 95
<211> LENGTH: 7
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (3, 7)
<223> OTHER INFORMATION: Xaa is Thn

<400> SEQUENCE: 95

Ile Ala Xaa Ile Met Ala Xaa
1               5

<210> SEQ ID NO 96
<211> LENGTH: 9
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (5, 9)
<223> OTHER INFORMATION: Xaa is Thn

<400> SEQUENCE: 96

Ile Ile Thr Ala Xaa Ile Met Ala Xaa
1               5

<210> SEQ ID NO 97
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (2, 4, 8)
<223> OTHER INFORMATION: Xaa is Thn

<400> SEQUENCE: 97
```

Ile Xaa Ala Xaa Ile Thr Phe Xaa
1               5

<210> SEQ ID NO 98
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (4, 8)
<223> OTHER INFORMATION: Xaa is Thn

<400> SEQUENCE: 98

Ile Ala Ala Xaa Ile Thr Phe Xaa
1               5

<210> SEQ ID NO 99
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (4, 8)
<223> OTHER INFORMATION: Xaa is Thn

<400> SEQUENCE: 99

Ile Thr Ala Xaa Ile Thr Ala Xaa
1               5

<210> SEQ ID NO 100
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (4, 8)
<223> OTHER INFORMATION: Xaa is Thn

<400> SEQUENCE: 100

Ala Thr Ala Xaa Ile Thr Phe Xaa
1               5

<210> SEQ ID NO 101
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:
<221> NAME/KEY: SITE
<222> LOCATION: (8)..(8)
<223> OTHER INFORMATION: Xaa is Thn

<400> SEQUENCE: 101

Ile Thr Ala Ala Ile Thr Phe Xaa
1               5

<210> SEQ ID NO 102
<211> LENGTH: 8
<212> TYPE: PRT
<213> ORGANISM: Artificial sequence
<220> FEATURE:
<223> OTHER INFORMATION: Synthetic sequence: Cyclic peptide
<220> FEATURE:

```
<221> NAME/KEY: SITE
<222> LOCATION: (4, 8)
<223> OTHER INFORMATION: Xaa is Thn

<400> SEQUENCE: 102

Ile Thr Ala Xaa Ile Ser Phe Xaa
1               5

<210> SEQ ID NO 103
<211> LENGTH: 8
<212> TYPE: PRT
<213> ORGANISM: Artificial sequence
<220> FEATURE:
<223> OTHER INFORMATION: Synthetic sequence: Core peptide sequence of
      PatE mutant C51P

<400> SEQUENCE: 103

Ile Thr Ala Cys Ile Thr Phe Pro
1               5

<210> SEQ ID NO 104
<211> LENGTH: 8
<212> TYPE: PRT
<213> ORGANISM: Artificial sequence
<220> FEATURE:
<223> OTHER INFORMATION: Synthetic sequence: Core peptide sequence of
      PatE mutant C51A

<400> SEQUENCE: 104

Ile Thr Ala Cys Ile Thr Phe Ala
1               5

<210> SEQ ID NO 105
<211> LENGTH: 5
<212> TYPE: PRT
<213> ORGANISM: Artificial sequence
<220> FEATURE:
<223> OTHER INFORMATION: Synthetic sequence: Cleavage recognition
      sequence
<220> FEATURE:
<221> NAME/KEY: VARIANT
<222> LOCATION: (2)..(2)
<223> OTHER INFORMATION: Xaa is Leu or Val
<220> FEATURE:
<221> NAME/KEY: VARIANT
<222> LOCATION: (4)..(4)
<223> OTHER INFORMATION: Xaa is Ala or Pro

<400> SEQUENCE: 105

Gly Xaa Glu Xaa Ser
1               5

<210> SEQ ID NO 106
<211> LENGTH: 4
<212> TYPE: PRT
<213> ORGANISM: Artificial sequence
<220> FEATURE:
<223> OTHER INFORMATION: Synthetic sequence: Heterologous protease SITE
<220> FEATURE:
<221> NAME/KEY: VARIANT
<222> LOCATION: (2)..(2)
<223> OTHER INFORMATION: Xaa is Glu or Asp

<400> SEQUENCE: 106

Ile Xaa Gly Arg
1
```

IN VITRO PRODUCTION OF CYCLIC PEPTIDES

CROSS REFERENCE TO RELATED APPLICATIONS

This application is a continuation of U.S. Ser. No. 14/410,939, filed Dec. 23, 2014, which is the national stage of International (PCT) Patent Application No. PCT/GB2013/051735, filed Jun. 28, 2013, and published under PCT Article 21(2) in English, which claims the benefit of and priority to GB Application No. 1211617.4, filed Jun. 29, 2012, the entire contents of each of which are incorporated by reference herein.

This invention relates to methods for the production of cyclic peptides in vitro.

Cyclic peptides have long been of interest to the biotechnology and pharmaceutical industries for use as novel medicines. They are considerably more stable compounds than linear peptides and can cross cell membranes more efficiently, which makes them ideal drug molecules (Driggers, E. M. et al. *Nat Rev Drug Discov* 7, 608-624 (2008))). Cyclic peptides are particularly challenging to produce synthetically. Marine cyanobacteria have been shown to produce cyclic peptide natural products, the cyanobactins (Sivonen et al., 2010, Appl Microbiol Biotechnol, 86, 1213-25; See FIGS. 1(*a*) and (*b*) for a range of example cyclic peptide structures). They are produced through ribosomal biosynthetic pathways where a pre-pro-peptide undergoes multiple post-translational modifications including heterocyclisation of amino acids, epimerization, prenylation and geranylation, (Donia et al, 2006, Nat Chem Biol, 2, 729-35).

Patellamides, members of the cyanobactin superfamily, are produced by *Prochloron* spp., an obligate, uncultured symbiont of the sea squirt *Lissoclinum patella* (Schmidt et al., 2005, Proc Natl Acad Sci USA, 102, 7315-20; Long et al. 2005, Chembiochem, 6, 1760-5). These compounds show cytotoxicity (Kohda et al., 1989, Biochem Pharmacol, 38, 4497-500) and the ability to reverse multiple drug resistance in human leukemia cells (Williams and Jacobs, 1993, Cancer Lett, 71, 97-102). Patellamides are cyclic octapeptides containing heterocyclized residues (Ser/Thr, Cys) giving oxazolines and thiazolines, which can be further oxidized to thiazoles (Schmidt et al., 2005, Proc Natl Acad Sci USA, 102, 7315-20).

The Patellamide gene cluster has been identified and the genes patA, D, E, F, and G have been reported to be essential to yield products (Donia et al., 2008, Nat Chem Biol, 4, 341-3; Donia et al., 2006, Nat Chem Biol, 2, 729-35). PatE, the pre-pro-peptide, consists of 37-residue leader sequence (containing a single helix from residues 13-28 {Houssen, W. E. et al.—Chembiochem 11, 1867-1873}), and one, two or three cassettes of eight residues, which are each flanked by N- and C-terminal protease recognition sites and go on to form the final product {Schmidt et al., 2005, Proc Natl Acad Sci USA, 102, 7315-20}.

Several steps in the synthesis of patellamides have been fully characterised. Heterocyclization of specific amino acids must come before N- and C-terminal cleavage, with macrocyclisation being the final step to product. It is still unclear at what stage epimerization, oxidation of thiazolines to thiazoles, and prenylation and/or geranylation occur but epimerisation has been reported to be spontaneous and occurs after macrocyclisation. Oxidation must be last. (Milne, B. F. et al *Org Biomol Chem* 4, 631-638 (2006)). This application focuses on the heterocyclisation, cassette cleavage and macrocyclization steps.

Heterocyclization is the first step in PatE pre-pro-peptide tailoring and catalyzed by the three-domain protein PatD. PatD contains substrate specificity for the 37 amino acid leader sequence of PatE and heterocyclises cysteine and threonine/serine residues to form thiazolines and oxazolines respectively. This process results in the loss of one water molecule per heterocycle. TruD, a PatD homolog from the trunkamide pathway has been shown to heterocyclize cysteine residues only (McIntosh, J. A. et al (2010). Chembiochem 11(10): 1413-1421).

The N-terminal cleavage of the cassette is catalyzed by PatA, a two-domain protein consisting of an N-terminal subtilisin-like protease domain and a C-terminal domain of unknown function (DUF). The protease domain (PatApr) acts on the cleavage recognition sequence 'G(L/V)E(A/P)S'(SEQ ID NO: 105), with the first residue of the cassette in the P1' position. {Lee et al., 2009, J. Am. Chem. Soc., 131, 2122-2124}.

The final step of patellamide production is C-terminal cleavage and macrocyclisation. This step is catalysed by PatG, a three-domain protein consisting of an N-terminal oxidase domain, a subtilisin-like protease/macrocyclase domain and a C-terminal DUF. The protease/macrocyclase domain (PatGmac) is responsible for both cleavage of the C-terminus of the cassette and for macrocyclizing the cleaved cassette into a patellamide. {Lee et al. 2009 J. Am. Chem. Soc., 131, 2122-2124} PatGmac recognises the sequence XAYDG (SEQ ID NO: 6), where X is the final residue in the cassette, located in the P1 position. {McIntosh et al., 2010, J Am Chem Soc, 132, 15499-501} It has been reported previously that the final residue of the cassette must be a Pro or heterocycle {McIntosh et al., 2010, J Am Chem Soc, 132, 15499-501}.

Previous in vivo studies of the pathway have shown that cyclic products yields of up to 320 µg/L can be produced (Tianero M D et al. JACS (2012) 418-425).

This invention relates to the development and optimisation of in vitro methods for the production of cyclic peptides using cyanobacterial enzymes, such as patellamide biosynthesis enzymes. This may be useful, for example, for the production of peptidyl molecules, the biosynthesis and screening of candidate therapeutics, and nanotechnology applications.

An aspect of the invention provides an in vitro method of producing a cyclic peptide comprising;
(i) providing a linear peptide substrate; and,
(ii) treating said peptide substrate with an isolated cyanbacterial macrocyclase to produce a cyclic peptide.

Cyclic peptides are circularised peptidyl compounds which include cyclotides and cyanobactins, for example patellamides and telomestatins.

Patellamides are cyclic octapeptides produced by *Prochloron* spp which include patellamide A, B, C and D.

A cyanobacterial macrocyclase is a cyanobacterial enzyme which catalyses the cyclisation of peptide substrates which contain a cyclisation signal.

Suitable cyanobacterial macrocyclases include PatG macrocyclase (AAY21156.1 GI:62910843; residues 492-851 of SEQ ID NO: 1) and TruG (gi|167859101|gb|ACA04494.1) from *Prochloron* and macrocylases from *Anabaena* spp, such as ADA00395.1 GI:280987232; ACK37889.1 GI:217316956 and AED99446.1 GI:332002633; *Oscillatoria* sp, such as GI:300866529 ZP_07111219.1; *Microcystis* spp such as GI:389832527 CCI23764.1, GI:158934376 CAO82089.1, GI:389788443 CCI15902.1, GI:389678154 CCH92964.1, GI:389802072 CCI18832.1, GI:389882395 CCI37144.1, GI:389826370 CCI23111.1; GI:389731219

CCI04703.1, GI:389716328 CCH99432.1, GI:389831597 CCI25524.1 and GI:159027550 CAO86920.1; *Nostoc spongiaeforme* spp, such as TenG (GI:167859092 ACA04486.1); *lyngya* spp, such as GI:119492374 ZP_01623710.1; *Nodularia* spp, such as GI:119512474 ZP_01631555.1; *Anabaena* spp, such as AcyG (GI:280987232 ADA00395.1) *Planktothrix* spp, such as GI:332002633 AED99446.1, *Trichodesmium* spp, such as GI:113475997 YP_722058.1; and *Arthrospira* spp, such as ZP_06384654.1 GI:284054444, GI:284054071 ZP_06384281.1, GI:291571075 BAI93347.1, GI:284054444 ZP_06384654.1, and GI:376002294 ZP_09780130.1. The sequence alignment of FIGS. 1A and 1B provides the sequences of other suitable cyanobacterial macrocyclases.

Other suitable cyanobacterial macrocyclases are available in the art (Lee, S. W. et al (2008). Discovery of a widely distributed toxin biosynthetic gene cluster, PNAS 105(15), 5879-5884).

A cyanobacterial macrocyclase may comprise the amino acid sequence of any one of the above reference cyanobacterial macrocyclase sequences or may be a variant thereof. For example, a cyanobacterial macrocyclase may be a PatG macrocyclase which comprises the amino acid sequence of residues 492-851 of SEQ ID NO: 1 or other macrocyclase shown in FIGS. 1A and 1B or which comprises an amino acid sequence which is a fragment or variant thereof.

In some embodiments, a PatG macrocyclase may comprise the sequence of SEQ ID NO: 1 with 1, 2, 3, 4, 5, 6, 7, 8, 9, 10 or more residues inserted, deleted or substituted. For example, up to 15, up to 20, up to 30, up to 40, up to 50, or up to 60 residues may be inserted, deleted or substituted. Suitable residues for substitution include R589, K594, K598 and H746.

The position in a cyanobacterial macrocyclase which corresponds to position R589, K594, K598, H746 or other position of the PatG sequence of SEQ ID NO: 1 may be readily determined using routine sequence analysis techniques. The amino acid at this position may be replaced by a different amino acid residue using routine site-directed mutagenesis techniques (see for example, *Molecular Cloning: a Laboratory Manual:* 3rd edition, Russell et al. (2001) Cold Spring Harbor Laboratory Press).

Fragments and variants of a reference sequence are described elsewhere herein. In some embodiments, a cyanobacterial macrocyclase which comprises a sequence which is a variant of one of the above reference sequences may comprise Asp, His and Ser residues at positions equivalent to Asp548, His618 and Ser783 in SEQ ID NO: 1.

A cyanobacterial macrocyclase which comprises a sequence which is a variant of one of the above reference sequences may comprise the residues shown in black in a macrocyclase sequence shown in the alignment of FIGS. 1A and 1B in an equivalent position in the variant sequence.

In some embodiments, the cyanobacterial macrocyclase may comprise a modified recognition sequence which recognises a modified cyclisation signal. The recognition sequence in the macrocyclase and the cyclisation signal in the peptide substrate may be modified such that they are complementary and binding between macrocyclase and substrate occurs. For example, one of the macrocyclase and the cyclisation signal may be a positive sequence, such as RRR or KKK, and the other may be a negative sequence, such as DDD or EEE. In some embodiments, the cyanobacterial macrocyclase may comprise the recognition sequence RKK which recognises the cyclisation sequence AYDG (SEQ ID NO: 20).

In some embodiments, the cyanobacterial macrocyclase may comprise a substitution at the residue equivalent to H746 and/or F747 of SEQ ID NO: 1. These residues interact with the Y of the cyclisation signal AYD. For example, substituting F747 to a charged residue in the macrocyclase may allow substitution of Y for residue with opposite charge in the cyclisation signal.

In some embodiments, the cyanobacterial macrocyclase may comprise a substitution at the residue equivalent to K598 of SEQ ID NO: 1. For example, the cyanobacterial macrocyclase may comprise a K598D substitution and may recognise the cyclisation signal AYR.

Modification of the cyanobacterial macrocyclase sequence, for example by a R589, K594, K598 and H746 or other substitution or equivalents, may have improved activity and/or kinetics over the native enzyme sequence. This may be helpful in making the biosynthetic process viable in a reasonable time.

Modification of the cyanobacterial macrocyclase sequence to recognise a modified cyclisation sequence may be required if the target peptide sequence for cyclisation contains an unmodified cyclisation sequence (e.g. XAYD, where X is a heterocycle or Pro).

The peptide substrate may comprise a target peptide and a C terminal cyclisation signal.

The target peptide is the sequence which undergoes cyclisation by the macrocyclase to form the cyclic peptide.

A suitable target peptide may have at least 4, 5, 6, 7 or 8 residues.

A suitable target peptide may have up to 11, 12, 13, 14, 15, 16, 17, 18, 19, 20, 21, 22, 23, 24, 25, 26, 27, 28, 29 or 30 or more residues. For example, a suitable target peptide may have from 4 to 30 residues, preferably 4 to 23 residues, more preferably 6 to 23, 6 to 20 or 6 to 11 residues.

The target peptide sequence may be natural e.g. a natural cyanobactin sequence or a precursor thereof; or a natural cyclotide sequence or a precursor thereof; or the target peptide sequence may be synthetic. For example, the target peptide sequence may be a heterologous sequence which is not normally associated with a cyanobactin cyclisation signal.

The target peptide may include modified amino acids, unmodified amino acids, heterocyclic amino acids, non-heterocyclic amino acids, naturally occurring amino acids and/or non-naturally occurring amino acids. Methods of the invention also provide the introduction of heterocyclic amino acids into the target peptide sequence using isolated cyanobacterial enzymes, as described below, and optionally the oxidation of the introduced heterocyclic amino acids.

A target peptide sequence may comprise 0, 1, 2, 3, 4, 5, 6, 7, 8 or more heterocyclic amino acids (Shin-ya, K. et al J. Am. Chem. Soc. 2001, 123, 1262-1263).

Preferably, the residue directly N terminal to the cyclisation signal in the target peptide sequence is a heterocyclic amino acid. For example, an amino acid selected from thiazoline (Thn), thiazole (Thz), oxazoline (Oxn), oxazole (Oxz), proline and pseudoproline (Pro).

In other embodiments, the residue directly N terminal to the cyclisation signal in the target peptide sequence may be an N-methylated amino acid or a moiety with an NH2 and COOH group which allows the target peptide sequence to bend sufficiently for macrocyclisation.

Suitable target peptide sequences include ITACITFC (SEQ ID NO: 21); ITACISFC (SEQ ID NO: 22); ICACITFC (SEQ ID NO: 23); IAACITFC (SEQ ID NO: 24); ITACITYC (SEQ ID NO: 25); ITACITAC (SEQ ID NO: 26); ITA(SeCys)ITF(SeCys) (SEQ ID NO: 27); IMACIMAC (SEQ ID NO: 28); IDACIDFC (SEQ ID NO: 29); ITVCITVC (SEQ ID NO: 30); ITAAITFC (SEQ ID NO: 31); VPAPIPFP (SEQ ID NO: 32); VTVCVTVC (SEQ ID NO: 33); VGAGIGFP (SEQ ID NO: 34); ACIMAC (SEQ ID NO: 35); IACIMAC (SEQ ID NO: 36); IITACIMAC (SEQ ID NO: 37); ATACITFC (SEQ ID NO: 38) and GVAGIGFP (SEQ ID NO: 39). Other suitable target peptide sequences, for example cyanobactins or other cyclic and macrocyclic peptides, are well-known in the art (see for example Houssen, W. E. & Jaspars, M. *Chembiochem* 11, 1803-1815 (2010); Sivonen, K., et al (2010) *Applied Microbiology*, (86) 1213-1225) and/or described elsewhere herein.

Other suitable target peptide sequences include cyclotide sequences, such as GLPVCGETCVGGTCNTPGCTC-SWPVCTRN (Kalata B1) (SEQ ID NO: 40).

In some embodiments, one or more residues in the target peptide sequence may comprise a reactive functionality which may allow further chemical modification. Suitable residues may contain side chains with side chain linking groups such as NH2, COOH, OH and SH.

The cyclisation signal is located at the C terminal of the peptide substrate, preferably adjacent the target peptide. The cyclisation signal is the recognition site for the cyanobacterial macrocyclase. The sequence of the cyclisation signal in a peptide substrate may depend on the cyanobacterial macrocyclase being used. Typically, a cyclisation signal will comprise the sequence; small residue—bulky residue—acidic residue. Suitable cyclisation signals include AYD, AYE, SYD, AFD and FAG.

In some preferred embodiments, the cyanobacterial macrocyclase is a PatG macrocyclase and the cyclisation signal is AYD.

In some embodiments, the cyclisation signal may be heterologous i.e. not naturally associated with the target peptide sequence.

The cyclisation signal may be a natural cyclisation signal or a synthetic or modified cyclisation signal. A modified cyclisation signal may be recognised by a modified cyanobacterial macrocyclase, as described above.

The linear peptide substrate may be treated with the cyanobacterial macrocyclase under suitable conditions for the cyclisation of peptide. Suitable conditions would be apparent to those skilled in the art. In some preferred embodiments, conditions may include 500 mM NaCl and/or pH 9. For example, the linear peptide substrate may be treated with the cyanobacterial macrocyclase in 500 mM NaCl and 5% DMSO at pH 8.

The highest temperature tolerated by the macrocylase is generally preferred as this leads to increased reaction rates. The optimal temperature for reaction under a defined set of conditions may be determined experimentally.

In some embodiments, the linear peptide substrate may be immobilised, for example on a solid support, and the cyanobacterial macrocyclase may be free in solution. This may be useful, for example in facilitating purification of the cyclic peptide.

In other embodiments, the linear peptide substrate may be free in solution and the cyanobacterial macrocyclase may be immobilised for example on a solid support, such as a bead. This may be useful, for example in facilitating re-cycling of the macrocyclase.

In some embodiments, a linear peptide substrate may be produced, for example by chemical synthesis or recombinant means as described below, and treated directly with the cyanobacterial macrocyclase. This may be useful in producing cyclic peptides which do not contain heterocycles.

In other embodiments, the linear peptide substrate may be produced from a pro-peptide. For example, the linear peptide substrate may be provided by a method comprising;
  (i) providing a linear pro-peptide; and,
  (ii) treating said linear pro-peptide with an isolated protease to produce the linear peptide substrate.

The linear pro-peptide may comprise the linear peptide substrate linked to a pro-sequence, for example an N terminal leader sequence, by a protease recognition site.

In some embodiments, the protease recognition site may be G(L/V)E(A/P)S (SEQ ID NO: 105) and the protease may be a cyanobacterial protease, such as a PatA protease. Other suitable protease recognition sites include GAEAS (SEQ ID NO: 41), GVEPS (SEQ ID NO: 42), GVEPP (SEQ ID NO: 43), GVDAS (SEQ ID NO: 44), GVGAS (SEQ ID NO: 45), GAGAS (SEQ ID NO: 46), GAEAS (SEQ ID NO: 47), QVTAQ (SEQ ID NO: 48), QVEAQ (SEQ ID NO: 49), QVQAL (SEQ ID NO: 50), QVTAQ (SEQ ID NO: 51), QVTAH (SEQ ID NO: 52), QVTPH (SEQ ID NO: 53), GPGPS (SEQ ID NO: 54) and RVTVQ (SEQ ID NO: 55).

A cyanobacterial protease is an enzyme from a cyanobacterium which cleaves a peptide chain at a protease recognition site.

Suitable cyanobacterial proteases include PatA protease (AAY21150.1 GI:62910837), TruA protease (ACA04487.1 GI:167859094) from *Prochloron* spp and proteases from *Lyngbya* sp, such as ZP_01623699.1 GI:119492363; *Microcystis* spp, such as CAO086912.1 GI:159027542; and CAO82081.1 GI:158934368; *Nostoc spongiaeforme* spp, such as TenA (ACA04480.1 GI:167859086); *Anabaena* spp, such as AcyA (ACK37888.2 GI:280987221), *Oscillatoria* sp such as ZP_07111214.1 GI:300866524; *Trichodesmium* spp, such as YP_722055.1 GI:113475994; *Nodularia* spp, such as ZP_01631559.1 GI:119512478; *Cyanothece* spp, such as YP_003900371.1 GI:307591572 and YP_002481258.1 GI:220905947; and *Arthrospira* spp, such as BAI93369.1 GI:291571097. Other suitable cyanobacterial proteases are shown in Table 4.

A cyanobacterial protease may comprise the amino sequence of any one of the above reference cyanobacterial protease sequences or may be a variant thereof. For example, a cyanobacterial protease may be a PatA protease which comprises the amino sequence of SEQ ID NO: 2 or is a variant thereof. Variants of a reference sequence are described elsewhere herein.

In some embodiments, the cyanobacterial protease may comprise a modified sequence which recognises a modified and/or heterologous protease recognition site. The protease sequence and the protease recognition site in the peptide substrate may be modified such that they are complementary and binding occurs.

In more preferred embodiments, the pro-peptide may further comprise a heterologous protease recognition site and the protease may be a heterologous protease.

For example, the heterologous protease recognition site may be a K or R residue and the protease may be trypsin; the heterologous protease site may be Y and the protease may be chymotrypsin; the heterologous protease site may be LVPRGS (SEQ ID NO: 56) and the protease may be thrombin; the heterologous protease site may be I(E/D)GR (SEQ ID NO: 106) and the protease may be factor Xa; or the heterologous protease site may be ENLYFQ(G/S) (SEQ ID NO: 57) or ENLYFQ (SEQ ID NO: 58) and the protease may be Tobacco Etch Virus (TEV) protease. Other suitable site specific proteases are well-known in the art and any site specific endoprotease with a residue preference may be used.

For example, GluC cuts after E, so replacing K or R in the heterologous protease recognition site with E would allow cleavage by GluC.

Heterologous site-specific proteases, such as TEV protease, trypsin and chymotrypsin are well known in the art and are available from commercial sources.

The cyanobacterial protease recognition site may also be a recognition site for the cyanobacterial heterocyclase. When a heterologous protease recognition site is present, the cyanobacterial protease recognition site may be retained in order to allow the introduction of heterocycles into the target peptide sequence, as described below. For example, a linear pro-peptide may comprise the sequence GLEASK (SEQ ID NO: 59) [peptide sequence] or GLEASENLYFQ (SEQ ID NO: 60) [peptide sequence].

In embodiments in which heterocycles are not introduced into the target peptide sequence, the pro-peptide may lack a cyanobacterial protease recognition site.

In some embodiments, the linear pro-peptide comprises one, two, three or more peptide substrates linked by protease recognition sites. Treatment of the linear pro-peptide with the protease releases the one, two, three or more linear peptide substrates from the pro-peptide. The releases of two, three or more peptide substrates in the linear pro-peptide may be the same or different.

In some embodiments, the pro-peptide may be immobilised and the protease may be free in solution. This may be useful, for example, in facilitating purification of the peptide substrate, for example before cyclisation.

In other embodiments, the pro-peptide may be free in solution and the protease may be immobilised. This may be useful, for example, in facilitating re-cycling of the protease.

Before cyclisation and optionally proteolysis, the linear peptide substrate or pro-peptide may be treated to heterocyclise amino acid residues in the target peptide sequence. For example, the linear peptide substrate or the linear pro-peptide may be provided by a method comprising;
  (i) providing a pre-pro-peptide comprising one or more heterocyclisable amino acids;
  (ii) treating said linear pre-pro-peptide with a cyanobacterial heterocyclase to convert the heterocyclisable amino acids into heterocyclic residues,
    thereby producing the linear peptide substrate or the pro-peptide.

Heterocyclisable amino acids include cysteine, selenocysteine, tellurocysteine, threonine, serine, 2,3-diaminopropanoic acid and synthetic derivatives thereof with additional R groups at the alpha and beta position.

The cyanobacterial heterocyclase may convert the cysteine residues in the linear pre-pro-peptide into thiazolines; threonine/serine residues into oxazolines; selenocysteines into selenazolines; tellurocysteines into tellurazolines and/or aminoalanines into imidazolines.

Heterocyclic amino acids include proline.

A cyanobacterial heterocyclase is an enzyme from a cyanobacterium which converts heterocyclisable residues into heterocycles. A cyanobacterial heterocyclase may recognise an N terminal leader sequence and/or a cyanobacterial protease recognition site, as described herein.

Suitable cyanobacterial heterocyclases include PatD heterocyclase (SEQ ID NO:3; AAY21153.1 GI:6291084) or TruD protease (SEQ ID NO: 4; ACA04490.1 GI:167859097) from *Prochloron* spp and heterocyclases from *Nostoc spongiaeforme* spp, such as TenD (ACA04483.1 GI:16785908). Other suitable heterocyclases are shown in Table 5.

In some embodiments, cyanobacterial heterocyclase may be selected depending on the residues in the linear pre-pro-peptide that are to be heterocyclised. For example, PatD may be used to heterocyclise Cys, Thr and Ser residues in the linear pre-pro-peptide and TruD may be used to heterocyclise Cys residues in the linear pre-pro-peptide but not Thr or Ser residues.

A cyanobacterial heterocyclase may comprise the amino sequence of any one of the above reference cyanobacterial heterocyclase sequences or may be a variant thereof. For example, a cyanobacterial heterocyclase may be a PatD or TruD heterocyclase which comprises the amino sequence of SEQ ID NO: 3 or 4 or a variant thereof. Variants of a reference amino acid sequence are described elsewhere herein.

In some embodiments, the pre-pro-peptide may comprise a leader sequence. The leader sequence may at the N or C terminal and is recognised by the heterocyclase. N terminal leader sequences may be removed by the protease after heterocyclisation, as described above.

The choice of leader sequence is dependent on the heterocyclase being employed. Suitable N terminal leader sequences include $PatE_{1-34}$, or $PatE_{26-34}$, which are recognised by PatD and TruD heterocylases.

The leader sequence may be heterologous.

In other embodiments, the leader sequence may be absent.

In some embodiments, the cyanobacterial heterocyclase may be modified by replacing the recognition domain with a first member of a binding pair. The leader sequence on the pre-pro-peptide may be replaced by the other member of the binding pair. Suitable binding pairs are well known in the art and include glutathione/glutathione binding protein and biotin/streptavidin. For example, the pre-pro-peptide may comprise an N terminal glutathione and the cyanobacterial heterocyclase may comprise a glutathione binding protein domain.

The pre-pro-peptide for heterocyclisation may further comprise a cyanobacterial protease recognition site as described herein which is recognised by the heterocyclase.

Methods of the production of cyanobacterial heterocyclases are described in more detail below.

The pre-pro-peptide may be treated with the cyanobacterial heterocyclase under suitable conditions to heterocyclise one or more heterocyclisable residues therein. For example, the pre-pro-peptide may be treated with the PatD or TruD heterocyclase in aqueous solution at ambient temperature in the presence of $Mg^{2+}$ and ATP. The highest temperature tolerated by the heterocyclase is generally preferred as this leads to increased reaction rates. The optimal temperature for reaction under a defined set of conditions may be determined experimentally.

In some embodiments, the pre-pro-peptide may be immobilised on a solid support and the cyanobacterial heterocyclase may be free in solution. In other embodiments, the linear pre-pro-peptide may be free in solution and the cyanobacterial heterocyclase may be immobilised on a solid support.

Heterocyclic residues, such as thiazolines, oxazolines, selenazolines, tellurazolines and imidazolines, in the the pre-pro-peptide, pro-peptide, linear peptide substrate or cyclic peptide may be subjected to oxidation to oxidise one or more heterocyclic residues in the target peptide sequence.

Thiazoline (Thn) residues in the linear pre-pro-peptide, pro-peptide, linear peptide substrate or cyclic peptide may be oxidized into thiazoles (Thz); oxazoline residues (Oxn) in the linear pre-pro-peptide, pro-peptide, linear peptide substrate or cyclic peptide may be oxidized into oxazoles (Oxz);

selenazolines (Sen) in the linear pre-pro-peptide, pro-peptide, linear peptide substrate or cyclic peptide may be oxidized into selenazoles (Sez); tellurazolines (Ten) in the linear pre-pro-peptide, pro-peptide, linear peptide substrate or cyclic peptide may be oxidized into tellurazoles (Tez) and imidazolines (Imn) in the linear pre-pro-peptide, pro-peptide, linear peptide substrate or cyclic peptide may be oxidized into imidazoles (Imz).

Bacterial, cyanobacterial or other enzymatic oxidases or chemical oxidizing agents may be employed.

In some embodiments, the pre-pro-peptide may be treated with a cyanobacterial or other enzymatic oxidase or chemical oxidizing agent following heterocyclisation. Treatment may occur directly after heterocyclisation to oxidise one or more heterocyclic residues in the target peptide sequence or oxidization may occur at a different stage, for example, the cyclic peptide may be treated with the oxidase or chemical oxidizing agent after macrocyclisation.

A cyanobacterial oxidase is an enzyme from a cyanobacterium which oxidises one or more heterocyclic amino acid residues.

Cyanobacterial oxidases may oxidise all the heterocyclic residues described herein or combinations thereof, for example oxazolines and thiazolines; or only thiazolines.

Suitable cyanobacterial oxidases include PatG oxidase (residues 1 to 491 of SEQ ID NO: 1) from *Prochloron* spp.

A cyanobacterial oxidase may comprise the amino sequence of any one of the above reference cyanobacterial oxidase sequences or may be a variant thereof. For example, a cyanobacterial oxidase may be a PatG oxidase which comprises the amino sequence of residues 1 to 491 of SEQ ID NO: 1 or a fragment, allele or variant thereof.

In some embodiments, bacterial oxidases may be employed to oxidise one or more heterocyclic amino acid residues. Suitable bacterial oxidases are well known in the art and include BcerB oxidase from the thiazole/oxazole modified microcin cluster (Melby et al J. Am. Chem. Soc, 2012, 134, 5309).

Sequences which are fragments or variants of a reference sequence are described below.

In some embodiments, the pre-pro-peptide may be treated with the cyanobacterial oxidase in the presence of flavin mononucleotide (FMN).

In some embodiments, the linear pre-pro-peptide may be immobilised on a solid support and the cyanobacterial oxidase may be free in solution; or the linear pre-pro-peptide may be free in solution and the cyanobacterial oxidase may be immobilised on a solid support.

Alternatively, following heterocyclisation, the pre-pro-peptide, pro-peptide, peptide substrate or cyclic peptide may be treated with a chemical oxidizing agent, such as $MnO_2$. Treatment with the agent may occur directly after heterocyclisation or at a different stage, for example after macrocyclisation. Suitable oxidation conditions may be determined by routine experimentation. For example, a cyclic peptide may be oxidised using $MnO_2$ in dichloromethane for three days at 28° C. to oxidise heterocycles.

Optionally, methods of the invention may further comprise treating a pre-pro-peptide, pro-peptide or peptide substrate with an epimerase, such that one or more amino acids in the target peptide sequence which are adjacent to a thiazoline are converted into D-epimers.

Alternatively, epimerisation of amino acids in the target peptide sequence which are adjacent to a thiazoline residue may be spontaneous and may not require treatment with an epimerase (Milne, B. F. et al *Org Biomol Chem* 4, 631-638 (2006)).

The linear pre-propeptide, pro-peptide, peptide substrate and/or cyclic peptide may be linked directly or indirectly to a tag. Tags may be useful in detection and purification and suitable tags are described below.

In some embodiments, a linear peptide or cyclic peptide, for example a macrocyclic peptide, may be produced by a method comprising one, two, three, four or more of the enzymatic steps described above. For example, a method of producing a cyclic peptide as described herein may comprise;

providing a pre-pro-peptide;
treating said pre-pro-peptide with a cyanobacterial heterocyclase,
treating said pro-peptide with a protease to produce a linear peptide substrate, and
treating said peptide with a cyanobacterial macrocyclase to produce a cyclic peptide.

The pro-peptide, peptide substrate or cyclic peptide may be treated with a cyanobacterial oxidase or chemical oxidising agent to oxidise heterocycles in the target peptide sequence.

The methods described above may allow the production of more than 1 mg/L of cyclic peptide. For example, the titre of the cyclic peptide in the reaction solution following cyclisation with the cyanobacterial macrocyclase may be more than 500 mg/L or more than 1 g/L.

In some embodiments, the above methods may be used to produce any one of the cyclic peptides described herein.

Following production of a cyclic peptide using a method described above, the cyclic peptide may be further treated.

The cyclic peptide may be produced in dimeric form and may be reduced to convert the dimeric peptides into monomers. Suitable reducing agents and conditions are well-known in the art and include TCEP, DTT and β-mercaptoethanol.

The cyclic peptide may be prenylated and/or geranylated. For example, the cyclic peptide may be treated with a cyanobacterial prenylase.

Cyanobacterial prenylases transfer farnesyl or geranylgeranyl isoprenoids to a cyclic peptide or a pre-pro-peptide, pro-peptide or peptide precursor as described herein.

Suitable cyanobacterial prenylases include PatF prenylase (GI: 62910842 AAY21155.1, SEQ ID NO: 5), GI: 167859100 ACA04493.1 (TruF2), and GI: 167859099 ACA04492.1 (TruF1) from *Prochloron* spp; GI: 159027547 CAO86917.1, GI: 158934373 CAO82086.1, GI: 389788445 CCI15906.1, GI: 389678155 CCH92965.1 (TenF), GI: 166362791 YP 001655064.1, GI:389831610 CCI25499.1, GI:389826377 CCI23120.1, GI: 389826383 CCI23131.1, GI: 389832530 CCI23767.1, GI:389716343 CCH99420.1, GI:389882386 CCI37135.1, GI:389720299 CCH95988.1, GI:389732896 CCI03253.1, GI:389734240 CCI02071.1, GI:389801748 CCI19127.1 and GI: 389802082 CCI18842.1 from *Microcystis* spp; GI:167859091 ACA04485.1 (TenF) from *Nostoc spongiaeforme* spp; GI:119492371 ZP_01623707.1 from *Lyngbya* spp; GI:280987227 ADA00390.1 (AcyF) from *Anabaena* sp; GI:376002283 ZP_09780119.1, GI:284054206 ZP_06384416.1 from *Arthrospira* sp; GI:332002616 AED99429.1 from *Planktothrix* spp; GI:300866527 ZP_07111217.1 from *Oscillatoria* spp.; and GI:220905949 YP 002481260.1 from *Cyanothece* spp.

A cyanobacterial prenylase may comprise the amino acid sequence of any one of the above reference cyanobacterial prenylase sequences or may be a variant thereof. For example, a cyanobacterial prenylase may be a PatF prenylase which comprises the amino acid sequence of SEQ ID NO: 5 or a fragment, allele or variant thereof.

The cyclic peptide may be subjected to further chemical modification. Suitable modifications include derivatisation with a heterologous moiety, for example, a moiety containing a natural side group such as OH, NH2, COOH, SH, or an unnatural side group suitable for coupling reactions and click chemistry.

Click-chemistry involves the Cu(I)-catalysed coupling between two components, one containing an azido group and the other a terminal acetylene group, to form a triazole ring. Since azido and alkyne groups are inert to the conditions of other coupling procedures and other functional groups found in peptides are inert to click chemistry conditions, click-chemistry allows the controlled attachment of almost any linker to the cyclic peptide under mild conditions. For example, non-cyclised cysteine residues of the cyclic peptide may be reacted with a bifunctional reagent containing a thiol-specific reactive group at one end (e.g. iodoacetamide, maleimide or phenylthiosulfonate) and an azide or acetylene at the other end. Label groups may be attached to the terminal azide or acetylene using click-chemistry. For example, a second linker with either an acetylene or azide group on one end of a linker and a chelate (for metal isotopes) or leaving group (for halogen labelling) on the other end (Baskin, J. (2007) *PNAS* 104(43)16793-97) may be employed.

The cyclic peptide may be labelled with a detectable label.

The detectable label may be any molecule, atom, ion or group which is detectable in vivo by a molecular imaging modality. Suitable detectable labels may include metals, radioactive isotopes and radio-opaque agents (e.g. gallium, technetium, indium, strontium, iodine, barium, bromine and phosphorus-containing compounds), radiolucent agents, contrast agents and fluorescent dyes.

The choice of detectable label depends on the molecular imaging modality which is to be employed. Molecular imaging modalities which may be employed include radiography, fluoroscopy, fluorescence imaging, high resolution ultrasound imaging, bioluminescence imaging, Magnetic Resonance Imaging (MRI), and nuclear imaging, for example scintigraphic techniques such as Positron Emission Tomography (PET) and Single Photon Emission Computerised Tomography (SPECT).

In vivo fluorescence imaging techniques involve the creation of an image using emission and absorbance spectra that are appropriate for the particular fluorescent detectable label used. The image can be visualized by conventional techniques, including Fluorescence imaging techniques may include Fluorescence Reflectance Imaging (FRI), fluorescence molecular tomography (FMT), Hyperspectral 3D fluorescence imaging (Guido Zavattini et al. Phys. Med. Biol. 51:2029, 2006) and diffuse optical spectroscopy (Luker & Luker. J Nucl Med. 49(1):1, 2008).

Suitable fluorescence detectable labels include fluorescein, phycoerythrin, Europium, TruRed, Allophycocyanin (APC), PerCP, Lissamine, Rhodamine, B X-Rhodamine, TRITC, BODIPY-FL, FluorX, Red 613, R-Phycoerythrin (PE), NBD, Lucifer yellow, Cascade Blue, Methoxycoumarin, Aminocoumarin, Texas Red, Hydroxycoumarin, Alexa Fluor™ dyes (Molecular Probes) such as Alexa Fluor™ 350, Alexa Fluor™ 488, Alexa Fluor™ 546, Alexa Fluor™ 568, Alexa Fluor™ 633, Alexa Fluor™ 647, Alexa Fluor™ 660 and Alexa Fluor™ 700, sulfonate cyanine dyes (AP Biotech), such as Cy2, Cy3, Cy3.5, Cy5, Cy5.5 and Cy7, IRD41 IRD700 (Li-Cor, Inc.), NIR-1 (Dejindom, Japan), La Jolla Blue (Diatron), DyLight™ 405, 488, 549, 633, 649, 680 and 800 Reactive Dyes (Pierce/Thermo Fisher Scientific Inc) or LI-COR™ dyes, such as IRDye™ (LI-COR™ Biosciences)

Other suitable fluorescent detectable labels include lanthanide ions, such as terbium and europium. Lanthanide ions may be attached to the synaptotagmin polypeptide by means of chelates, as described elsewhere herein.

Other suitable fluorescent detectable labels include quantum dots (e.g. Qdot™, Invitrogen). Techniques for labelling proteins with quantum dots are well-known in the art (Michalet, X. et al. Science 307:538, 2005; Alivisatos, P. Nat Biotechnol 22:47-52, 2004).

Magnetic resonance image-based techniques create images based on the relative relaxation rates of water protons in unique chemical environments. Suitable MRI techniques are described in more detail in Gadian, D. 'NMR and its applications to living systems'. Oxford Univ. Press, 1995, $2^{nd}$ edition). Magnetic resonance imaging may include conventional magnetic resonance imaging (MRI), magnetization transfer imaging (MTI), magnetic resonance spectroscopy (MRS), diffusion-weighted imaging (DWI) and functional MR imaging (fMRI) (Rovaris et al. (2001) JNeurol Sci 186 Suppl 1: S3-9; Pomper & Port (2000) Magn Reson Imaging Clin N Am 8: 691-713; Kean & Smith, (1986) Magnetic Resonance Imaging: Principles and Applications, Williams and Wilkins, Baltimore, Md.).

Labels suitable for use as magnetic resonance imaging (MRI) labels may include paramagnetic or superparamagnetic ions, iron oxide particles, and water-soluble contrast agents. Superparamagnetic and paramagnetic ions may include transition, lanthanide and actinide elements such as iron, copper, manganese, chromium, erbium, europium, dysprosium, holmium and gadolinium. Preferred paramagnetic detectable labels include gadolinium.

A cyclic peptide may be attached to an antibody molecule, such as an antibody or antibody fragment or derivative, for example for use in antibody-directed drug therapies. Suitable techniques for the conjugation of cyclic peptides and antibodies are well known in the art.

Cyclic peptides produced as described herein may be useful in therapeutics, nanotechnology applications and in optical/electronic or contractile materials.

An isolated enzyme or other protein exists in a physical milieu distinct from that in which it occurs in nature, or in which it was produced recombinantly. For example, the isolated peptide may be substantially isolated with respect to the complex cellular milieu in which it naturally occurs. The absolute level of purity is not critical, and those skilled in the art can readily determine appropriate levels of purity according to the use to which the protein is to be put.

A heterologous element is an element which is not associated or linked to the subject feature in its natural environment i.e. association with a heterologous element is artificial and the element is only associated or linked to the subject feature through human intervention.

One or more heterologous amino acids, for example a heterologous peptide or heterologous polypeptide sequence, may be joined or fused to a linear peptide substrate, propeptide, pre-pro-peptide, macrocyclase, oxidase, heterocyclase, protease or other protein set out herein. For example a pre-pro-peptide may comprise a pre-pro-peptide as described above linked or fused to one or more heterologous amino acids. The one or more heterologous amino acids may include sequences from a source other than cyanobacteria.

In some embodiments, a linear peptide substrate, propeptide, pre-pro-peptide, macrocyclase, oxidase, heterocyclase, protease or other protein set out herein may be expressed as a fusion protein with a purification tag. Preferably the fusion protein comprises a protease recognition site between the enzyme sequence and purification tag. Following expression, the fusion protein may be isolated by affinity chromatography using an immobilised agent which binds to the purification tag.

The purification tag is a heterologous amino acid sequence which forms one member of a specific binding pair. Polypeptides containing the purification tag may be detected, isolated and/or purified through the binding of the other member of the specific binding pair to the polypeptide. In some preferred embodiments, the tag sequence may form an epitope which is bound by an antibody molecule.

Various suitable purification tags are known in the art, including, for example, MRGS(H)$_6$ (SEQ ID NO: 61), DYKDDDDK (SEQ ID NO: 62) (FLAG™), T7-, S-(KETAAAKFERQHMDS) (SEQ ID NO: 63), poly-Arg (R$_{5-6}$), poly-His (H$_{2-10}$), poly-Cys (C$_4$) poly-Phe (F$_{11}$) poly-Asp (D$_{5-16}$), Strept-tag II (WSHPQFEK) (SEQ ID NO: 64), c-myc (EQKLISEEDL) (SEQ ID NO: 65), Influenza-HA tag (Murray, P. J. et al (1995) *Anal Biochem* 229, 170-9), Glu-Glu-Phe tag (Stammers, D. K. et al (1991) *FEBS Lett* 283, 298-302), SUMO (Marblestone et al *Protein Sci.* 2006 January; 15(1): 182-189), Cherry tag (Eurogentec), Tag.100 (Qiagen; 12 aa tag derived from mammalian MAP kinase 2), Cruz tag 09™ (MKAEFRRQESDR (SEQ ID NO: 66), Santa Cruz Biotechnology Inc.) and Cruz tag 22™ (MRDALDRLDRLA (SEQ ID NO: 67), Santa Cruz Biotechnology Inc.). Known tag sequences are reviewed in Terpe (2003) Appl. Microbiol. Biotechnol. 60 523-533. The TAG sequence may be linked to the target protein through a protease recognition site, for example a TEV protease site, to facilitate removal following purification.

In some preferred embodiments, the purification tag is glutathione-S-transferase. Following expression, a fusion protein comprising the linear peptide substrate, pro-peptide, pre-pro-peptide, macrocyclase, oxidase, heterocyclase, protease or other protein set out herein and glutathione-S-transferase may be isolated by affinity chromatography using immobilised glutathione (or vice versa). The purification of glutathione-S-transferase fusion proteins is well known in the art.

In other preferred embodiments, the purification tag is a Small Ubiquitin-like Modifier (SUMO) tag or a His$_6$-SUMO tag. Following expression, a fusion protein comprising the linear peptide substrate, pro-peptide, pre-pro-peptide, macrocyclase, oxidase, heterocyclase, protease or other protein set out herein and the SUMO or His$_6$-SUMO tag may be isolated by affinity chromatography using immobilised glutathione (or vice versa). The purification of SUMO-tagged fusion proteins is well known in the art.

After isolation, the fusion protein may then be proteolytically cleaved to produce the linear peptide substrate, pro-peptide, pre-pro-peptide, macrocyclase, oxidase, heterocyclase, protease or other protein set out herein.

Linear peptide substrates, pro-peptides and pre-pro-peptides as described herein may be generated wholly or partly by chemical synthesis. For example, peptides and polypeptides may be synthesised using liquid or solid-phase synthesis methods; in solution; or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Chemical synthesis of peptides and polypeptides is well-known in the art (J. M. Stewart and J. D. Young, Solid Phase Peptide Synthesis, 2nd edition, Pierce Chemical Company, Rockford, Ill. (1984); M. Bodanzsky and A. Bodanzsky, The Practice of Peptide Synthesis, Springer Verlag, New York (1984); J. H. Jones, The Chemical Synthesis of Peptides. Oxford University Press, Oxford 1991; in Applied Biosystems 430A Users Manual, ABI Inc., Foster City, Calif.; G. A. Grant, (Ed.) Synthetic Peptides, A User's Guide. W. H. Freeman & Co., New York 1992, E. Atherton and R. C. Sheppard, Solid Phase Peptide Synthesis, A Practical Approach. IRL Press 1989 and in G. B. Fields, (Ed.) Solid-Phase Peptide Synthesis (Methods in Enzymology Vol. 289). Academic Press, New York and London 1997).

Linear peptide substrates, pro-peptides and pre-pro-peptides as described herein may be generated wholly or partly by recombinant techniques. For example, a nucleic acid encoding a linear peptide substrate, pro-peptide and pre-pro-peptide as described herein may be expressed in a host cell and the expressed polypeptide isolated and/or purified from the cell culture.

Macrocyclases, oxidases, heterocyclases, proteases and other enzymes out above may be generated wholly or partly by recombinant techniques. For example, a nucleic acid encoding the enzyme may be expressed in a host cell and the expressed polypeptide isolated and/or purified from the cell culture. Preferably, enzymes are expressed from nucleic acid which has been codon optimised for expression in *E. coli*.

Nucleic acid sequences and constructs as described above may be comprised within an expression vector. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in a host cell. Suitable regulatory sequences to drive the expression of heterologous nucleic acid coding sequences in expression systems are well-known in the art and include constitutive promoters, for example viral promoters such as CMV or SV40, and inducible promoters, such as Tet-on controlled promoters. A vector may also comprise sequences, such as origins of replication and selectable markers, which allow for its selection and replication and expression in bacterial hosts such as *E. coli* and/or in eukaryotic cells.

Vectors may be plasmids, viral e.g. 'phage, or phagemid, as appropriate. For further details see, for example, *Molecular Cloning: a Laboratory Manual:* 3rd edition, Russell et al., 2001, Cold Spring Harbor Laboratory Press. Many known techniques and protocols for expression of recombinant polypeptides in cell culture and their subsequent isolation and purification are known in the art (see for example Protocols in *Molecular Biology*, Second Edition, Ausubel et al. eds. John Wiley & Sons, 1992; *Recombinant Gene Expression Protocols* Ed R S Tuan (March 1997) Humana Press Inc).

In some embodiments, macrocyclases, oxidases, heterocyclases, proteases and other enzymes set out above may be expressed as fusion proteins with a purification tag, as described above.

Macrocyclases, oxidases, heterocyclases, proteases and other enzymes set out above and linear peptide substrates, pro-peptides and pre-pro-peptides may be immobilised on a solid support.

A solid support is an insoluble, non-gelatinous body which presents a surface on which the peptides or proteins can be immobilised. Examples of suitable supports include glass slides, microwells, membranes, or beads. The support may be in particulate or solid form, including for example a plate, a test tube, bead, a ball, filter, fabric, polymer or a membrane. A peptide or protein may, for example, be fixed to an inert polymer, a 96-well plate, other device, apparatus or material. The immobilisation of peptides and proteins to the surface of solid supports is well-known in the art.

As described above, cyanobacterial macrocyclases, oxidases, heterocyclases and proteases may comprise an amino acid sequence which is a variant or fragment of a reference amino acid sequence.

A variant of a reference amino acid sequence may have an amino acid sequence having at least 60%, at least 70%, at least 75%, at least 80%, at least 85%, at least 90%, at least 95% or at least 98% sequence identity to the reference amino acid sequence.

Suitable reference amino acid sequences for cyanbacterial cyanobacterial macrocyclases, oxidases, heterocyclases and proteases are provided above. Amino acid sequence identity is generally defined with reference to the algorithm GAP (GCG Wisconsin Package™, Accelrys, San Diego Calif.). GAP uses the Needleman & Wunsch algorithm (J. Mol. Biol. (48): 444-453 (1970)) to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST or TBLASTN (which use the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), generally employing default parameters.

Particular amino acid sequence variants may differ from that in a given sequence by insertion, addition, substitution or deletion of 1 amino acid, 2, 3, 4, 5-10, 10-20 or 20-30 amino acids. In some embodiments, a variant sequence may comprise the reference sequence with 1, 2, 3, 4, 5, 6, 7, 8, 9, 10 or more residues inserted, deleted or substituted. For example, up to 15, up to 20, up to 30, up to 40, up to 50 or up to 60 residues may be inserted, deleted or substituted.

A fragment is a truncated protein which contains less than the full-length amino acid sequence but which retains the activity of the full-length protein sequence. A fragment may comprise at least 100 amino acids, at least 200 amino acids or at least 300 contiguous amino acids from the full-length sequence.

The methods described herein may be useful in screening cyclic peptides for biological or other activity.

The linear peptide substrate, linear pre-pro-peptide, and/or linear pro-peptide may be immobilised on a bead. In some embodiments, a reference linear peptide substrate, linear pre-pro-peptide, and/or linear pro-peptide which does not include a cyclisation signal may also be immobilised to the same bead.

The bead may be treated with a cyanobacterial macrocyclase as described herein, such that the linear peptide is cyclised and the cyclic peptide may be released from the bead, while the reference peptide substrate lacking the cyclisation signal remains attached.

The released cyclic peptide may then be isolated and screened for a biological activity.

If the cyclic peptide is found to display a biological activity, the bead from which the cyclic peptide was released may be identified and the reference peptide substrate sequenced or otherwise analysed, to allow characterisation of the bioactive cyclic peptide.

Methods as described herein may also be useful in the production and screening of libraries of cyclic peptides. A method of screening a cyclic peptide library may comprise;
 (i) providing a diverse population of target peptides attached to beads,
  each bead having a first and a second copy of the target peptide attached thereto, wherein the first copy but not the second copy is attached to the bead via a cyclisation signal,
 (ii) treating said beads with a PatGmac macrocyclase to convert the first copy of the target peptide into a cyclic peptide and release the cyclic peptides from the beads,
 (iii) screening the cyclic peptides for activity,
 (iv) identifying an active cyclic peptide
 (v) identifying the bead from which the cyclic peptide was released, and
 (vi) sequencing the second copy of the target peptide attached to the bead.

The diverse population of target peptides may be spatially arrayed, for example, in one or more multi-well plates, such that the bead from which the cyclic peptide was released can be identified. For example, each individual well in a multi-well plate may contain a homogenous population of target peptides.

The cyclic peptides which are screened may contain one, two, three or more heterocyclic amino acid residues. For example, step (i) of a screening method described above may further comprise;
 treating said target peptides with a cyanobacterial heterocyclase to convert heterocyclisable residues in the of target peptides into cyclic residues and,
 optionally further treating the target peptides with an cyanobacterial oxidase to oxidise cyclic residues therein.

Other aspects of the invention provide a peptide substrate as described herein for use in the production of a cyclic peptide and a population of diverse peptide substrates for use in the production of a cyclic peptide library.

A peptide substrate may comprise a target peptide sequence having an N terminal protease recognition site and a C terminal cyclisation signal.

The protease recognition site and/or the cyclisation signal may be heterologous to the target sequence. Preferably the protease recognition site is a trypsin or chymotrypsin recognition site.

The peptide substrate may further comprise an N terminal leader sequence or an N terminal binding moiety.

In some embodiments, the peptide substrate may be directly or indirectly linked to an N and/or C terminal tag.

In some embodiments, the peptide substrate may be immobilized on a solid support, such as a bead. As described above, a reference copy of the target peptide sequence may also be immobilized on a solid support without a cyclisation signal.

A population may comprise peptide substrates as described above, wherein the target peptide sequence is diverse within the population. For example, one, two, three, four or more, or all positions in the target peptide sequence may display diversity i.e. different members of the population may display a different residue at the position.

Preferably, the residue adjacent the cyclisation signal in the peptides in the population is Pro, heterocycle, a N-Me residue or other artificial residue with the correct conformational properties, as described above.

Suitable linear peptide substrates are described in more detail above.

Other aspects of the invention provide materials, reagents and kits and reagents for use in the production of cyclic peptides and populations thereof and the use of such cyclic peptides, for example in screening methods.

Materials may include individual or combinations of isolated pre-pro-peptides, pro-peptides, peptide substrates and recombinant macrocyclases, proteases, oxidases, and heterocyclases as described above. Reagents may be immobilized on solid supports.

A kit may comprise a peptide substrate or library of substrates as described above. For example, a kit may comprise a multi-well plate;
    each individual well containing a homogenous population of target peptides target peptides attached to beads,
    each bead having a first and a second copy of the target peptide attached thereto, wherein the first copy but not the second copy is attached to the bead via a cyclisation signal,
    the sequences of the target peptides being different in different wells.

A kit may further comprise isolated enzyme preparations for use in the methods described above.

Other aspects and embodiments of the invention provide the aspects and embodiments described above with the term "comprising" replaced by the term "consisting of" and the aspects and embodiments described above with the term "comprising" replaced by the term "consisting essentially of".

Various further aspects and embodiments of the present invention will be apparent to those skilled in the art in view of the present disclosure.

All documents and database entries which are mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments of the invention which are described. Thus, the features set out above are disclosed for use in the invention in all combinations and permutations.

Certain aspects and embodiments of the invention will now be illustrated by way of example and with reference to the figures and tables described herein.

FIGS. 1A and 1B show a sequence alignment of PatGmac with its homologs (SEQ ID NOs: 7-19). Secondary structure elements are shown. Active site residues are indicated by stars, cysteines involved in disulfide bonding as triangles (matching directions represent disulfide pairs), residues blocking the S3 and S4 sites as diamonds, lysines forming salt-bridges with the substrate as circles and His and Phe residues involved in substrate binding are marked by a box. FIG. 1C shows the relative reaction rates of PatGmac and VGAGIGFPAYDG (SEQ ID NO: 68) in different buffers and temperatures as determined by LC-MS.

Figure 4A:
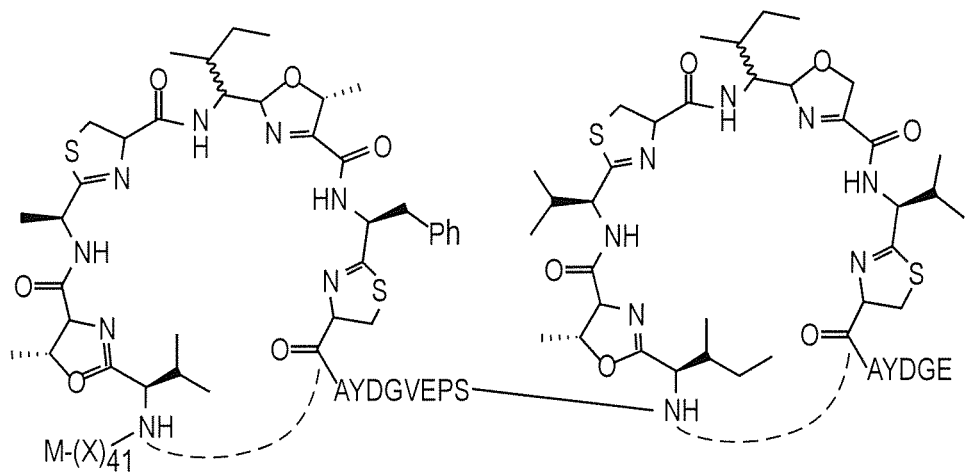
Figure 4B:
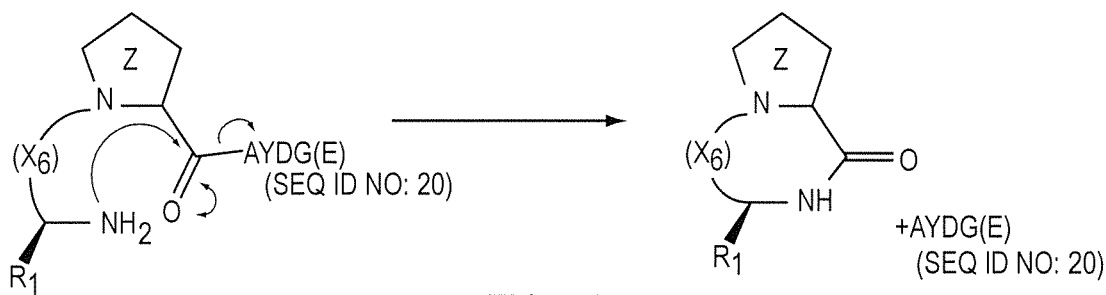
Figure 4C:
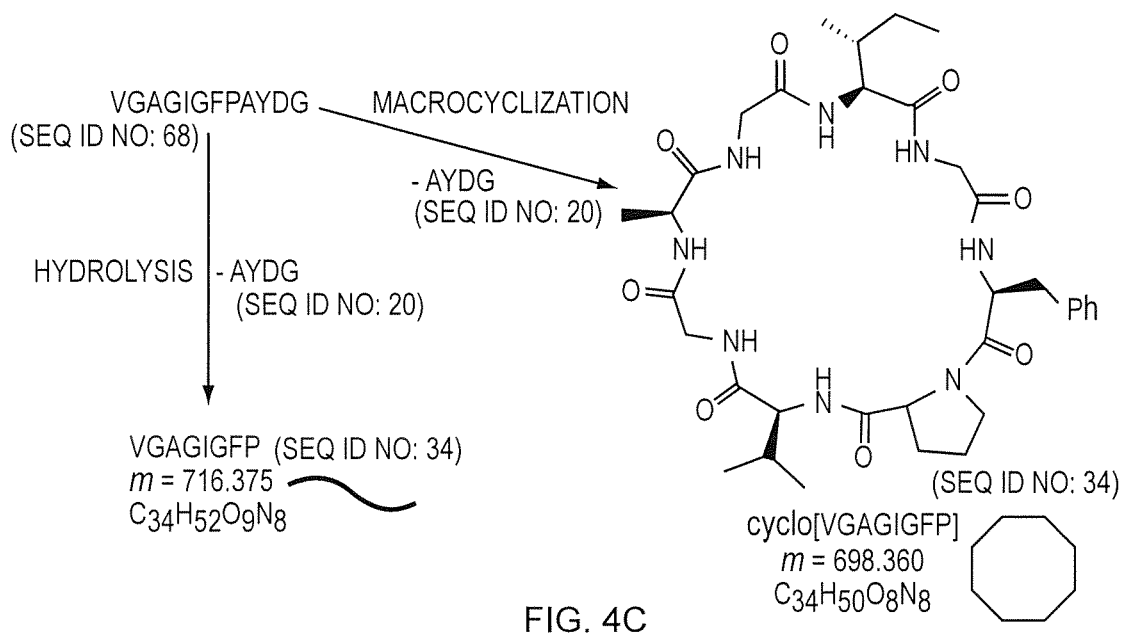

FIGS. 4A-4C show patellamide macrocylization. FIG. 4A shows a PatE pre-pro-peptide consisting of an N-terminal leader sequence followed by two eight-residue cassettes with the C-terminal macrocyclase recognition signal AYDG (SEQ ID NO: 20). The macrocyclization domain of PatG catalyzes the formation of two cyclic peptides per pre-pro-peptide (dashed lines). FIG. 4B shows that PatGmac requires a heterocycle or proline (denoted Z) at the P1 position and the AYDG (SEQ ID NO: 20) motif at the P1' to P4' sites respectively. An additional E is often found at P5' but is not required. FIG. 4C shows that the test substrate used in this study can either give a linear peptide of mass 716.375 Da (curved line) or macrocycle, which has a mass 18 Da lighter (octagon).

Figure 5:
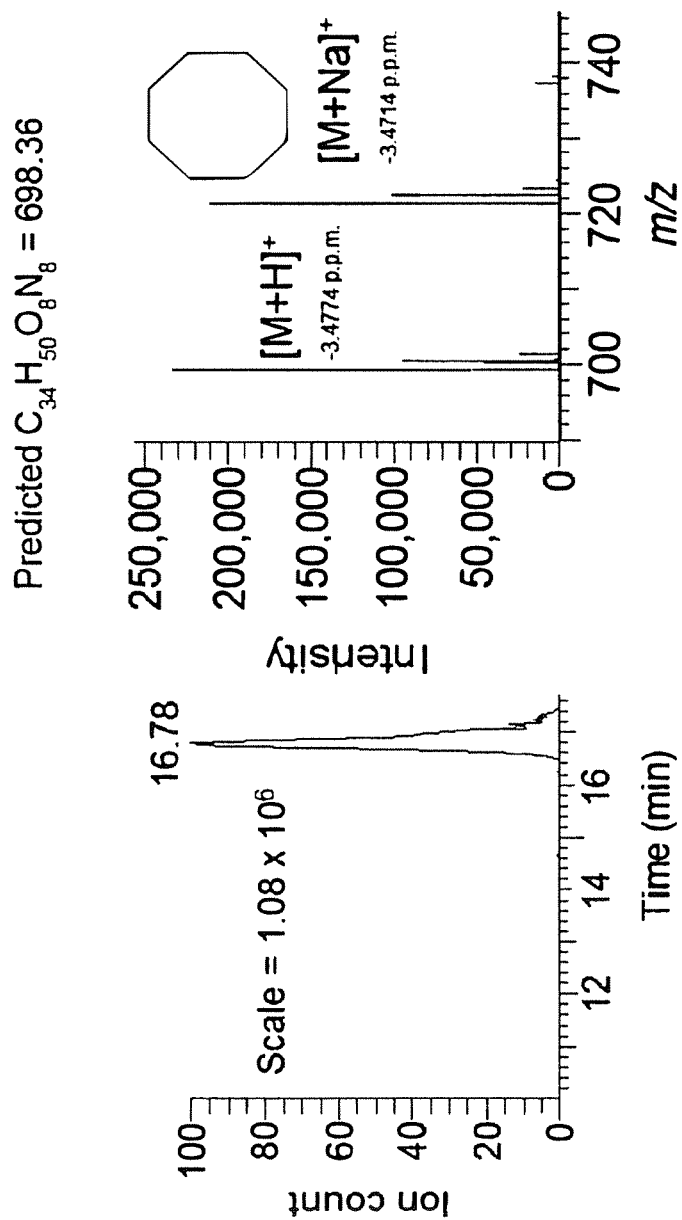

FIG. 5 shows an LC-MS of macrocyclization reactions with PatGmac wild-typeMacrocyclized and linear products are indicated with octagons and curved lines, respectively. The error between observed and calculated mass is shown below the $[M+H]^+$ and $[M+Na]^+$ species.

Figure 6:
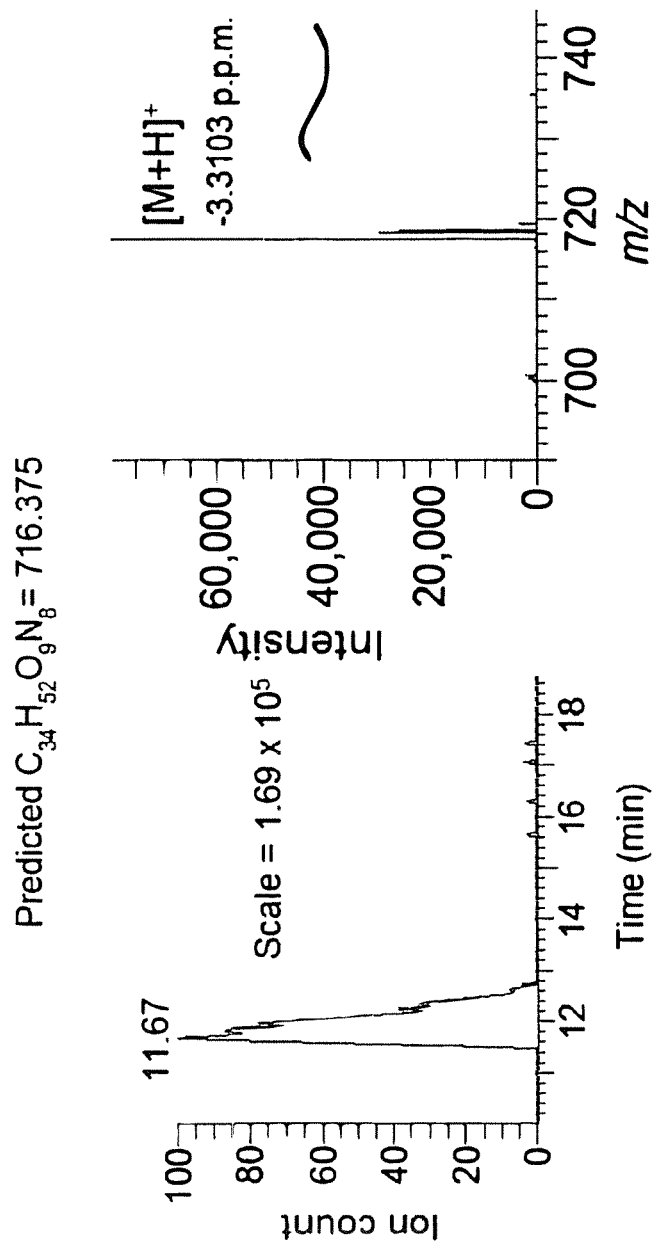

FIG. 6 shows an LC-MS of macrocyclization reactions with PatGmacΔ2m as per FIG. 5.

Figure 7:
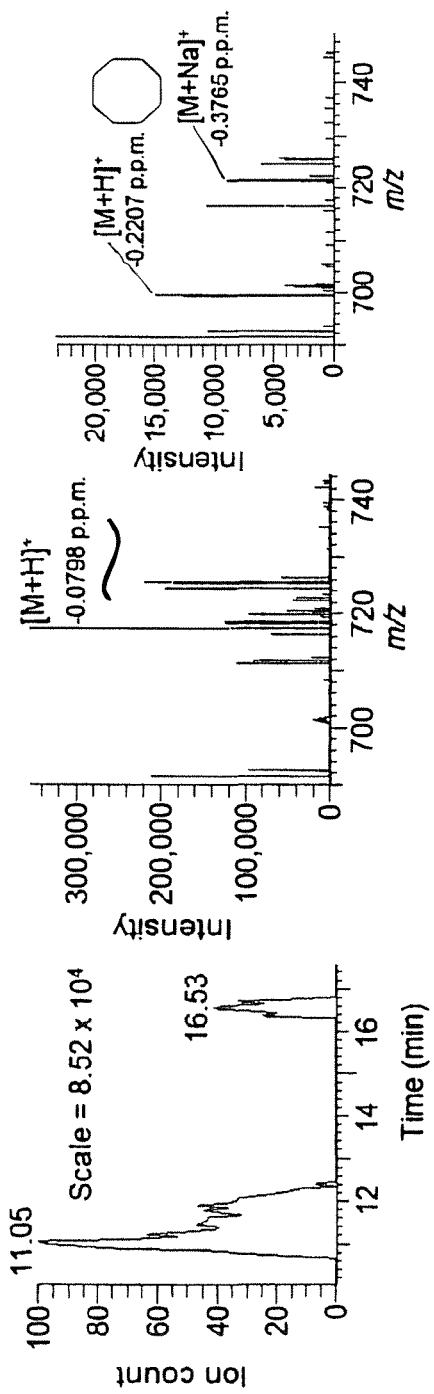

FIG. 7 shows an LC-MS of macrocyclization reactions with PatGmac K594D, as per FIG. 5.

Figure 8:
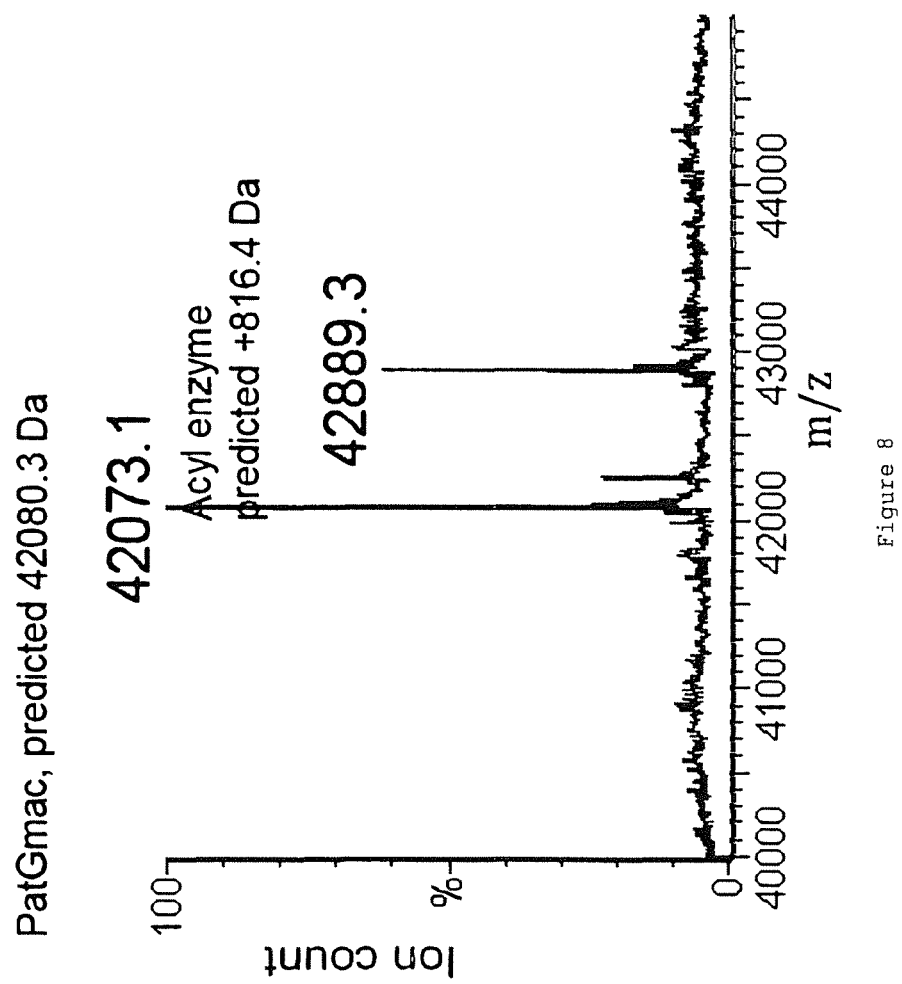

FIG. 8 shows LC-MS of a macrocyclization reaction with PatGmac that shiows the existence of a stable acyl-enzyme intermediate (AEI) between PatGmac and substrate.

Figure 9:
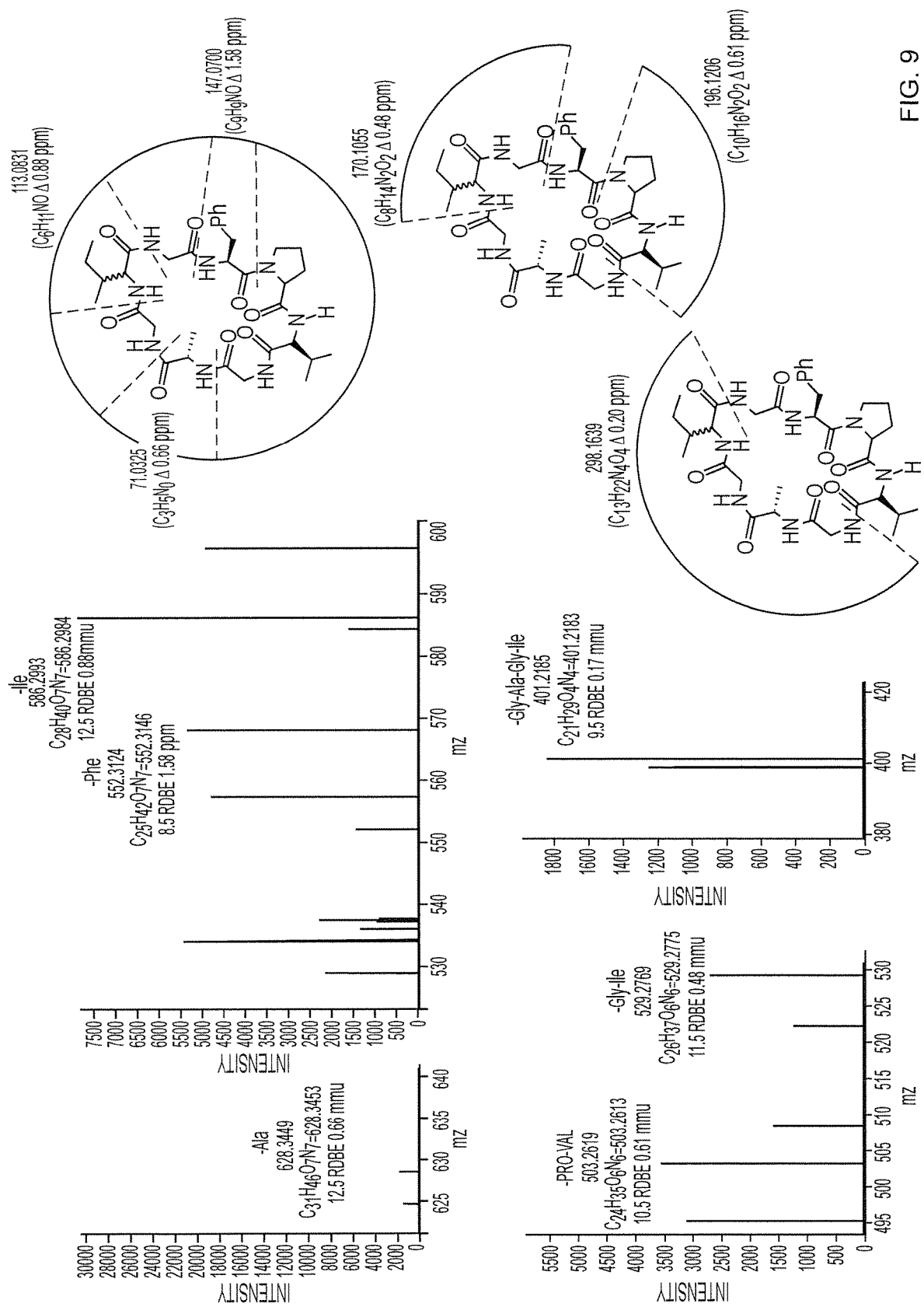

FIG. 9 shows the fragmentation pattern of cyclo [VGAGIGFP] (SEQ ID NO: 70) determined during an MS analysis of macrocyclization reactions.

Figure 10A:
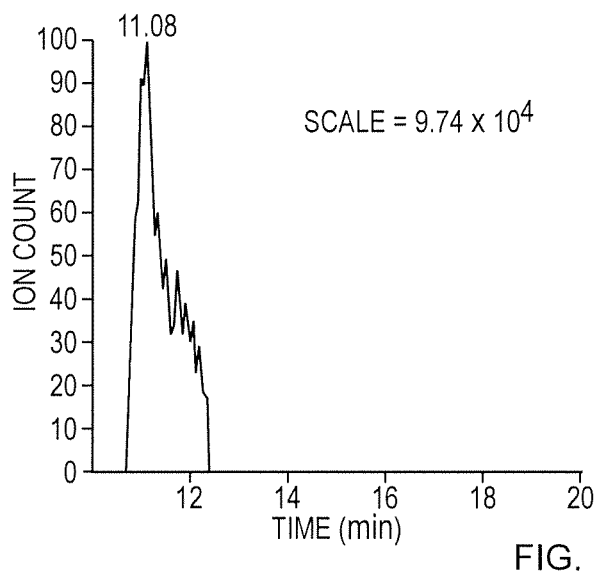
Figure 10A:
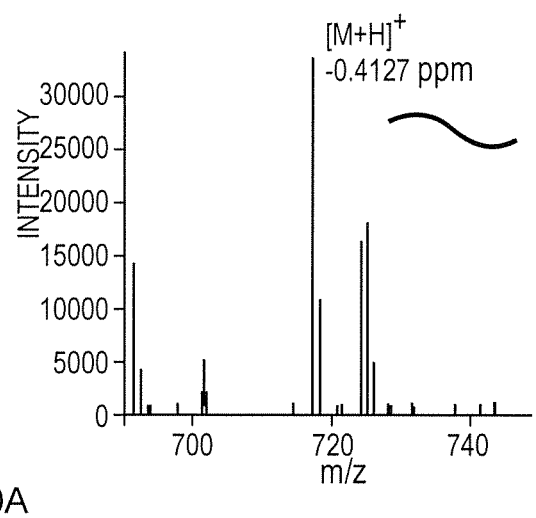
Figure 10B:
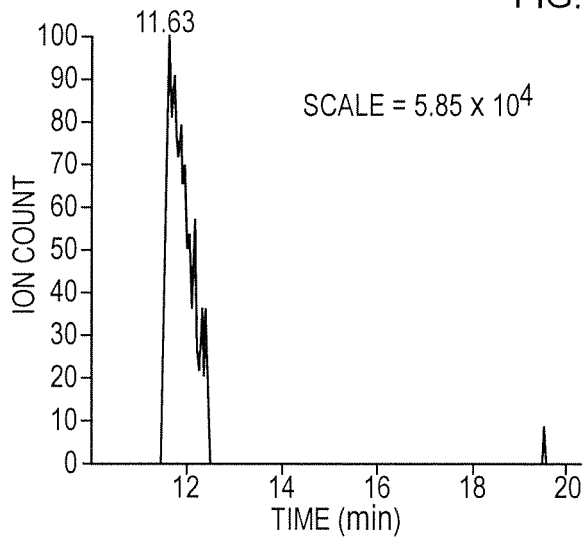
Figure 10B:
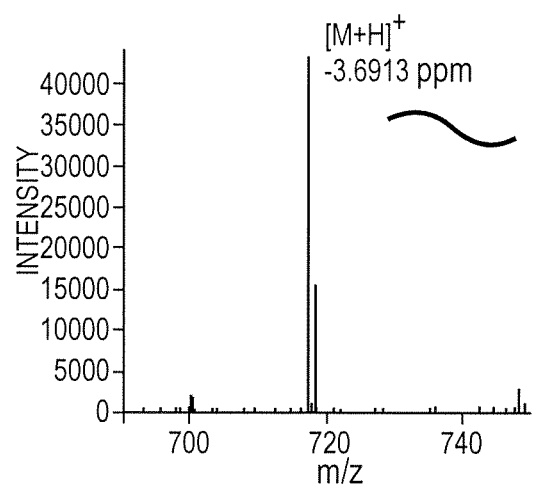
Figure 10C:
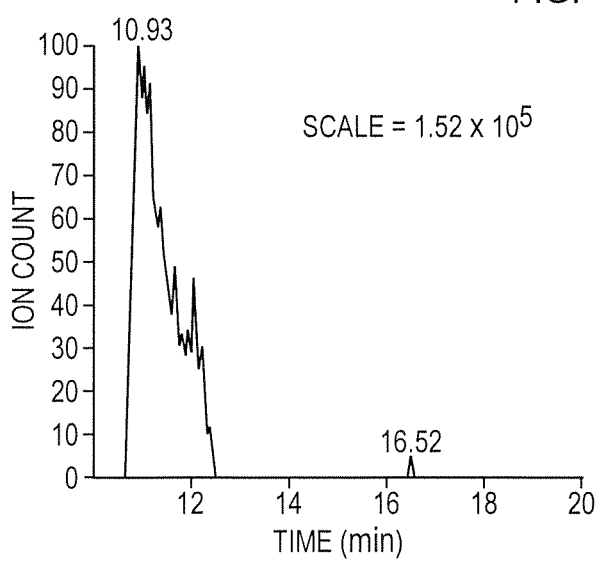
Figure 10C:
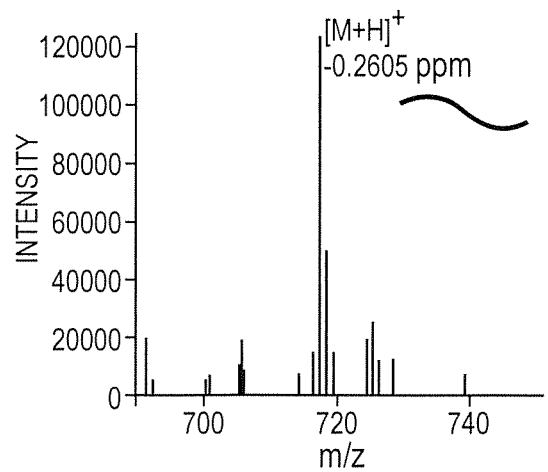

FIGS. 10A, 10B, and 10C show LC-MS of macrocyclization reactions with PatGmacΔ1, PatGmac K598D and PatGmac triple mutant R589D K594D K598D, respectively. Only linear product is observed (curved lines). The error between observed and calculated mass is shown below the $[M+H]^+$ species.

Figure 11A:
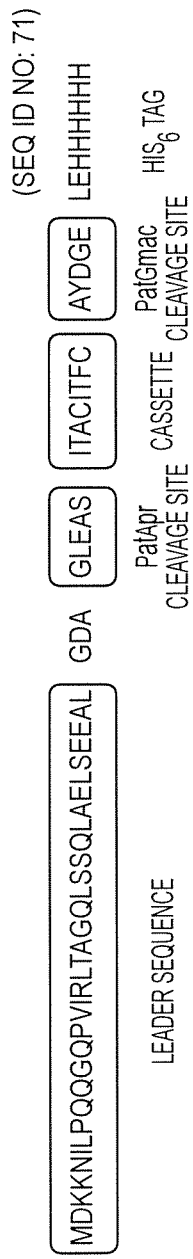
Figure 11B:
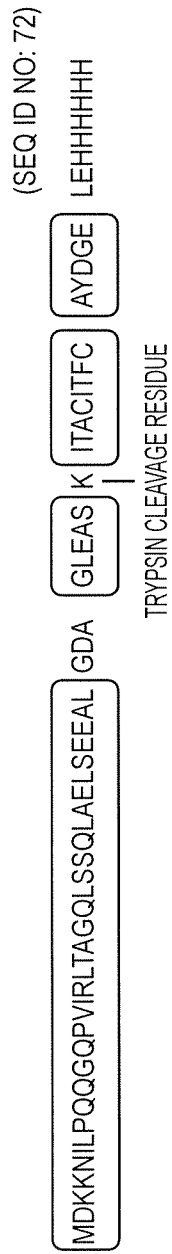

FIGS. 11A and 11B show an engineered PatE pre-pro-peptide (PatE2) (SEQ ID NO: 71 and SEQ ID NO: 72).

Figure 12:
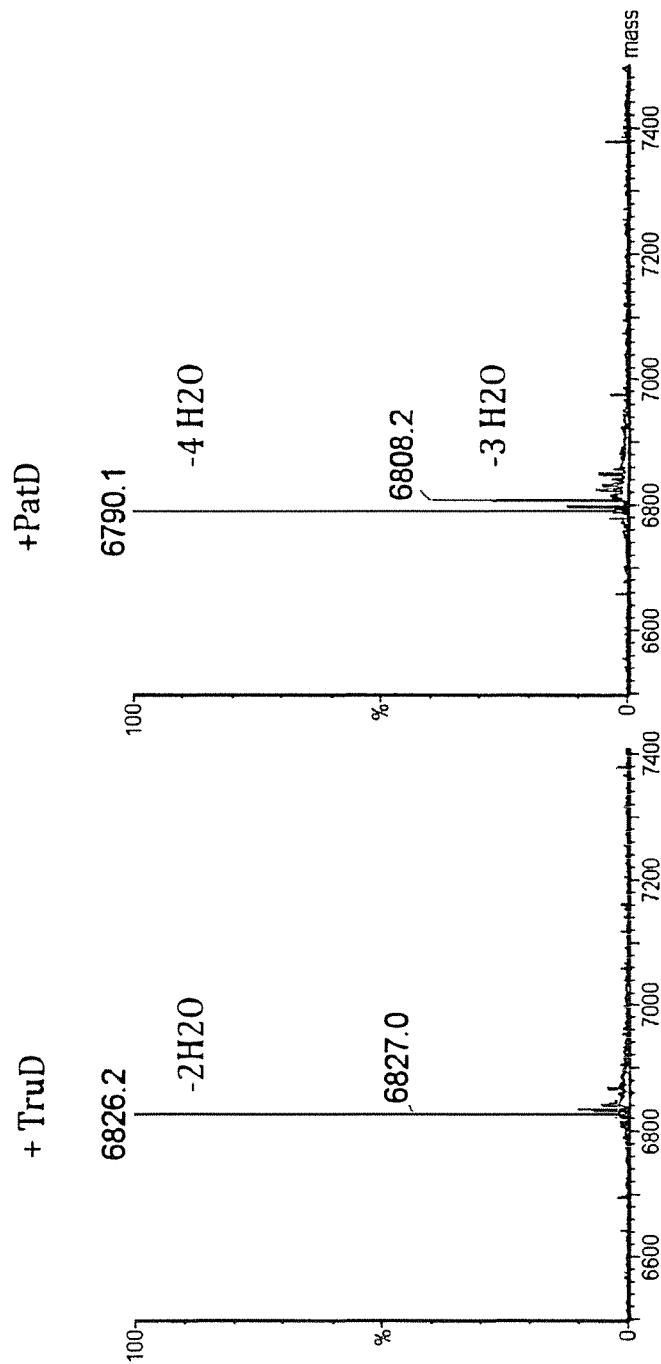

FIG. 12 shows data relating to the in vitro heterocyclization of PatE2. Note that for PatD reaction, species with only three heterocycles might have unique properties and can be separated from the species with four heterocycles by HPLC.

Figure 13A:
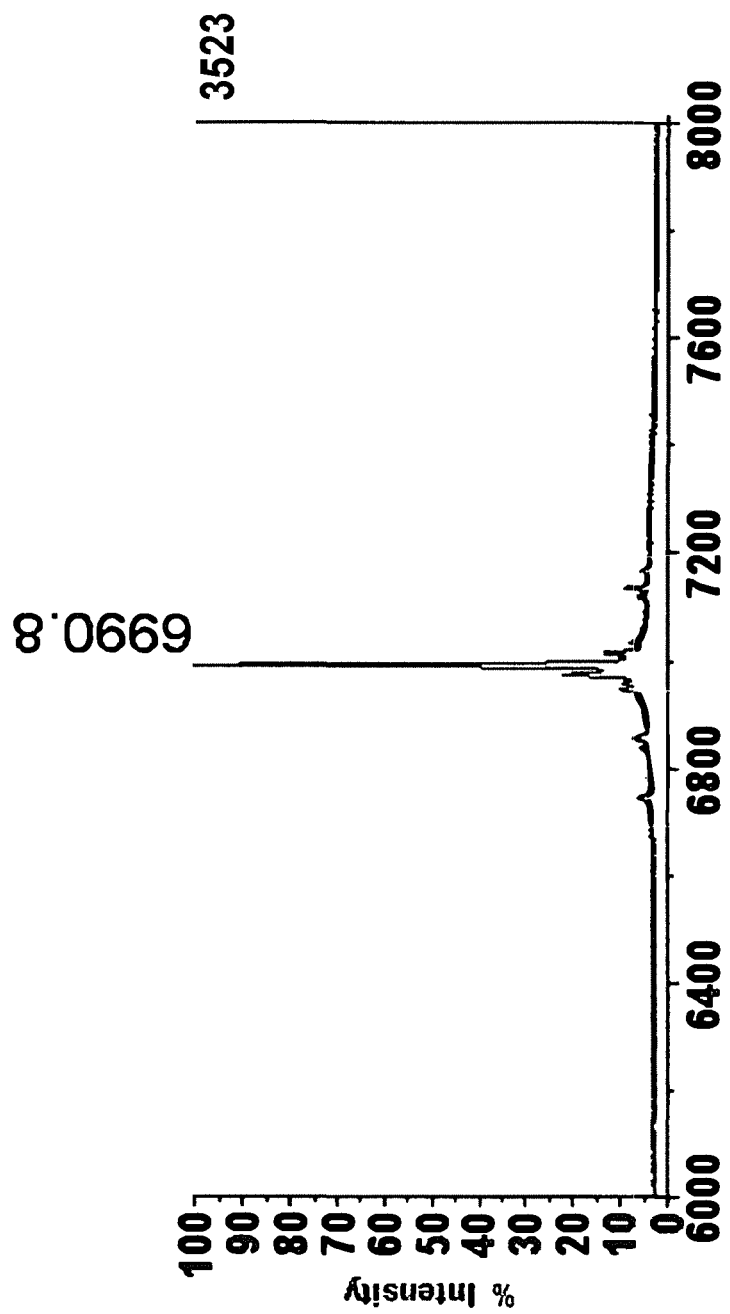
Figure 13B:
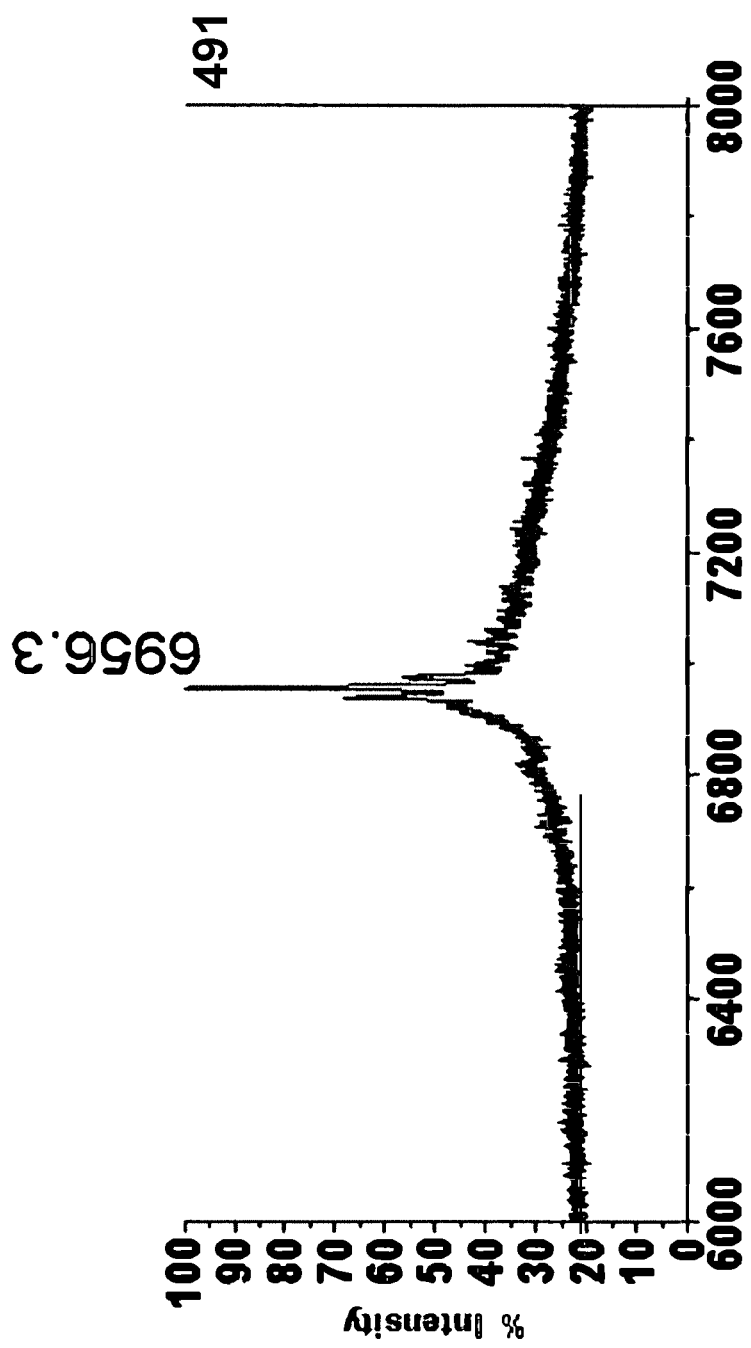

FIGS. 13A and 13B show water loss following incubation of PatE2 with TruD. FIG. 13A shows PatE with engineered lysine residue before heterocyclisation and FIG. 13B shows PatE2 after heterocyclisation.

Figure 14:
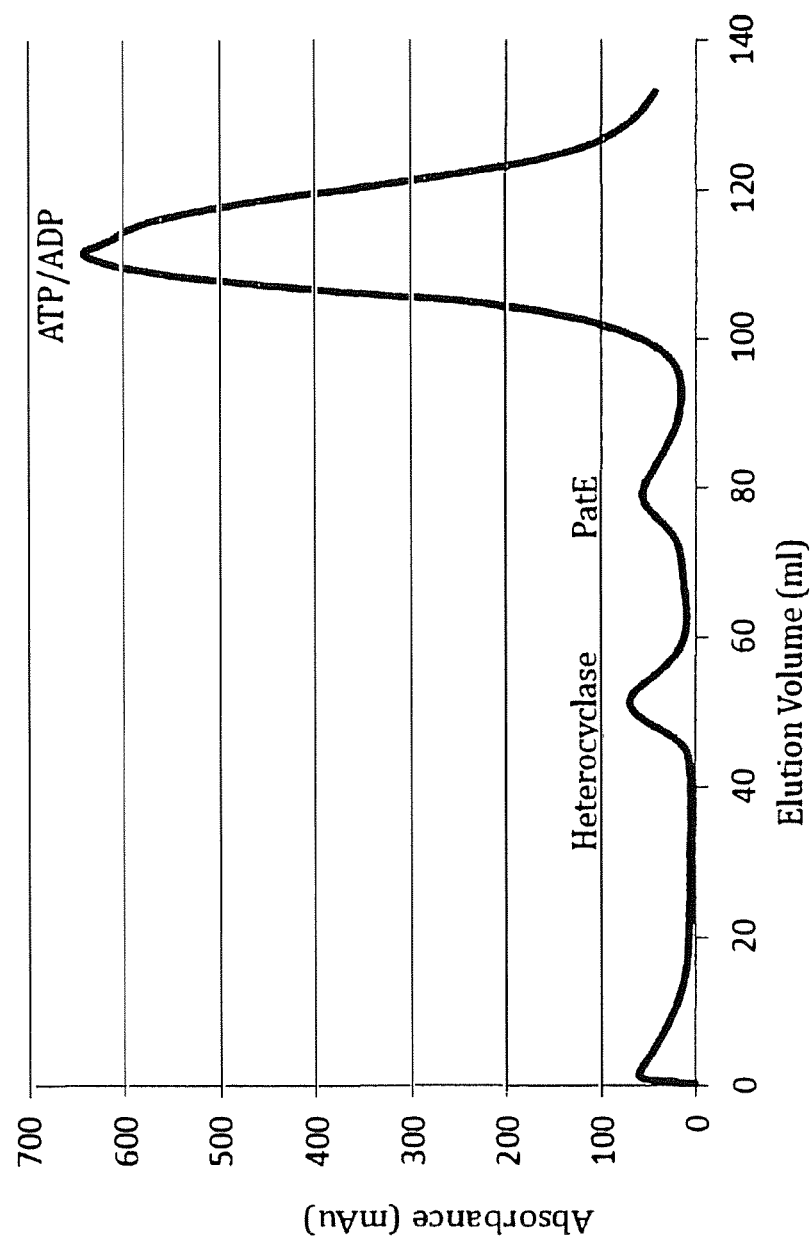

FIG. 14 shows a S200 gel filtration trace produced after completion of the heterocyclisation reaction.

Figure 15:
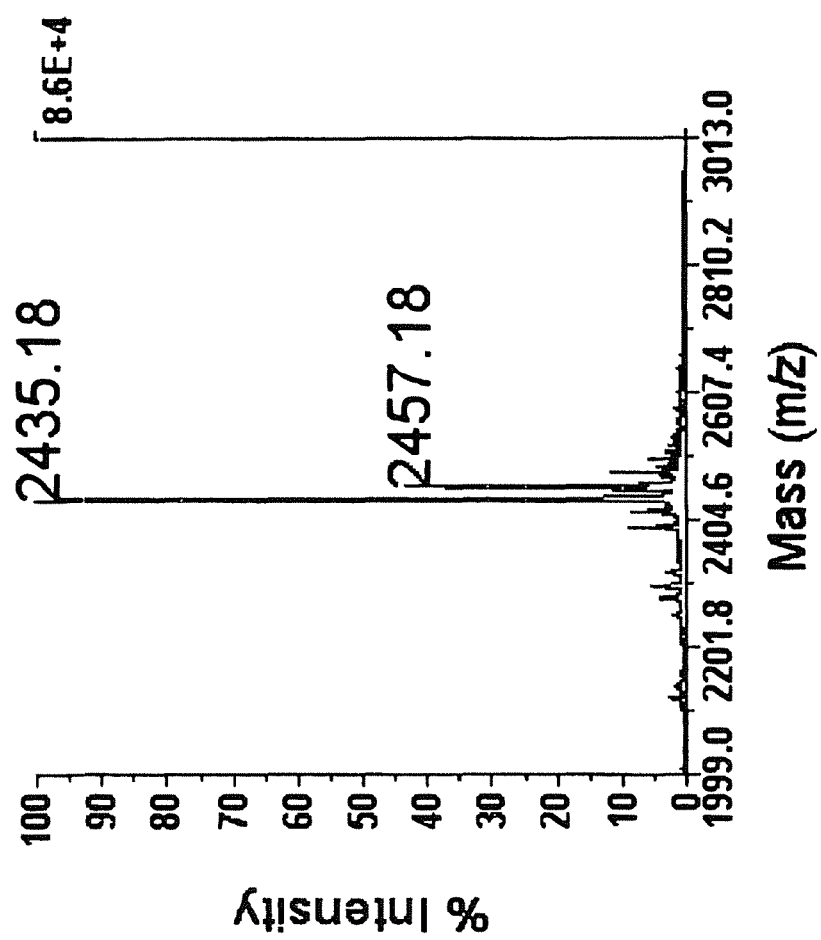

FIG. 15 shows LC-MS of PatE2 following N-terminal cleavage with Trypsin and heterocyclisation with TruD.

Figure 16:
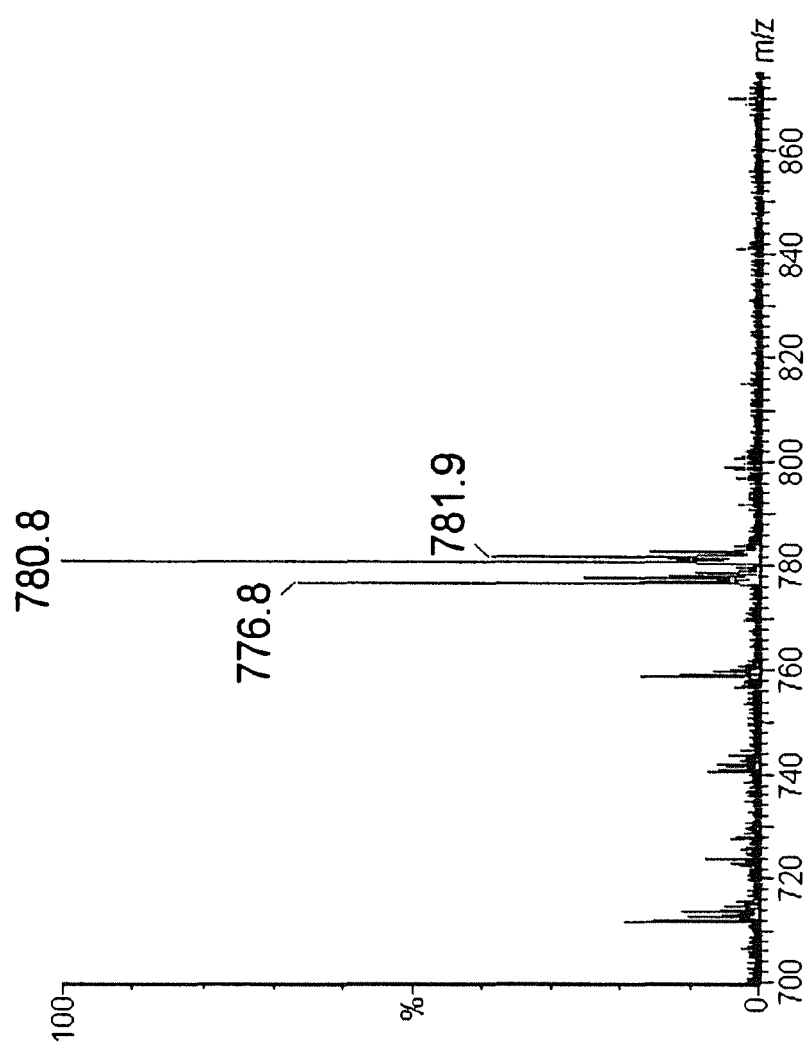

FIG. 16 shows LCT-ESI MS data of Patellamide (cyclo (I(MxOxn)A(Thn)I(MeOxn)F(Thn)) (SEQ ID NO: 73) produced from peptide substrate ITACITFC(SEQ ID NO: 21). The data confirms the final product has 4 heterocycles and is macrocyclised (expected mass 781 Da). The 776 Da species is the oxidized product.

Figure 17:
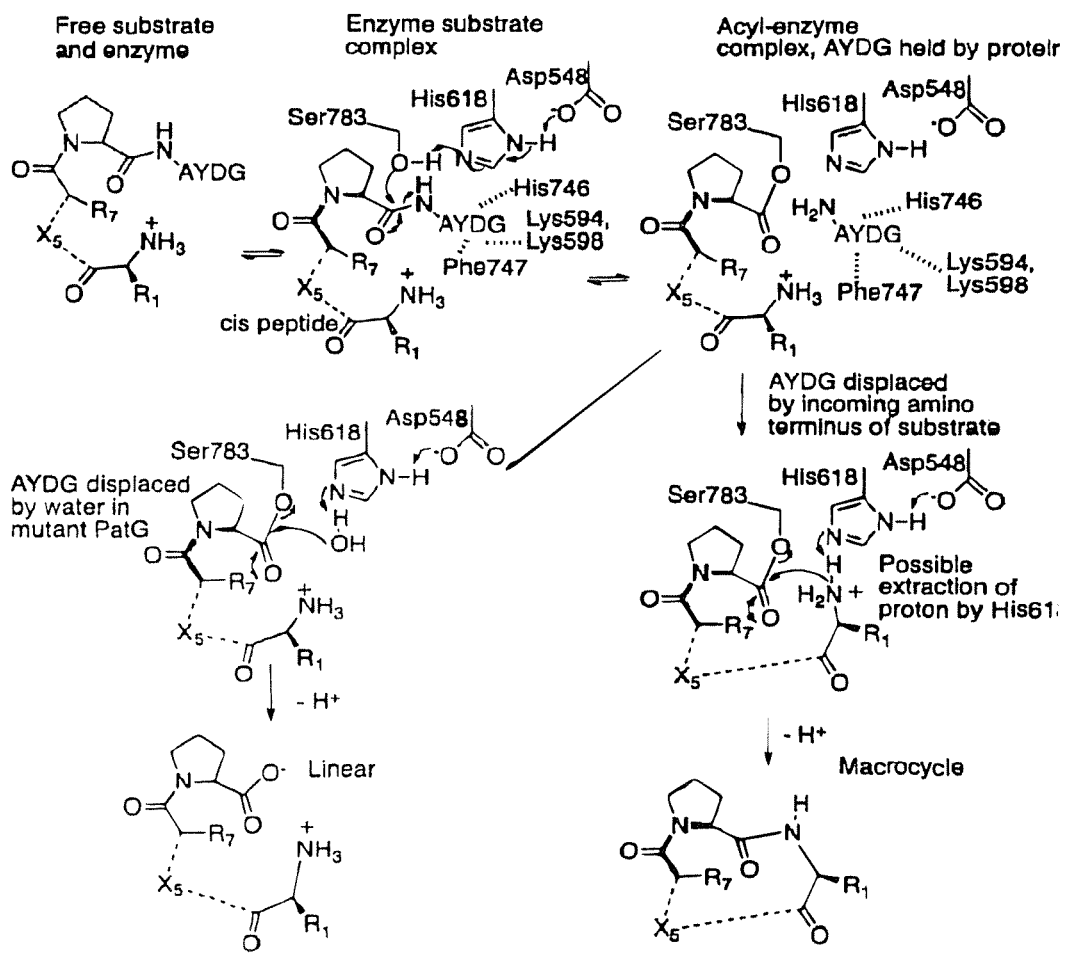

FIG. 17 shows the proposed mechanism for macrocyclization. Model of the acyl-enzyme intermediate with AYDG remaining bound at the active site.

The acyl-enzyme intermediate is in equilibrium with the substrate. In PatGmac the amino terminus of the substrate enters the active site, displacing AYDG and leading to macrocyclization. Mutations that disrupt binding of AYDG lead to linear product, as it is hydrolyzed by water. The role of the His in deprotonating the incoming amino terminus is speculative.

Figure 18:
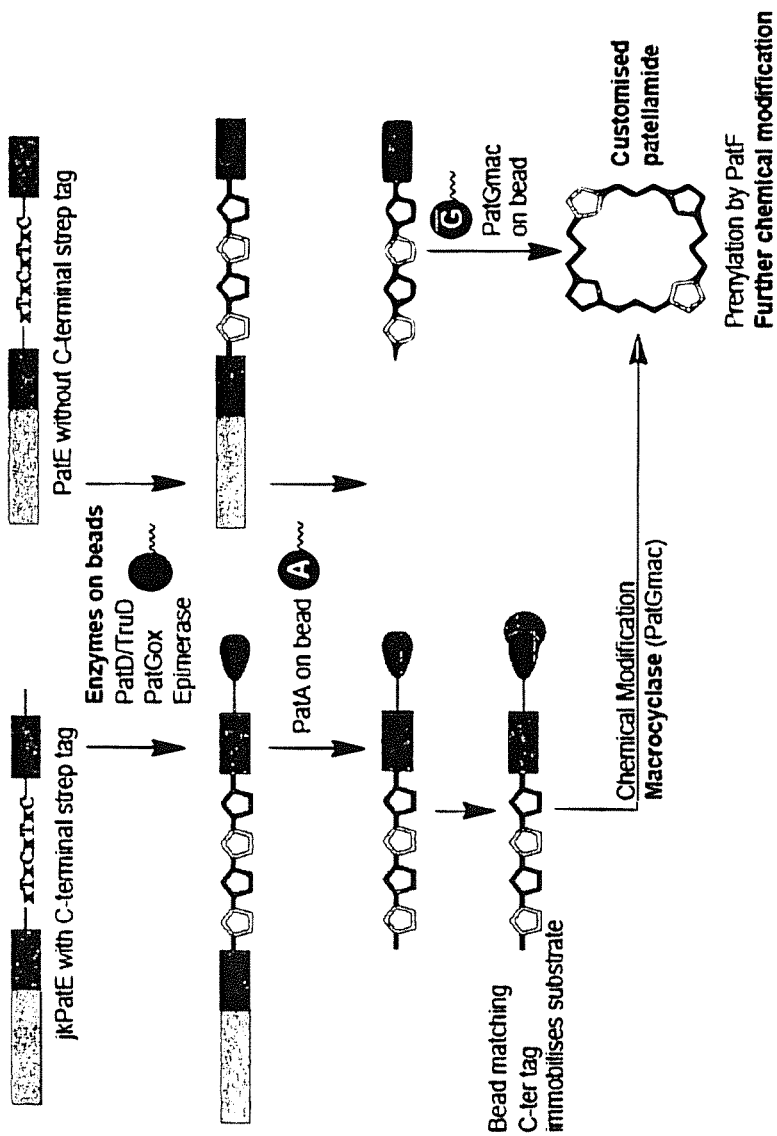

FIG. 18 shows two in vitro systems incorporating PatG macrocyclisation. Tag all enzymes and thus simply remove them at the end of each step. Load the PatA cleaved peptide onto a bead by using C-terminally tagged PatE, and add PatGmac as a soluble enzyme. Both approaches have advantages and disadvantages. The first approach allows valuable enzymes to be recovered and used in excess, but requires purification of the product. The second approach simplifies purification as only the macrocycle and PatG are in solution at the end and further, chemical modification of substrate on a bead will be much easier. The disadvantages are recovery of the macrocyclase enzyme may be impossible in a cost efficient manner and the introduction of a bind step mid process (which would need monitoring).

Figure 19:
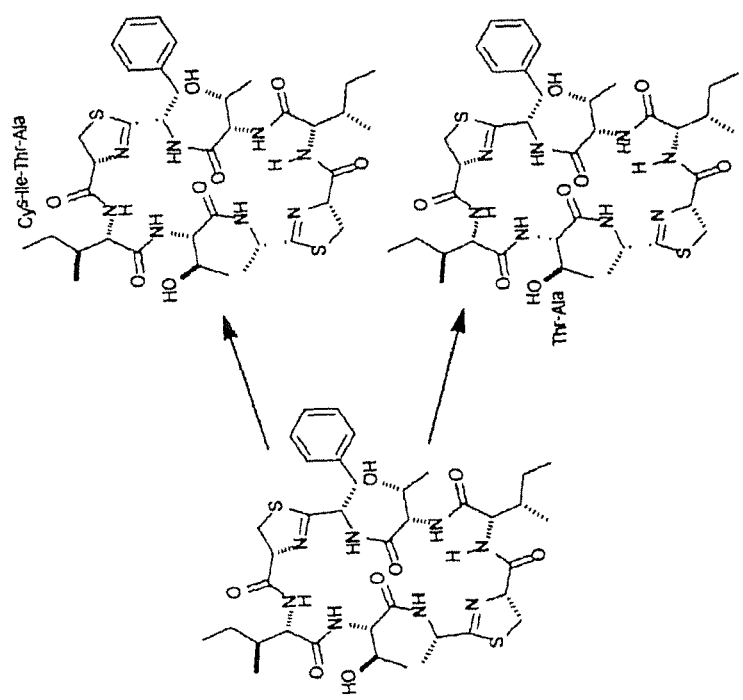

FIG. 19 shows possible MS fragmentation pathways for the cassette ITFCITAC(SEQ ID NO: 74) in the PatE peptide treated with the heterocyclase TruD and macrocyclase PatG to produce cyclo-(ITF(Thn)ITA(Thn)) (SEQ ID NO: 75). The accurate masses of the molecular ion and fragments are consistent with the proposed structure and the MS data shown in Table 3.

Figure 20:
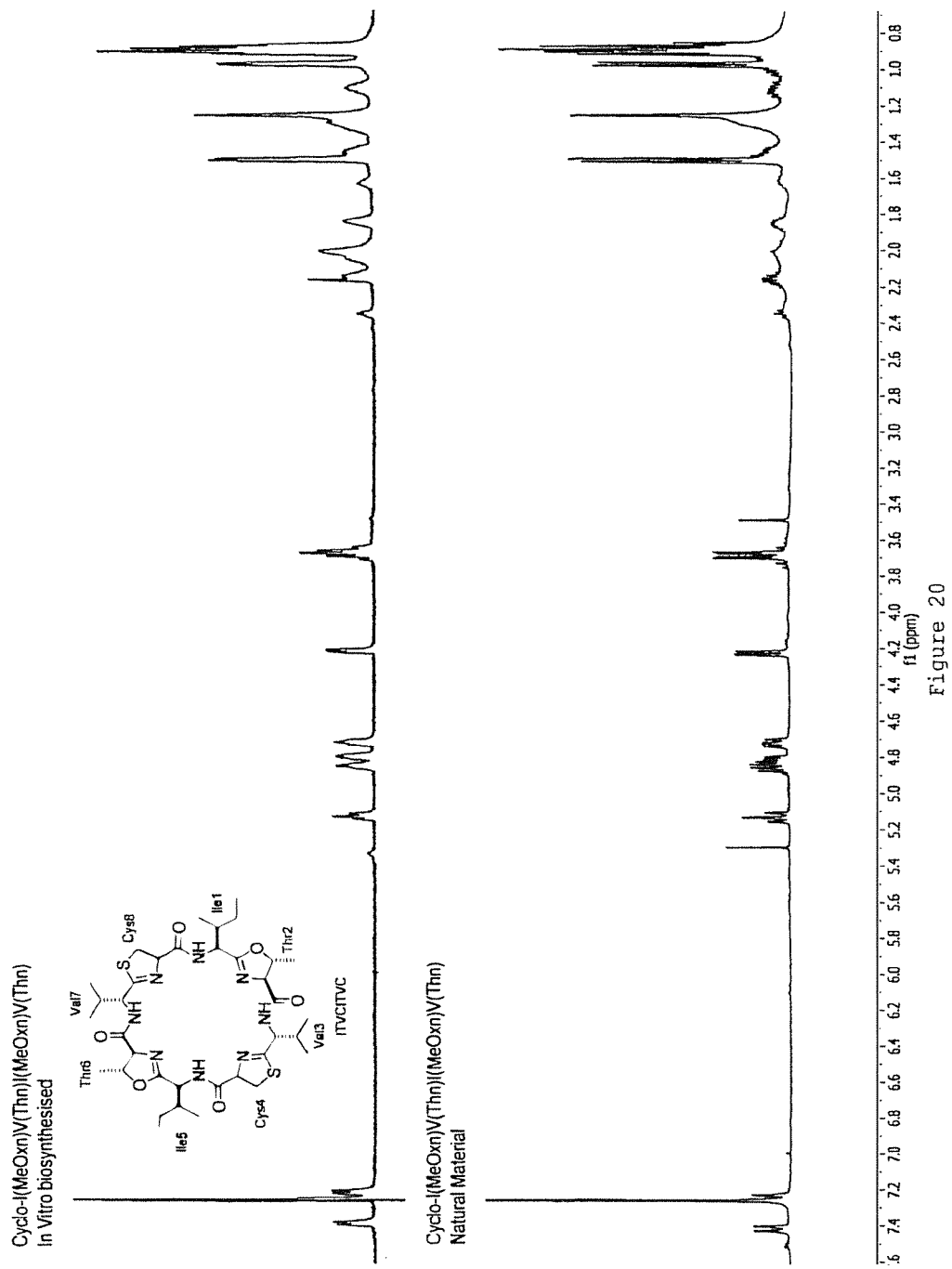

FIG. 20 shows $^1$H NMR of the purified product (cyclo-I(MxOxn)V(Thn)I(MeOxn)V(Thn)) (SEQ ID NO: 76) produced when the cassette ITVCITVC(SEQ ID NO: 30) in the PatE peptide is treated with the heterocyclase PatD and macrocyclase PatG. Structure was confirmed by comparison of the $^1$H NMR to that of the naturally obtained material and by analysis of 2D NMR spectra (Table 7).

Figure 21:
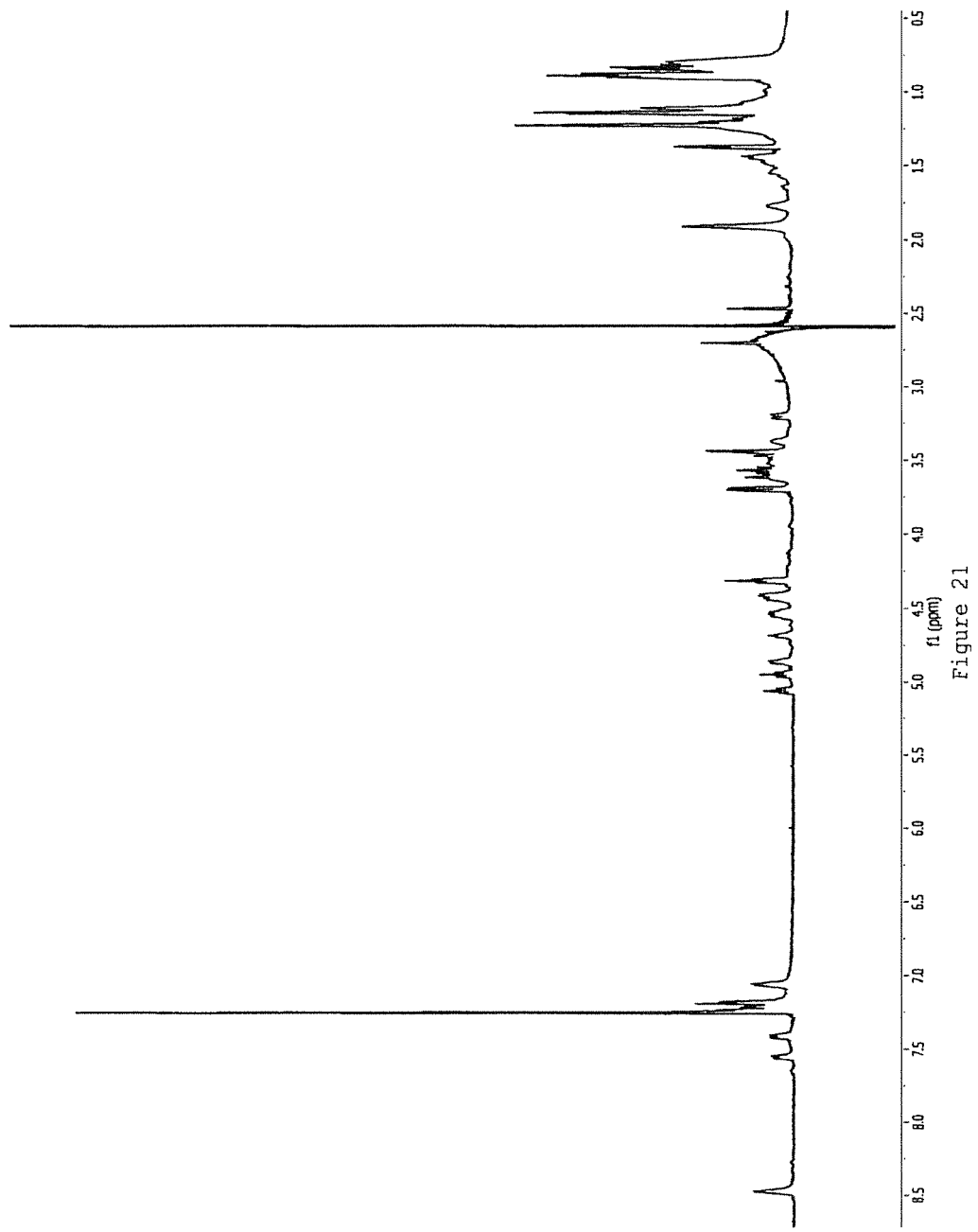

FIG. 21 also shows $^1$H NMR of the purified product (cyclo-(ITA(Thn)ITF(Thn))) (SEQ ID NO: 77) produced when the cassette ITACITFC (SEQ ID NO: 21) in the PatE peptide is treated with the heterocyclase TruD and macrocyclase PatG. The structure was verified by analysis of 2D NMR data (Table 6).

Figure 22:
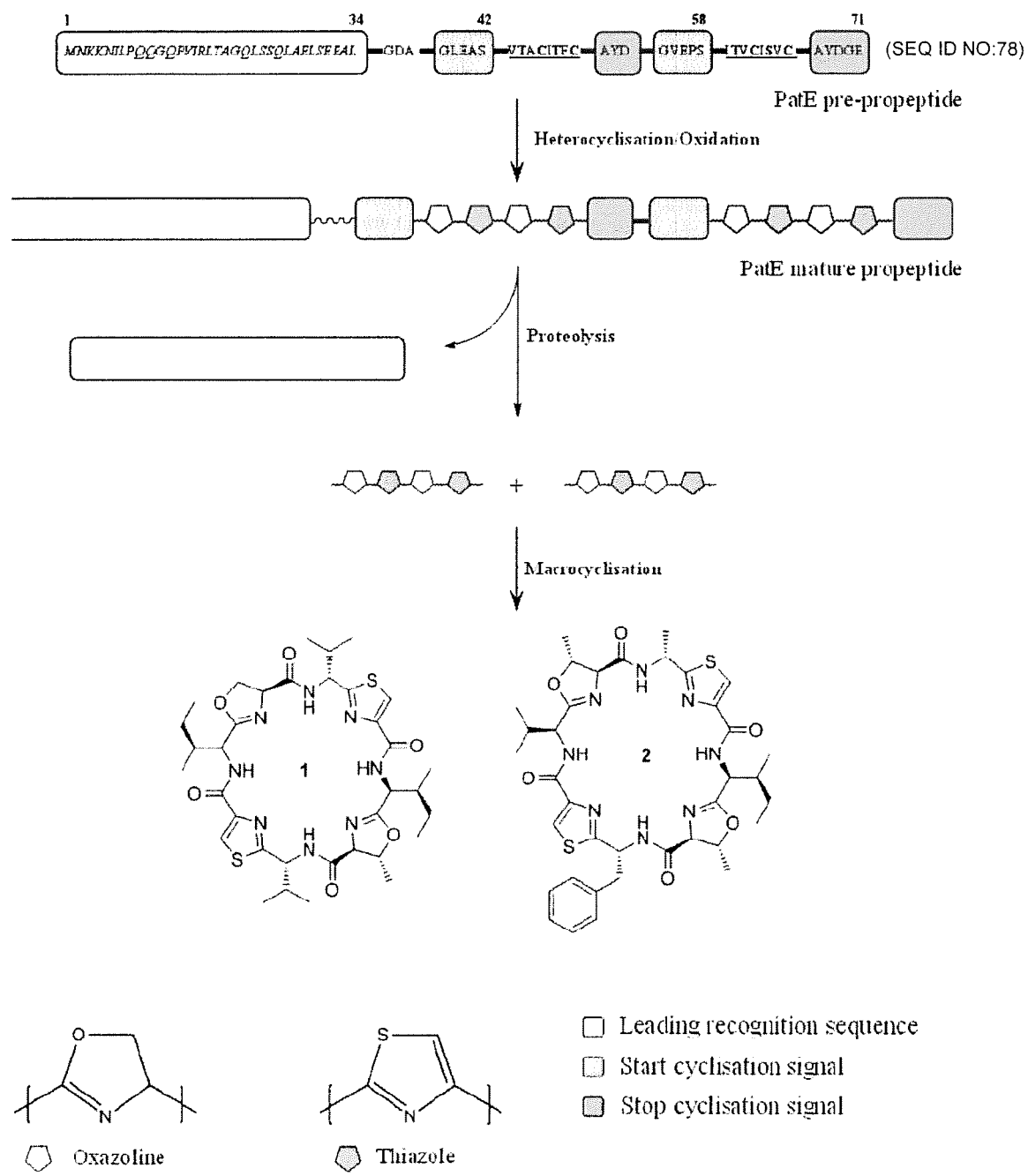

FIG. 22 shows the biosynthetic pathway of patellamides A (1) and C (2). The 71 amino acid structural gene product (PatE pre-propeptide) (SEQ ID NO: 78) is ribosomally synthesised. The tailoring enzymes recognise the N-terminal leader sequence of the PatE pre-propeptide (PatE$_{1-34}$, italic) as well as start/stop cyclisation signals. Four cysteine, three threonine and one serine residues (bold) in the downstream sequence (PatE$_{42-71}$) are post-translationally modified to thiazole and oxazoline heterocycles. Cleavage and macrocyclisation lead to the formation of patellamides A (1) and C (2).

Figure 23:
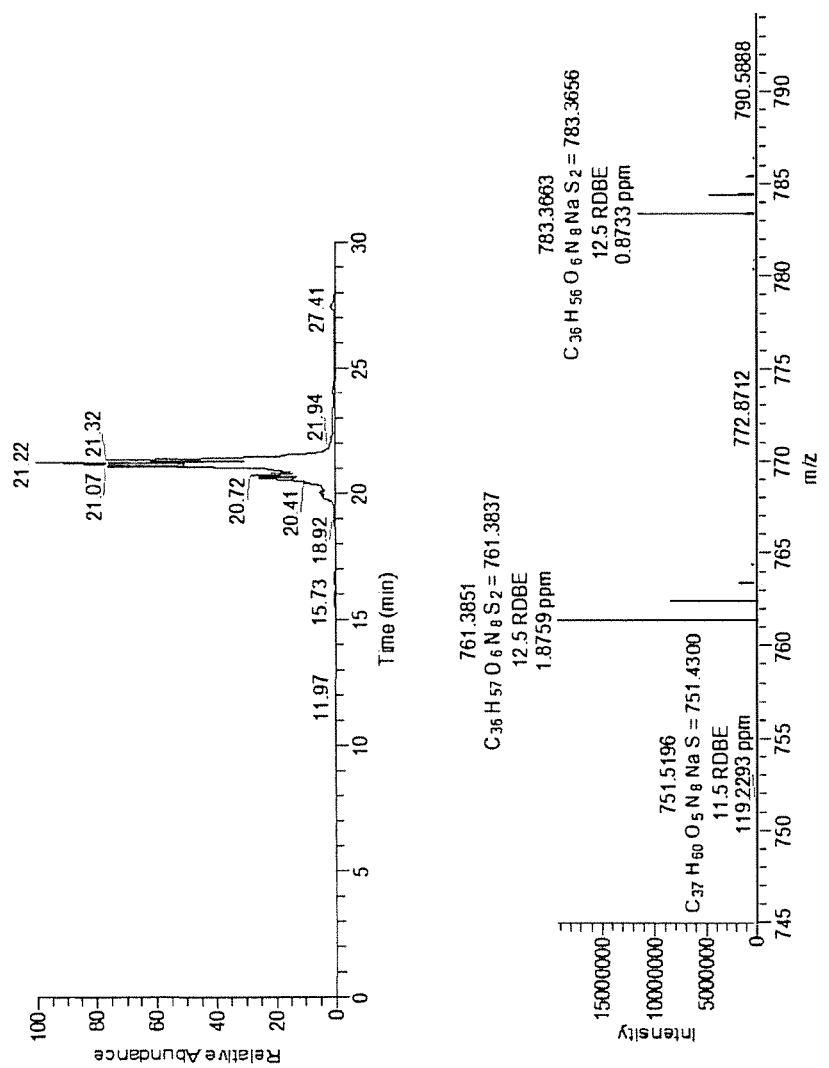

FIG. 23 shows LC-MS of macrocyclized product (cyclo-(ITV(Thn)ITV(Thn)) (SEQ ID NO: 79) produced when the cassette ITVCITVC(SEQ ID NO: 30) in the PatE peptide is treated with the heterocyclase TruD, trypsin and macrocyclase PatGmac.

Figure 24:
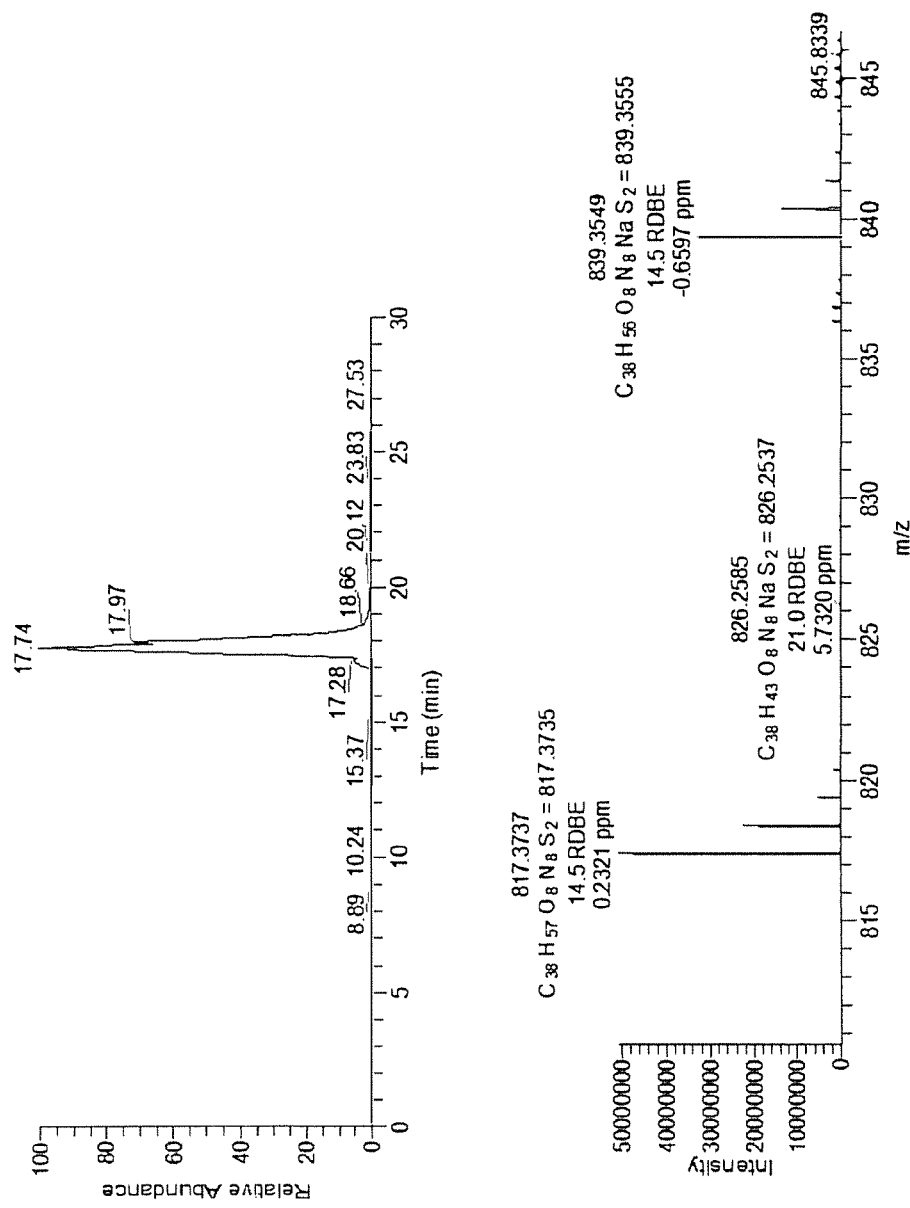

FIG. 24 shows LC-MS of macrocyclized product (cyclo-(ITA(Thn)ITF(Thn)) (SEQ ID NO: 77) produced when the cassette ITACITFC(SEQ ID NO: 21) in the PatE peptide is treated with the heterocyclase TruD, trypsin and macrocyclase PatGmac.

Figure 25:
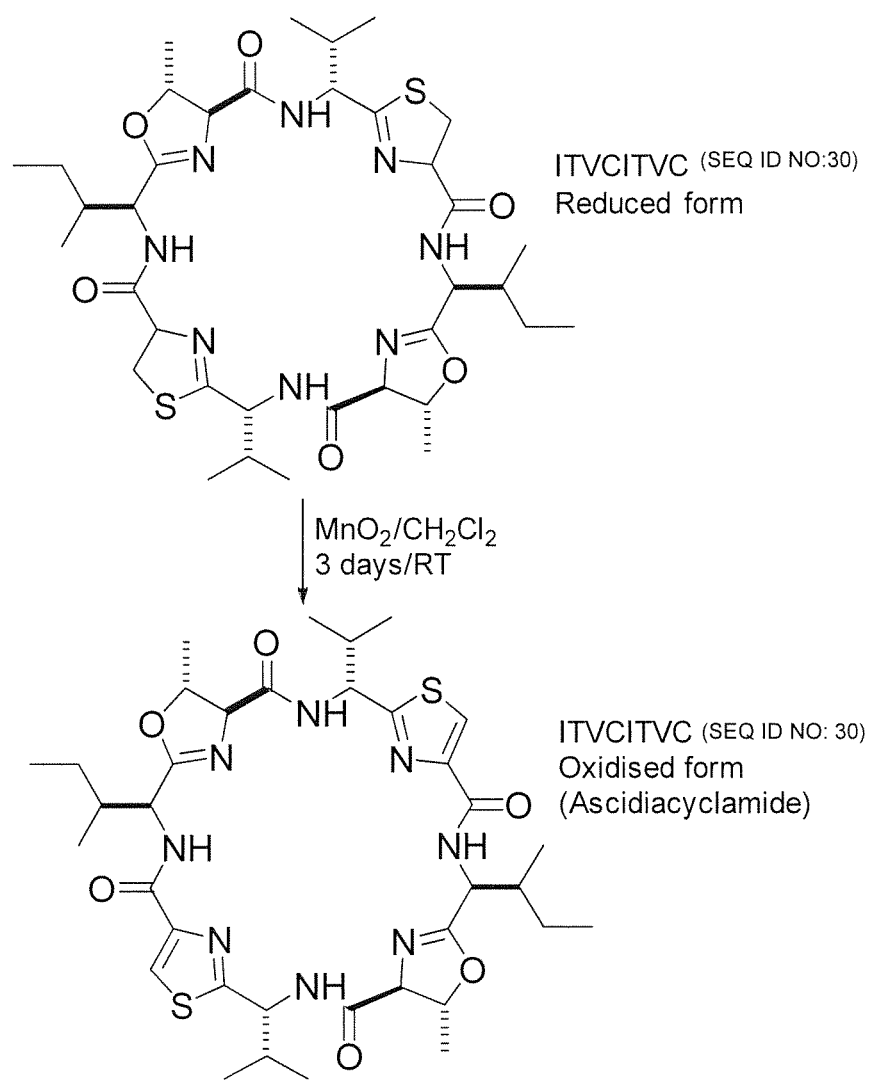

FIG. 25 shows oxidation of cyclo-I(MxOxn)V(Thn)I(MeOxn)V(Thn) (SEQ ID NO: 76).

Figure 26:
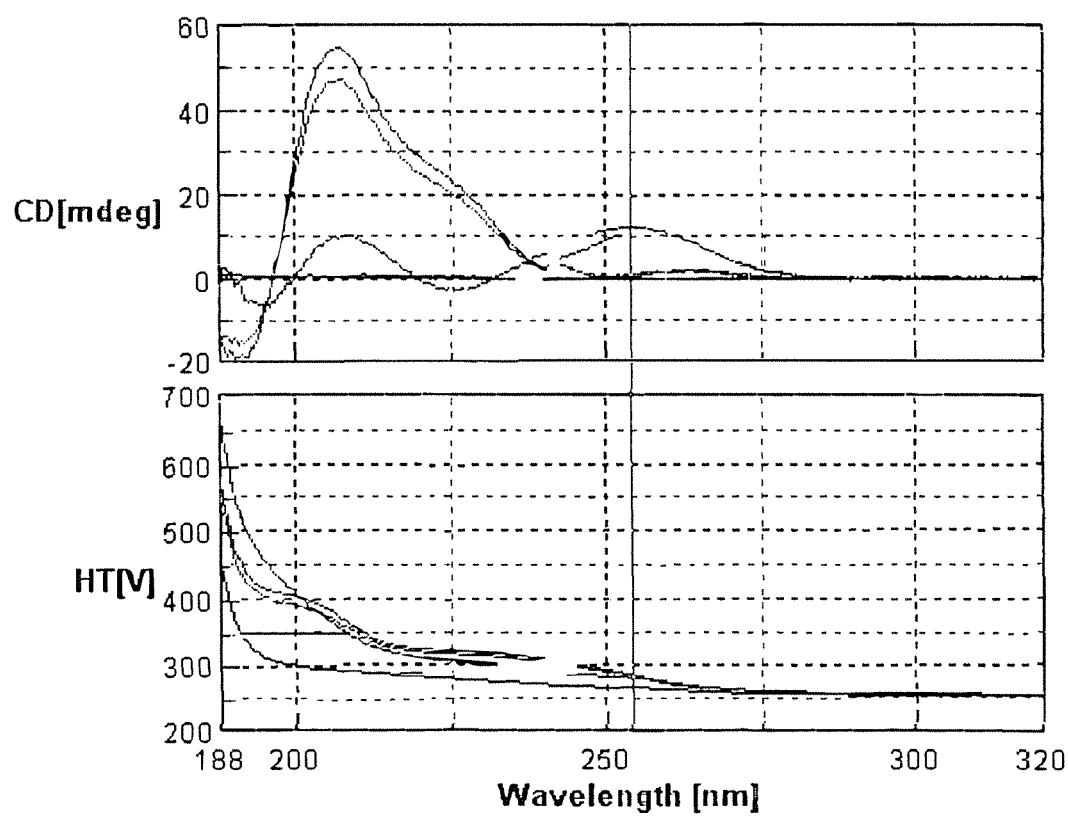

FIG. 26 shows far UV CD spectra of cyclo-I(MxOxn)V(Thn)I(MeOxn)V(Thn) (SEQ ID NO: 76) (reduced) and cyclo-I(MxOxz)V(Thz)I(MeOxz)V(Thz) (SEQ ID NO: 80) (oxidised) produced from the peptide substrate ITVCITVC (SEQ ID NO: 30), and ascidiacyclamide isolated from *Lissoclinum patella* and 100% MeOH. The spectrum of cyclo-I(MxOxz)V(Thz)I(MeOxz)V(Thz) (SEQ ID NO: 80) is shown to correspond to the spectrum of ascidiacyclamide.

Figure 27:
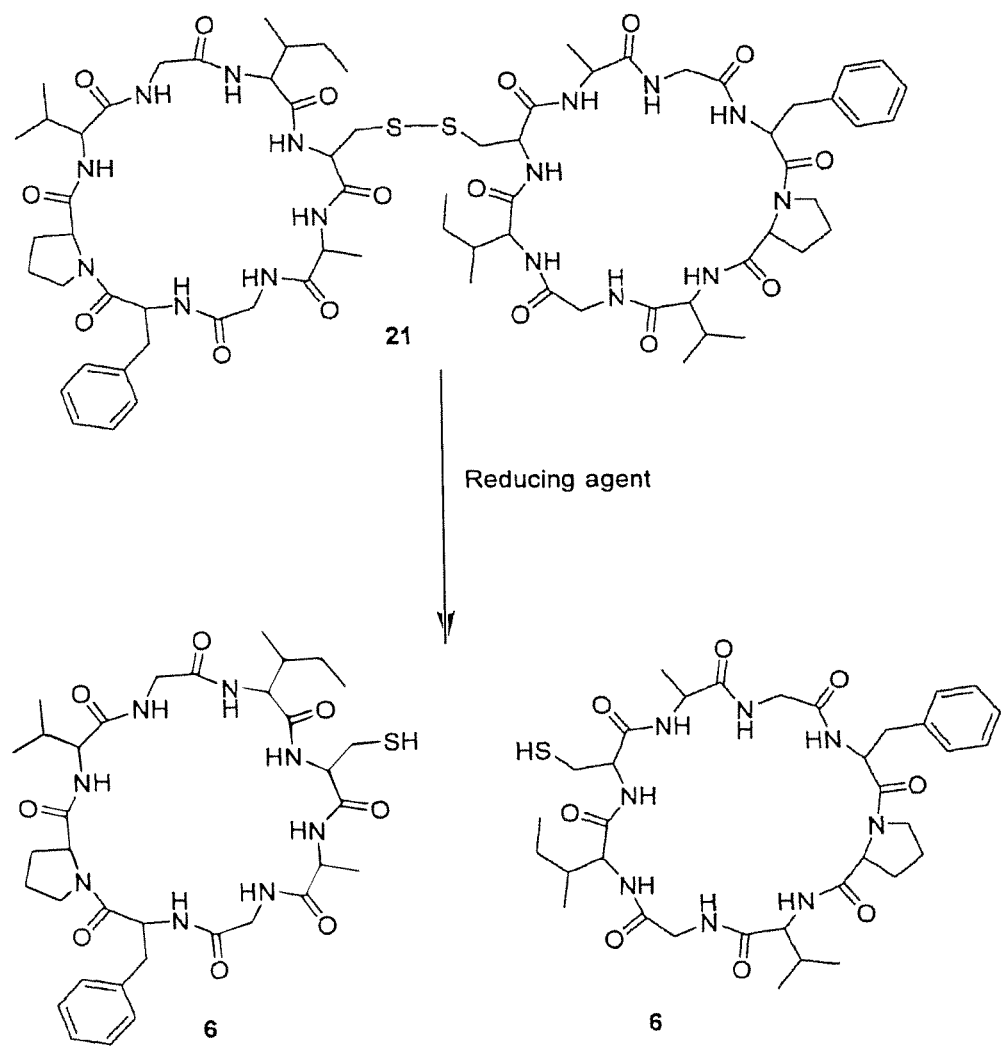

FIG. 27 shows the reduction of cyclic peptide dimer (21) to its monomeric form (6) (SEQ ID NO: 81).

Figure 28:
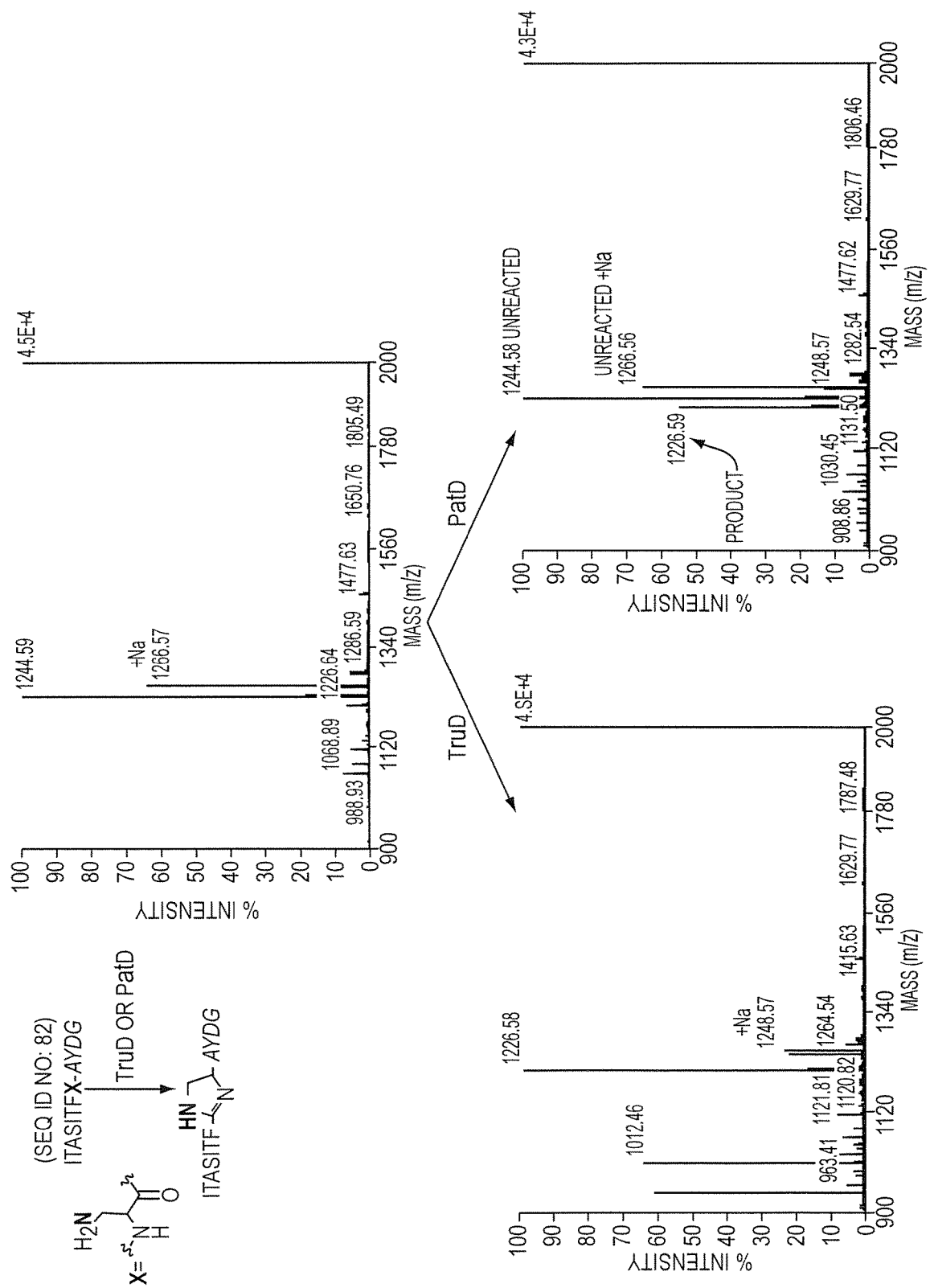

FIG. 28 shows MALDI MS data for the heterocylisation of 2,3-diaminopropanoic acid in the peptide ITASITFXAYDG(SEQ ID NO: 82) (where X is 2,3-diaminopropanoic acid) using TruD or PatD.

Table 1 shows data collection and refinement statistics (molecular replacement) for PatGmac.

Table 2 shows the relative ion counts of linear cleaved and macrocyclized peptide substrate.

Table 3 shows MS data from the cassette ITFCITAC(SEQ ID NO: 74) in the PatE peptide treated with the heterocyclase TruD and macrocyclase PatG. The accurate masses of the molecular ion and fragments shown in this table are consistent with the proposed structure (see FIGS. 19 and 20) and can be explained as outlined on fragmentation pathway shown in FIG. 18.

Table 4 shows cyanobacterial proteases on public databases.

Table 5 shows cyanobacterial heterocyclases on public databases.

Table 6 shows $^1$H/$^{13}$C NMR data in CDCl$_3$ at 600/150 MHz for cyclo-I(MxOxn)V(Thn)I(MeOxn)V(Thn) (SEQ ID NO: 76) obtained from in vitro biosynthesis.

Table 7 shows $^1$H/$^{13}$C NMR data in CDCl$_3$ at 600/150 MHz for cyclo-ITA(Thn)ITF(Thn) (SEQ ID NO: 77) from *Lissoclinum patella* and obtained from in vitro biosynthesis using the peptide substrate ITACITFC (SEQ ID NO: 21).

EXPERIMENTS

Materials and Methods
1. Protein Cloning, Expression and Purification
1.1 Heterocyclases Codon-optimized full length PatD and TruD were cloned into the pJexpress 411 plasmid (DNA2.0 Inc., USA) with an N-terminal His$_6$-tag, with TruD containing an additional Tobacco Etch Virus (TEV) protease cleavage site. Both enzymes are expressed in *Escherichia coli* BL21 (DE3) cells grown on auto-induction medium (Terrific broth base containing trace elements) for 48 h at 20° C. Cells are harvested by centrifugation at 4,000×g, 4° C. for 15 min. Pellets are re-suspended in 500 mM NaCl, 20 mM Tris pH 8.0, 20 mM imidazole and 3 mM BME and supplemented with 0.4 mg DNAse g$^{-1}$ wet cells (Sigma) and complete protease inhibitor tablets (EDTA-free, Roche). Cells are lyzed by passage through a cell disruptor at 30 kPSI or by sonication and the lysates are cleared by centrifugation at 40,000×g, 4° C. for 45 min followed by filtration through 0.4 μm membrane filter. Cleared lysates are applied to a Ni-sepharose FF column (GE Healthcare) pre-washed with lysis buffer and the protein eluted with 250 mM Imidazole. The His$_6$-tag of TruD is removed by addition of 1 mg TEV protease per 10 mg TruD incubated at room temperature for 2 hours and the cleaved protein isolated by passage through a second Ni-sepharose FF column. (Note: TruD still functions efficiently if His$_6$-tag is not removed). Both enzymes are then loaded on to a Superdex 200 gel filtration column (GE Healthcare), pre-equilibrated and run in 150 mM NaCl, 10 mM HEPES pH 7.4, 1 mM TCEP. Peak fractions were pooled and the proteins concentrated to 100 μM for use in in vitro reactions.

1.2 Macrocyclases

PatGmac (PatG residues 492-851) was cloned from genomic DNA (*Prochloron* sp.) into the pHISTEV vector (Liu, H. & Naismith, J. H 2009) and expressed in *Escherichia coli* BL21 (DE3) grown on autoinduction medium (Terrific broth base containing trace elements; Studier, F. W., 2005) for 48 h at 20° C.

Cells were harvested by centrifugation at 4,000×g, 20° C. for 15 min and resuspended in lysis buffer (500 mM NaCl, 20 mM Tris pH 8.0, 20 mM Imidazole and 3 mM β-mercaptoethanol (BME)) with the addition of complete EDTA-free protease inhibitor tablets (Roche) and 0.4 mg DNase g wet cells (Sigma). Cells were lysed by passage through a cell disruptor at 30 kPSI (Constant Systems Ltd), or by sonication, and the lysate was cleared by centrifugation at 40,000× g, 4° C. for 45 min followed by filtration through 0.4 μm membrane filter. Cleared lysate was applied to a Ni-NTA (Qiagen) column or a Ni-sepharose FF column (GE Healthcare) pre-washed with lysis buffer and protein eluted with 250 mM imidazole.

In some methods, the protein was then passed over a desalting column (Desalt 16/10, GE Healthcare) in 100 mM NaCl, 20 mM Tris pH 8.0, 20 mM imidazole, 3 mM μm. Tobacco etch virus (TEV) protease was added to the protein at a mass-to-mass ratio of 1:10 and the protein digested for 1 h at 20° C. to remove the His-tag. Digested protein was passed over a second Ni-column and the flow-through loaded onto a monoQ column (GE Healthcare) equilibrated in 100 mM NaCl, 20 mM Tris pH 8.0, 3 mM BME. Protein was eluted from the monoQ column through a linear NaCl gradient, eluting at 350 mM NaCl. Finally, the protein was subjected to size-exclusion chromatography (Superdex™ 75, GE Healthcare) in 150 mM NaCl, 20 mM Tris pH 8.0, 3 mM μm, and concentrated to 60 mg mL$^{-1}$.

In other methods, the protein was then passed over Superdex 75, GE Healthcare in 150 mM NaCl, 10 mM HEPES pH 7.4, 1 mM TCEP and concentrated to 1 mM.

All PatGmac point mutants were produced using the Phusion® site-directed mutagenesis kit (Finnzymes) following the manufacturer's protocol, while the lid deletion mutants were made with fusion PCR. All mutant proteins were expressed and purified as above.

1.3 Precursor Peptides

Variants of PatE, each encoding only one core peptide instead of two tandem patellamide core peptides, was cloned with a C-terminal His$_6$-tag into pBMS233 for easier analysis of processed products. To enable more efficient N-terminal cleavage, additional residues were in some cases added directly before the core peptide to allow for cleavage by either trypsin (K/R) or TEV (ENLYFQ) (SEQ ID NO: 83). The protein was expressed in BL21(DE3) cells grown on auto-induction medium (Terrific broth base containing trace elements) at 37° C. overnight. Cells were harvested by centrifugation at 4,000×g, 20° C., for 15 min and re-suspended in 8 M urea, 500 mM NaCl, 20 mM Tris pH 8.0, 20 mM imidazole and 3 mM BME. Cells were lysed by sonication, and the lysate waas cleared by centrifugation at 40,000×g, 20° C. for 45 min followed by filtration through 5, 0.8 and 0.4 μm membrane filters respectively. Cleared lysate was applied to a Ni-sepharose FF column (GE Healthcare) column prewashed with lysis buffer, and protein was eluted with 250 mM imidazole. DDT is added to the eluted PatE to a final concentration of 10 mM and the solution was incubated at room temperature for 3 hours. PatE is further purified and separated from protein aggregates by size-exclusion chromatography (Superdex 75, GE Healthcare) in 150 mM NaCl, 10 mM HEPES pH 7.4, 1 mM TCEP and concentrated to 1 mM.

2. Heterocyclization Reactions

Hetrocyclization reactions contained 100 μM PatE, 5 μM TruD/PatD, 5 mM ATP pH 7, 5 mM MgCl$_2$, 150 mM NaCl, 10 mM HEPES, pH 7.4, 1 mM TCEP. Reactions were incubated at 37° C. with shaking at 200 rpm for 24 h when using TruD and 48 h for PatD. In some cases, the PatE showed a degree of precipitation. In these instances the peptide was recovered from the precipitate by denaturation in 8M urea as above followed by Ni affinity chromatography and size-exclusion. Reactions were monitored by MALDI.

Processed PatE was purified on Superdex 75, GE Healthcare in 150 mM NaCl, 10 mM HEPES pH 7.4, 1 mM TCEP and concentrated.

3. Macrocyclization Reactions

For macrocyclization reactions comparing final product ratios after substrate depletion, 100 μM peptide (VGAGIG-FPAYDG) (SEQ ID NO: 68) was incubated with 50 μM enzyme in 150 mM NaCl, 10 mM HEPES pH 8, 1 mM TCEP for 120 h at 37° C. Samples were analyzed by ESI or MALDI MS (LCT, Micromass or 4800 MALDI TOF/TOF Analyser, ABSciex).

Figure 1A:
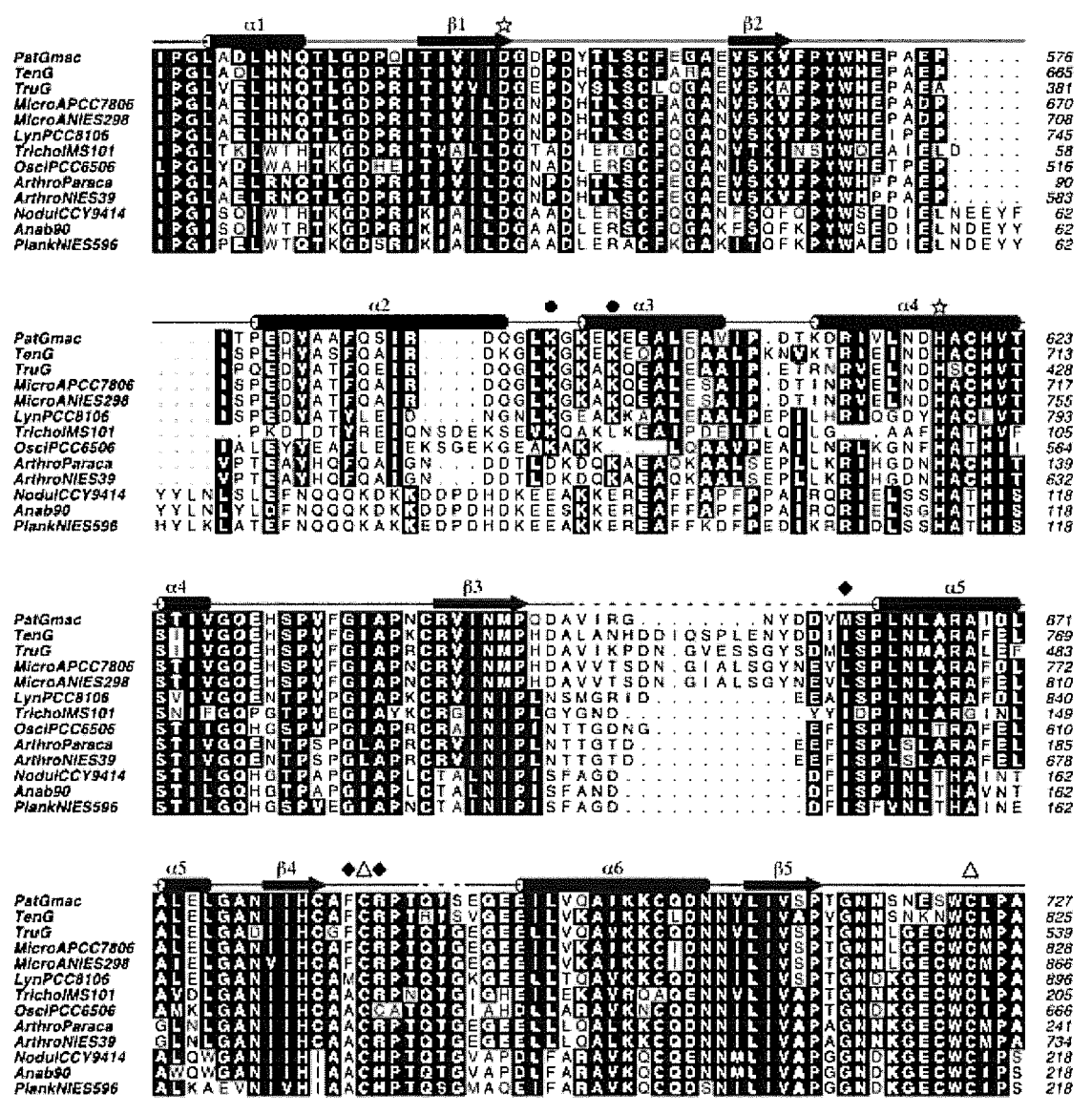
Figure 1B:
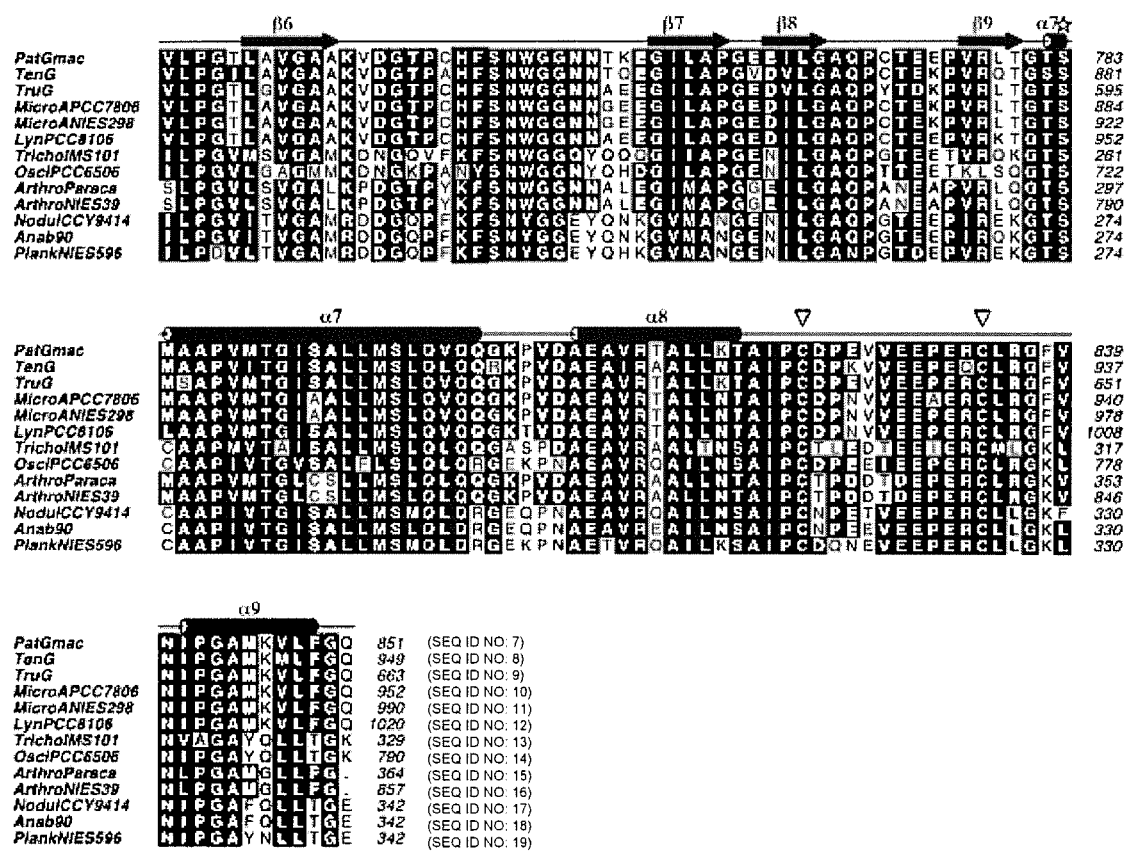

For other macrocyclization reactions, 100 μM peptide (e.g. VGAGIGFPAYDG (SEQ ID NO: 68), VGAGIGF-PAYRG (SEQ ID NO: 69), or GVAGIGFPAYRG (SEQ ID NO: 84)) was incubated with 20 μM enzyme in a range of buffers for 24 h at 37° C. (see FIGS. 1 to 3).

Other macrocyclization reactions contained 100 μM peptide (PatE), 5% DMSO, 350 mM NaCl, 20 μM PatGmac, 150 mM NaCl and 20 mM Bicine pH 8.0 were incubated at 37° C. with shaking at 200 rpm for 4 days and monitored by MS.

4. LC-MS Analysis of Products

LC-MS was performed using a Phenomenex Sunfire C18 column (4.6 mm×150 mm). Solvent A was H$_2$O containing 0.1% formic acid and solvent B was MeOH containing 0.1% formic acid. Gradient: 0-2 min 10% B; 2-22 min 10% B to 100% B; 22-27 min 100% B; 27-30 min 100% B to 10% B. High resolution mass spectral data were obtained from a Thermo Instruments MS system (LTQ XL/LTQ Orbitrap Discovery) coupled to a Thermo Instruments HPLC system (Accela PDA detector, Accela PDA autosampler and Accela Pump). The following conditions were used: capillary voltage 45 V, capillary temperature 320° C., auxiliary gas flow rate 10-20 arbitrary units, sheath gas flow rate 40-50 arbitrary units, spray voltage 4.5 kV, mass range 100-2000 amu (maximum resolution 30000).

5. Crystallization, Data Collection, and Crystallographic Analysis

Crystals of PatGmac were obtained in 19% PEG6000, 0.07 M calcium acetate, 0.1 M Tris pH 9.0. The crystals were cryoprotected in 30% glycerol and flash-cooled in liquid nitrogen. These crystals belonged to space group C2 with cell dimensions a=132.1 Å, b=67.6 Å, c=97.3 Å, β=115.0°.

Crystals of PatGmac with peptide were obtained from a mixture of PatGmac with peptide (VPAPIPFPAYDG, (SEQ ID NO: 85) 1:4 molar ratio) in 1.2 M sodium citrate, 0.1 M sodium cacodylate pH 7.0. There was electron density for a peptide at one active site but the quality of the map was poor. We reasoned this was due to low occupancy of the peptide and therefore soaked the complex crystals overnight in 7.5 mM peptide prior to data collection. These crystals belonged to space group C2 with a=135.6 Å, b=67.3 Å, c=137.9 Å, p=116.8°. Diffraction data of both structures were collected in-house, each on a single crystal at 100 K on a Rigaku 007HFM rotating anode X-ray generator with a Saturn 944 CCD detector and processed with xia2 (Winter, G., 2009).

The structure of PatGmac was solved by molecular replacement with PHASER (Storoni, L. C., McCoy, A. J. & Read, R. J., 2004; McCoy, A. J., Grosse-Kunstleve, R. W., Storoni, L. C. & Read, R. J., 2005) using the structure of AkP (PDB entry 1DBI) as the search model, followed by automatic rebuilding with Phenix (Adams, P. D. et al., 2004). The structure of PatGmac with peptide was solved by molecular replacement using the PatGmac structure as the search model. Manual rebuilding was performed with COOT (Emsley, P. & Cowtan, K. Coot, 2004) and refinement was performed using REFMAC5 (Murshudov, G. N., Vagin, A. A. & Dodson, E. J., 1997) implemented in the CCP4 program suite (*Acta Crystallographica Section D* 50, 760-763 (1994). The statistics of data collection and refinement are summarized in Table 1. Molecular graphics figures were generated with the program Pymol (DeLano Scientific, LLC).

6. Synthesis of the Peptide Substrates

Fmoc amino acid derivatives, 2-(1H-benzotriazol-1-yl)-1,1,3,3-tetramethyluronium hexafluorophosphate (HBTU) and Fmoc-Gly-NovaSyn® TGT resin were purchased from Novabiochem®, Merck Biosciences, UK. Trifluoroacetic acid (TFA), N,N-diisopropylethylamine (DIEA), N,N-dimethylformamide (DMF), and piperidine were obtained from Sigma-Aldrich, UK and used without further purification.

The peptides, including VGAGIGFPAYDG (SEQ ID NO: 68), VPAPIPFPAYDG (SEQ ID NO: 85), and GVAGIGFPAYRG (SEQ ID NO: 84), were synthesized manually using the standard Fmoc-based strategy (Cammish, L. E. & Kates, S. A., 2000). Amino acids were sequentially coupled after removal of the Fmoc blocking group at each cycle. Fmoc deprotection steps were carried out with 20% piperidine in DMF (v/v) for 12 min while coupling reactions were performed in DMF using a molar ratio of amino acid:HBTU:DIEA:resin of 5:5:10:1. Reactions were monitored using the Kaiser test.

The peptides were cleaved from the support and deprotected by treatment with a mixture consisting of 95% TFA, 2.5% triisopropylsilane (TIPS), and 2.5% $H_2O$ (20 mL of mixture $g^{-1}$ of peptide resin, 3 h at room temperature).

The resin was then filtered and washed with TFA. The combined filtrates were concentrated under reduced pressure. The peptide was precipitated with cold diethyl ether and recovered by centrifugation. The peptide sequence was verified by MSMS analysis.

The peptide VGAGIGFPAYRG (SEQ ID NO: 68) was purchased from Peptide Protein Research Ltd.

7. Proteolytic Cleavage

Different proteases were used, including trypsin and TEV protease, depending on the PatE sequence created. We use 4 µg of trypsin per 1 mg of purified processed PatE. The corresponding figure for TEV protease is 1 mg for each 10 mg of PatE. Reactions were incubated at 37° C. with shaking at 200 rpm for up to 4 hours. Reaction products are purified using Superdex 30, GE Healthcare in 150 mM NaCl, 20 mM Bicine pH 8.0. The purified product was concentrated using on Phenomenex® Strata C18-E, 55 µm, 70 Å, 2 g/12 mL Giga SPE tube cartridges. After loading the sample, a washing step with deionised water to get rid of buffer salts was carried out and this was followed by elution step with 5× column volume methanol and 5× column volume of acetonitrile. We also washed the column with 5× volume of 0.1% TFA in acetonitrile. Washings with water or acidified acetonitrile were tested separately by MS for all peptides. Peptides were found to be eluted completely with the organic solvents.

8. Purification of Patellamides

Macrocyclisation reactions were concentrated on Phenomenex® Strata C18-E, 55 µm, 70 Å, 2 g/12 mL Giga SPE tube cartridges following the above procedure. This was followed by final purification of the products using HPLC on C4 ACE column 10×250 mm, 5 µm and using a gradient of acetonitrile in water. Water was dionised standard while methanol and acetonitrile are both LCMS standards. All glassware was soaked with 1.0 molar nitric acid (12 hours) and rinsed with deionised water and air or oven dried. Purification process was monitored using DAD at wavelengths of 210, 220, 230, 240 and 254 nm.

Structures of the purified products were confirmed using NMR and MS. NMR data for two compounds obtained was tabulated (Tables 7 and 8). Purified compounds were chemically oxidised using $MnO_2$ in dichloromethane for three days at 28° C.

Results

Example 1: Overall Structure of the PatG Macrocyclase Domain

The macrocyclase domain of PatG (PatGmac, residues 492-851) was overexpressed in *E. coli* BL21 (DE3) cells and purified using established protocols (Liu, H. & Naismith, J. H., 2009) The retention profile from gel filtration indicated that the domain was a monomer.

The protein formed crystals belonging to the space group C2, with two biological monomers in the asymmetric unit. The structure was determined at 2.19 Å resolution by molecular replacement using the subtilisin *Bacillus* Ak.1 protease (AkP) (PDB entry 1DBI) as a search model. Table 1 shows the data collection and refinement statistics. The refined model (PDB entry 4AKS) includes residues 514-653, 659-685, 694-717, 728-745, 754-822, and 835-851 in chain A, and 515-650, 660-688, and 692-850 in chain B. The missing residues are in loops and at the N-terminus and are presumed to be disordered.

PatGmac has a spherical shape with dimensions of approximately 53 Å×42 Å×48 Å. The protein contains a seven-stranded parallel β-sheet with two α helices on each face, a fold common to all subtilisin-like proteases. However, the conserved metal ion of subtilisin-like proteases is not present in PatGmac as the binding site is destroyed by sequence changes.

PatGmac contains a catalytic triad consisting of Asp548 located at the C-terminus of the β-strand β1, His618 in the middle of α4 and Ser783 at the N-terminus of α7. The carboxyl group of Asp548 is hydrogen bonded to the side-chain of His618 (2.9 Å), which is in turn hydrogen bonded to the side-chain of Ser783 (2.7 Å). PatGmac has an insertion that extends from β2 as a loop, then forms a helix-loop-helix motif and creates an N-terminal extension of α4, the helix that harbors His618. The insertion is found in other macrocyclases but is not conserved in length or sequence.

Example 2: Comparison of Subtilisin-Like Protease AkP and PatGmac

The amino acid sequences of the AkP and PatGmac are 28% identical and pairwise superposition gives a Cα rmsd of 1.23 Å over 145 structurally equivalent residues. The most striking difference is that PatGmac contains a helix-turn-helix insertion between α2 and α4 (A574 to K610) that sits above the active site; we denote this as the macrocyclization insertion. Eight of these residues form a two turn N-terminal extension of α4 when compared to the typical subtilisin structure. This results in the catalytic His being in the middle of this helix rather than at the end. The other 29 residues form a helix-turn-helix motif.

Four cysteines, which are highly conserved in PatG and its homologs (FIGS. 1A and 1B), make two disulfide bonds: Cys685/724 and Cys823/834. The Cys685/724 disulfide bond in PatGmac is different from that seen in subtilisins.

Cys137 of AkP is equivalent to Cys685 of PatGmac and it forms an intraloop disulfide bond with Cys139, making an 11-atom ring that is proposed to rigidify the active site.

In contrast, PatGmac Cys685/724 bridges two loops, one of which connects α4 to α6 adjacent to the active site. As a result Phe684 and Arg686 pack against the side-chain of Met660, completely filling the S4 and S3 substrate binding pockets. Cys823/834 links the ends of the loop that connects α8 to α9 at the C-terminus of the domain and is distant from the active site.

Example 3: PatGmac Substrate Complex

The VPAPIPFPAYDG (SEQ ID NO: 85) peptide was chosen to match the residues equivalent to P8-P4', the eight-residue cassette and four C-terminal residue macrocyclization signature. The proline residues were chosen to mimic the heterocycles of the natural substrate and the peptide can in fact be macrocyclized by PatGmac (albeit slowly).

The structure of the complex of PatGmacH618A (inactive mutant) was determined at 2.63 Å by molecular replacement using PatGmac native as a search model (Table 1). The difference electron density for bound peptide in the active site of one promoter was unambiguous for PIPFPAYDG (SEQ ID NO: 86) (P5 to P4') and showed that three N-terminal residues (VPA) of the substrate mimic are disordered. The refined model (PDB entry 4AKT) contains residues 514-686, 694-719, 727-747, 754-823, and 833-851 in chain A, and 515-651, 657-688, and 692-851 in chain B.

Residues P5 and P4 of the substrate (Pro and Ile) make no contact with the protein while P3 (Pro) has weak van der Waals interactions with Tyr210. P2 (Phe) also makes limited van der Waals contacts and the side chain sits in a shallow pocket. The Pro of P1 adopts a cis peptide conformation that results in the substrate pointing away from the protein and the side-chain makes van der Waals contacts with His618Ala and Val622. The carbonyl of the P1-P1' peptide is 4.3 Å from and correctly oriented for nucleophilic attack by the hydroxyl of Ser783. The side-chain of Met784 sits on this face of the carbonyl while the side-chain of the absolutely conserved Asn717 points towards the opposite face in the correct position to stabilize the tetrahedral intermediate. The P1' Ala Ca and side-chain make only a few hydrophobic interactions, including contacts with Met784 and the protein backbone. It sits in a cavity that appears to be large enough for bulkier residues. The P2' (Tyr) residue makes extensive contacts with the protein: a n-stacking interaction with the highly conserved Phe747, a hydrogen bond to His746 (conserved as His or Lys in homologs) and a hydrogen bond between the Tyr main-chain oxygen and the nitrogen of Thr780. The side-chain of P3' (Asp) is oriented towards a large electropositive patch created by Arg589, Lys594, and Lys598. It makes a salt bridge with Lys598 and possibly Lys594, though the side chain of Lys594 is not well ordered. The P4' Gly residue makes no contact with the protein, although the terminal carboxyl group is close to Lys594. The binding of the peptide is accompanied by changes in PatGmac at Phe684, as the main chain moves 2 Å at the Ca position to avoid a clash with the substrate. The side chains of Met660, Phe684 and Arg686 prevent the binding of substrates that adopt an extended conformation.

The active site where the acyl-enzyme intermediate would be formed is shielded from solvent by the macrocyclization insertion and the AYDG peptide.

During macrocyclization, the acyl-enzyme intermediate is in equilibrium with the substrate. In PatGmac, the amino terminus of the substrate enters the active site, displacing AYDG (SEQ ID NO: 20) and leading to macrocyclization. Mutations that disrupt binding of AYDG (SEQ ID NO: 20) lead to linear product, as it is hydrolyzed by water. The role of the His in deprotonating the incoming amino terminus is speculative.

Example 4: Biochemical Characterization of Macrocyclization

The peptide VGAGIGFPAYDG (SEQ ID NO: 68) was used as a substrate for PatGmac in biochemical assays (FIG. 4C[[c]]). The ratio of macrocyclized to linear product using this substrate peptide was determined by ion counts obtained from liquid chromatography-electrospray ionization mass spectrometry (LC-ESI MS). For native protein only macrocyclized product (cyclo[VGAGIGFP] (SEQ ID NO: 70)) was detected (Table 2, FIGS. 5-10).

Figure 1C:
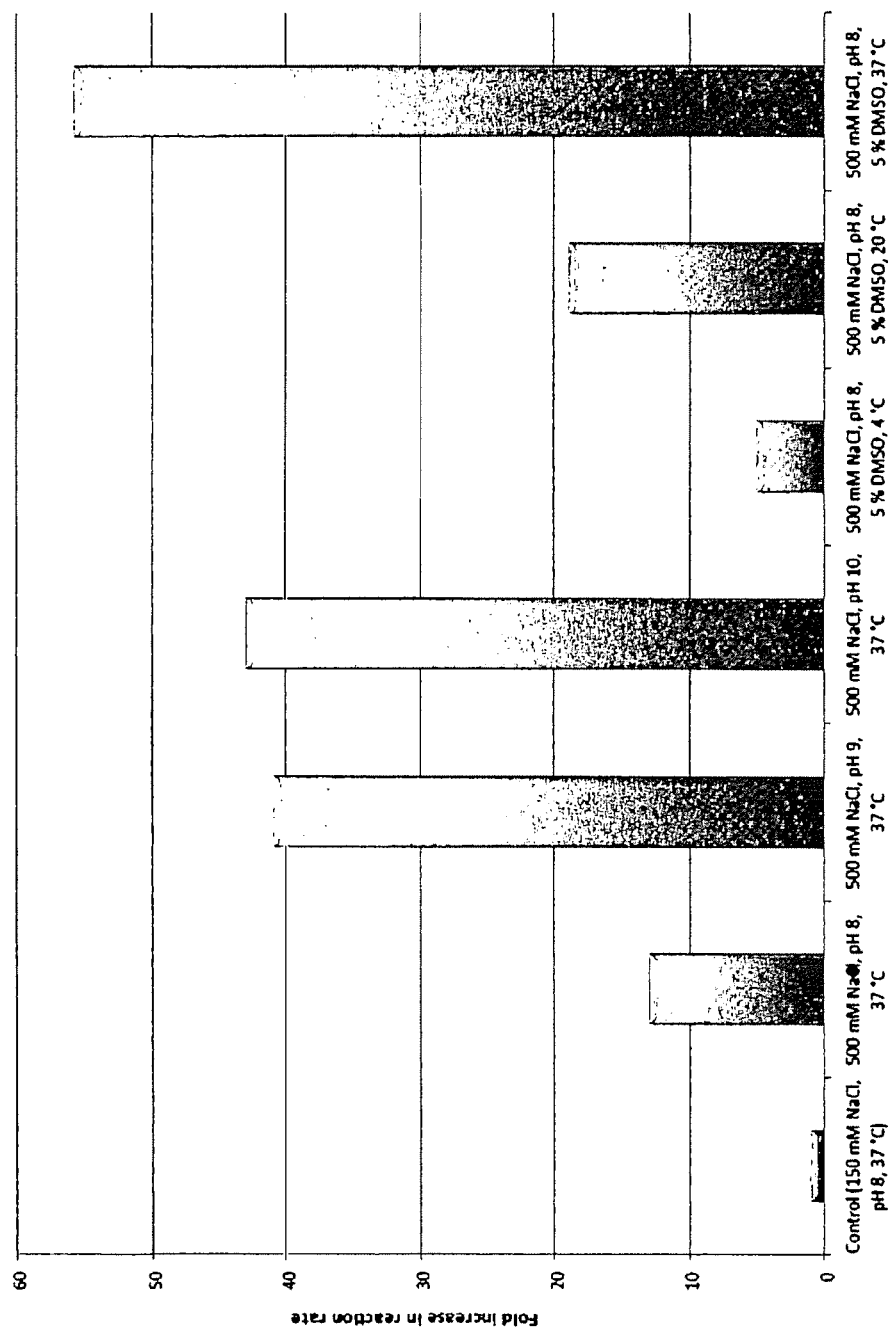

PatGmac is a slow enzyme; turnover rates reported to date are ~1 per day (Lee, J., McIntosh, J., Hathaway, B. J. & Schmidt, E. W., 2009; McIntosh, J. A. et al., 2010). Increasing the sodium chloride concentration from 150 mM to 500 mM gave greater than an order of magnitude improvement in rate. Increasing the pH from 8 to 9, further tripled the rate. Adding DMSO gave a small increase in rate but shifted the optimum pH, thus a buffer containing 500 mM NaCl and 5% DMSO at pH 8 gave a reaction rate over 50 times greater (FIG. 1C). Under these conditions, about 7% linearized VGAGIGFP (SEQ ID NO: 70) byproduct was observed which can be separated from cyclo[VGAGIGFP] (SEQ ID NO: 70) by HPLC.

Site-directed mutants K594D and K598D as well as two deletion mutants 578-608 (the helix-loop-helix insertion motif, PatGmacΔ1) and 578-614 (the helix-loop-helix insertion and the N-terminal extension of α4, PatGmacΔ2) consumed substrate at approximately the rate of native protein (FIGS. 5 to 8 and FIGS. 10A-10C). For K594D approximately one third of the product was macrocyclized with two thirds being the linear peptide. K598D and both deletions gave only linear VGAGIGFP (SEQ ID NO: 70) (FIGS. 5 to 8 and FIGS. 10A-10C). The triple mutant R589D/K594D/K598D was substantially slower and only produced linear substrate. All mutants purified normally and were folded according to CD spectroscopy.

Figure 2:
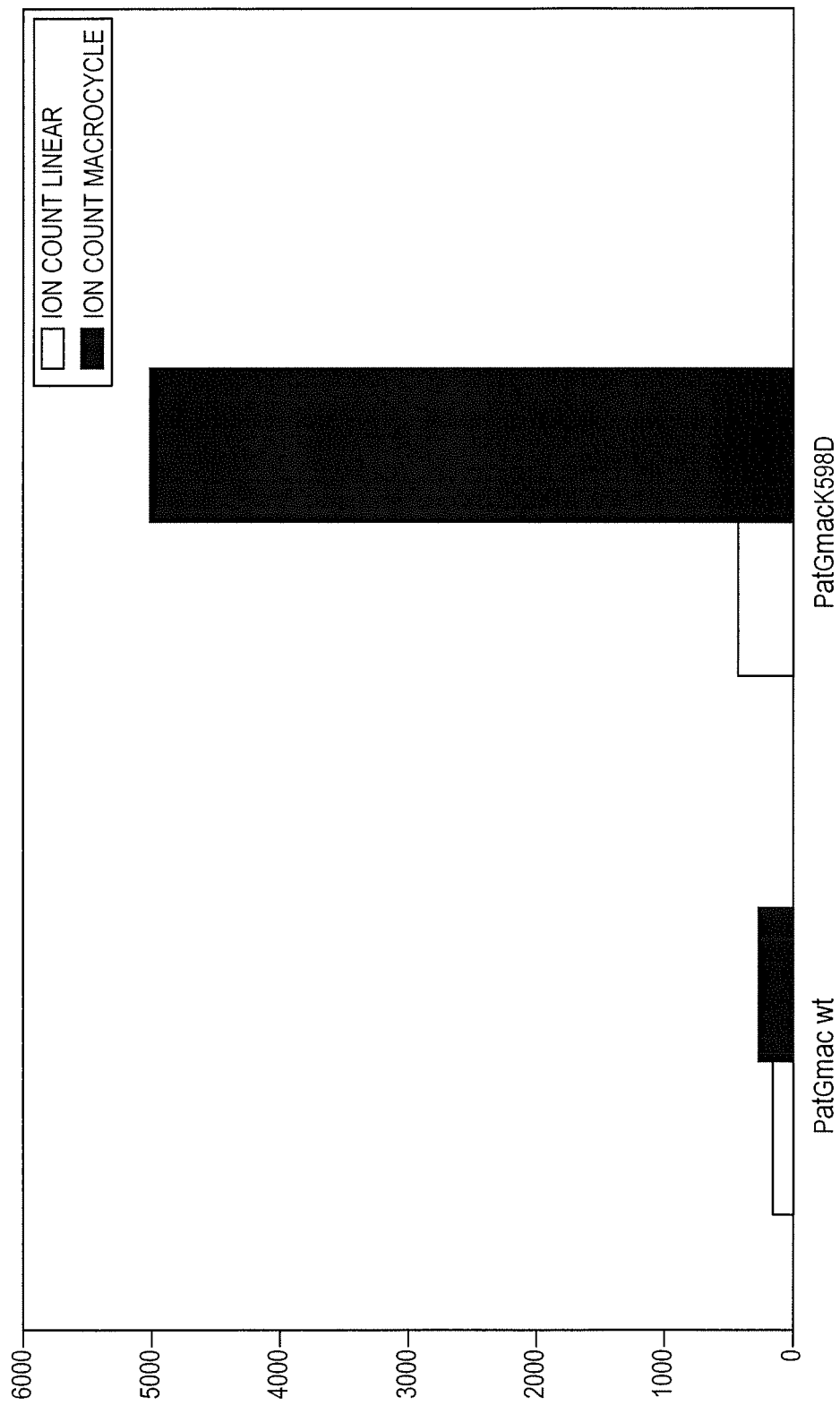
FIG. 2 shows ion counts of VGAGIGFPAYRG (SEQ ID NO: 69) processed by PatGmac wild-type and PatGmac K598D for linear and macrocyclized products as determined by LC-MS.
Figure 3:
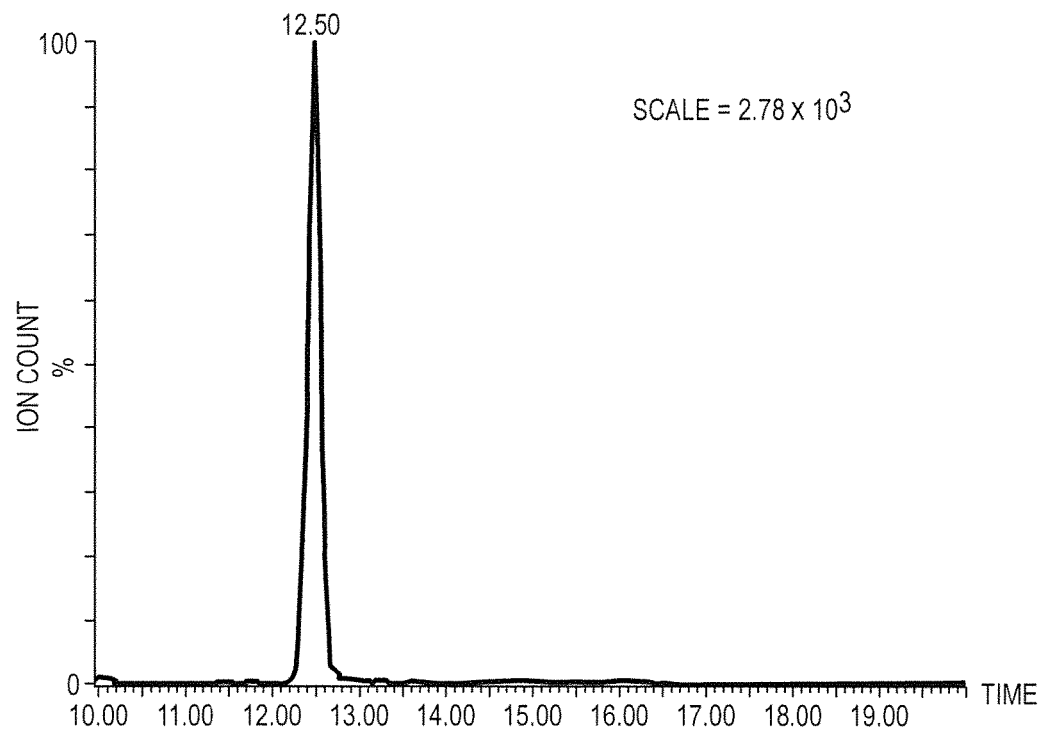
FIG. 3 shows LC-MS of the macrocyclization of the peptide substrate VGAGIGFPAYRG (SEQ ID NO: 69).
Figure 3:
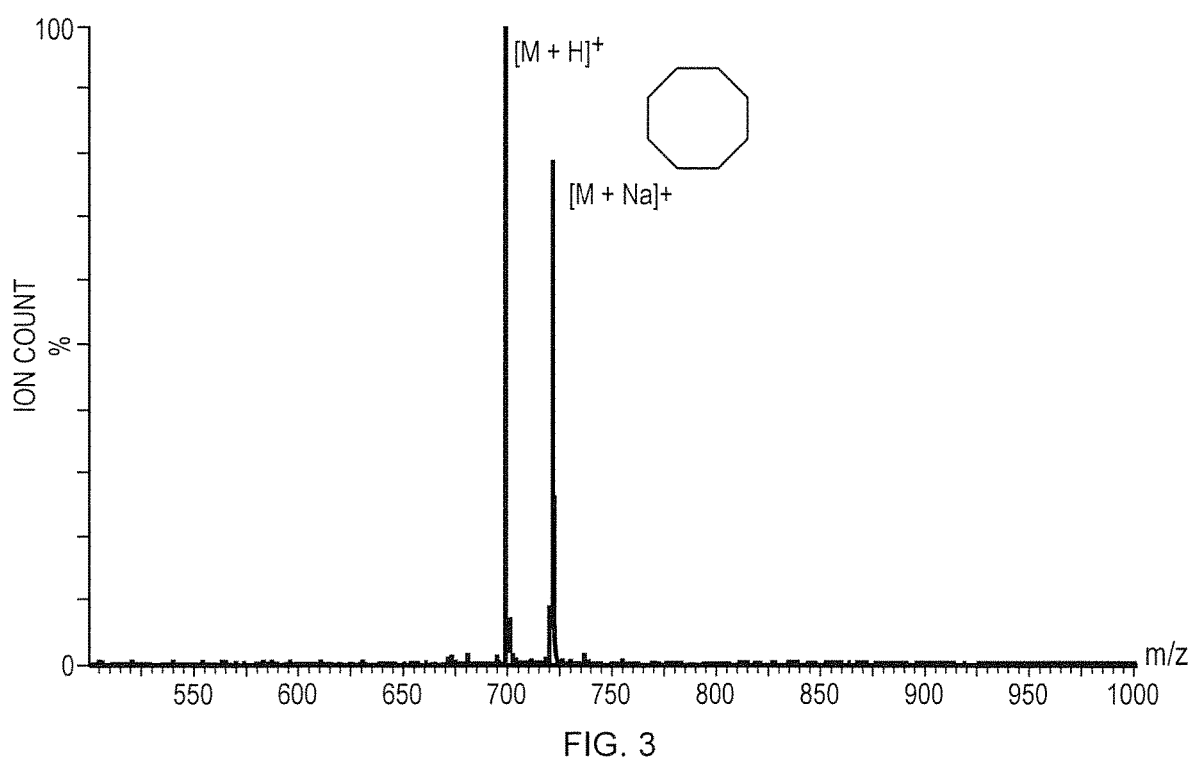

The substrate VGAGIGFPAYRG (SEQ ID NO: 69) has a modified recognition sequence (Asp to Arg); as expected PatGmac wild-type (and K594D and R589D/K594D/K598D) reacted extremely slowly with the substrate giving equal amounts of macrocyclized and linear products. PatGmac K598D produced cyclo[VGAGIGFP] with only 8% linear product, at a rate over an order of magnitude faster than wild-type PatGmac with VGAGIGFPAYDG (SEQ ID NO: 68) (FIGS. 2 and 3). The precise nature of the N terminus of the substrate influenced the rate, VGAGIGFPAYRG (SEQ ID NO: 69) was processed an order of magnitude faster than GVAGIGFPAYRG (SEQ ID NO: 84).

Site-directed mutants S783A and H618A (both catalytic triad) gave no detectable reaction. Mass spectrometry clearly identified an acyl-enzyme intermediate (VGAGIGFP-PatGmac) during turnover (FIG. 8).

To further explore macrocyclization, PatE pre-pro-peptide (PatE2) was engineered consisting of the 37-residue N-terminal leader sequence and N- and C-terminal cleavage recognition sites flanking a single cassette (ITACITFC) (SEQ ID NO: 21) corresponding to the natural product Patellamide D. In addition, a C-terminal $His_6$-tag was added to aid in the purification process (FIGS. 11A and 11B).

Precursor peptide PatE2, PatD and TruD (heterocyclases), PatApr (subtilisin-like protease domain) and PatGmac (subtilisin-like protease/macrocyclase domain) were cloned and expressed in *E. coli* and purified for use in biochemistry reactions (see materials & methods, above).

Example 5: Purification and Refolding of PatE2

PatE2 was cloned into the pBMS vector and expressed in *E. coli* BL21 (DE3) grown in auto-induction medium for 24 hours at 30° C., driving the protein to inclusion bodies. Cells were harvested by centrifugation at 4,000×g for 15 min at 20° C., re-suspended in urea lysis buffer (8 M urea, 500 mM NaCl, 20 mM Tris pH 8.0, 20 mM Imdiazole and 3 mM β-mercaptoethanol (βmE)) and lysed by sonication at 15 microns (SoniPrep 150, MSE). The lysate was cleared by centrifugation at 40,000×g, 20° C. followed by passage through a 0.45 μm filter. The cleared lysate was applied to a His-Select column (GE Healthcare) equilibrated with lysis buffer and protein eluted with 250 mM imidazole. The protein was then supplemented with 10 mM Dithiothreitol (DTT) to induce refolding and subjected to size-exclusion chromatography (Superdex 75, GE Healthcare) in 150 mM NaCl, 10 mM HEPES pH 7.4, 1 mM TCEP. The protein eluted as a single monomer peak with final yields of between 250 to 300 mg/L culture.

Example 6: In Vitro Heterocyclization of PatE2

In order to assess heterocyclization of our single cassette PatE, we carried out several in vitro reactions. Incubation of 100 μM PatE2 with 5 μM PatD in 150 mM NaCl, 10 mM HEPES pH 7.4, 1 mM TCEP, 5 mM ATP, 5 mM $MgCl_2$ at 37° C. for 30 minutes results in a loss of 72 amu corresponding to the expected four water losses, indicating that both threonine and both cysteine residues within the cassette were heterocyclized (FIG. 12).

Alternatively, incubation of 100 μM PatE2 with 5 μM TruD under the same conditions resulted in the expected loss of 36 amu corresponding to two water losses and confirming that only the cysteine residues were heterocyclized (FIGS. 13A and 13B).

Of all the enzymes used the two heterocyclases are by far the most difficult to express and purify (40 mg pure protein/L culture). We therefore wanted to investigate if they can be used in smaller amounts and recycled. When the heterocyclization reaction is incubated at 37° C. overnight the amount of enzyme can be reduced from 1:20 to 1:200 (Enzyme:Substrate) but the reaction time is significantly longer.

Passing the finished reaction over a Superdex S200 gel filtration column (GE Healthcare) gives three peaks: Enzyme, substrate and ATP/ADP (FIG. 14). When the enzyme peak is pooled, concentrated and used for another reaction it is still fully functional, clearly showing that enzyme recycling is possible without the downside of longer reaction times.

Example 7: N-Terminal Cleavage

N-terminal cleavage of the cassette is mediated by the subtilisin-like protease domain of PatA. The protease domain acts on the recognition site 'GLEAS'(SEQ ID NO: 41), cleaving between the S and the first residue of the cassette. We have found that turnover of this reaction in vitro is a slow process. In fact, incubation of 100 μM PatE2 (with or without prior heterocyclase treatment) with 20 μM PatApr at 37° C. for 200 hours is required for complete cleavage. The cassette portion is purified from PatApr and cleaved leader sequence by injecting the reaction on to a Superdex S30 column (GE Healthcare), pre-equilibrated in 150 mM NaCl, 20 mM Bicine pH 8.1. PatApr is highly expressed in *E. coli* with yields of >250 mg purified protein per liter of culture.

Due to the slow nature of PatApr, we re-engineered the PatE2 pre-pro-peptide to contain a lysine residue (PatE2K) between the PatA recognition sequence 'GLEAS'(SEQ ID NO: 41) and the cassette residues to allow for trypsin cleavage (FIGS. 11A and 11B) (e.g. $X_n$-GLEASK(SEQ ID NO: 59) [cassette]-$X_m$) To test if this addition affected heterocyclase activity, we incubated 100 μM PatE2K separately with 0.5 μM of both PatD and TruD overnight at 37° C. Expected water losses of four and two respectively were found by MS. The heterocyclized peptides were purified as previously described and cleaved with 1:1000 trypsin at 37° C. for 2 hours. Complete cleavage was confirmed by MS (FIG. 15) and the resulting fragments purified as above and subjected to macrocyclisation with PatGmac. Macrocyclisation of the peptide substrate was confirmed by MS.

The PatE2 pre-pro-peptide also re-engineered to contain a TEV protease signal (ENLYFQ) (SEQ ID NO: 58)) between the PatA recognition sequence 'GLEAS' and the cassette residues to allow for TEV cleavage (e.g. $X_n$-GLEASENLYFQ (SEQ ID NO: 60) [cassette]-$X_m$) To test if this addition affected heterocyclase activity, we incubated 100 μM PatE2TEV separately with 0.5 μM of PatD overnight at 37° C. Expected water losses of four and two respectively were found by MS. The heterocyclized peptides were purified as previously described and cleaved with 1:1000 TEV at 37° C. for 2 hours. Complete cleavage was confirmed by MS and the resulting fragments purified as above and subjected to macrocyclisation with PatGmac. Macrocyclisation of the peptide substrate was confirmed by MS.

Example 8: C-Terminal Cleavage and Macrocyclization

The final stage in patellamide production is C-terminal cleavage and macrocyclization. This step is catalyzed by the PatGmac domain. In order to macrocyclize our single cassette we incubated 100 μM heterocyclized (with either PatD or TruD) and N-terminally cleaved PatE2/PatE2K with 20 μM PatGmac for 24 hours at 37° C. in 20 mM Bicine pH 8.1, 500 mM NaCl, 5% DMSO to complete the reaction. Completeness of the reaction was confirmed by LCT-ESI MS (FIG. 16). Ion count analysis shows that the sample was 100% macrocyclized with no linear product or non-cleaved substrate present. PatGmac is also highly expressed in *E. coli* with between 200 and 250 mg purified protein obtained per liter of culture. The final macrocycles were purified by HPLC on a C18 peptide column. PatD and TruD heterocyclised macrocycles were subjected to HRMS and their structures confirmed by fragmentation (see FIGS. 19 to 21; Table 3). NMR analysis was carried out on TruD and PatD heterocyclised macrocycles, as shown in FIGS. 20 and 21) (Tables 7 and 8).

Example 9: Purification of Patellamides

PatE substrates with the core sequence cassettes ITVCITVC (SEQ ID NO: 30) (TruD), ITACITFC (SEQ ID NO: 21) (TruD, PatD), ITACITYC (SEQ ID NO: 25) (TruD, PatD), IMACIMAC (SEQ ID NO: 28) (TruD), IDACIDFC (SEQ ID NO: 29) (TruD), VTVCVTVC (SEQ ID NO: 33)

(TruD, PatD), ITA(SeCys)ITF(SeCys) (SEQ ID NO: 27) (TruD), ACIMAC (SEQ ID NO: 35) (TruD), IACIMAC (SEQ ID NO: 36) (TruD), IITACIMAC (SEQ ID NO: 37) (TruD), ICACITFC (SEQ ID NO: 23) (TruD), IAACITFC (SEQ ID NO: 24) (TruD), ITACITAC (SEQ ID NO: 26) (TruD), ATACITFC (SEQ ID NO: 38) (TruD), ITAAITFC (SEQ ID NO: 31) (TruD) and ITACISFC (SEQ ID NO: 22) (TruD) were treated with either PatD or TruD heterocyclase as indicated, then subjected to proteolysis with trypsin and macrocyclisation with PatGmac, as described above. The cyclic products cyclo(ITV(Thn)ITV(Thn)) (SEQ ID NO: 79), cyclo(ITA(Thn)ITF(Thn)) (SEQ ID NO: 77), cyclo(I(MeOxn)A(Thn)I(MeOxn)F(Thn)) (SEQ ID NO: 73), cyclo (ITA(Thn)ITY(Thn)) (SEQ ID NO: 87), cyclo(I(MeOxn)A(Thn)I(MeOxn)Y(Thn)) (SEQ ID NO: 88), cyclo-(IMA(Thn)IMA(Thn)) (SEQ ID NO: 89), cyclo-(IDA(Thn)IDF(Thn)) (SEQ ID NO: 90), cyclo-(VTV(Thn)VTV(Thn) (SEQ ID NO: 91), cyclo-(V(MeOxn)V(Thn)V(MeOxn)V(Thn)) (SEQ ID NO: 92), cyclo-(ITA(Sen)ITF(Sen)) (SEQ ID NO: 93), cyclo-(A(Thn)IMA(Thn)) (SEQ ID NO: 94), cyclo-(IA(Thn)IMA(Thn)) (SEQ ID NO: 95), cyclo-(IITA(Thn)IMA(Thn)) (SEQ ID NO: 96), cyclo-(I(Thn)A(Thn)ITF(Thn)) (SEQ ID NO: 97), cyclo-(IAA(Thn)ITF(Thn)) (SEQ ID NO: 98), cyclo-(ITA(Thn)ITA(Thn)) (SEQ ID NO: 99), cyclo-(ATA(Thn)ITF(Thn)) (SEQ ID NO: 100), cyclo-(ITAAITF(Thn)) (SEQ ID NO: 101) and cyclo-(ITA(Thn)ISF(Thn)) (SEQ ID NO: 102) were then purified and analysed by NMR and MS.

The production of heterocycle-containing macrocyclic structures was confirmed for all of these peptide substrates.

NMR data for cyclo-(I(MeOxn)V(Thn)I(MeOxn)V(Thn)) (SEQ ID NO: 76) (Cmpd 32) produced from substrate peptide ITVCITVC(SEQ ID NO: 30) and cyclo-(ITA(Thn)ITF(Thn)) (SEQ ID NO: 77) (Cmpd 33) produced from substrate peptide ITACITFC (SEQ ID NO: 21) were tabulated (Tables 7 and 8). Furthermore, the NMR spectrum from in vitro cyclo-(I(MeOxn)V(Thn)I(MeOxn)V(Thn)) (SEQ ID NO: 76) was found to correspond to the NMR spectrum of the natural tetrahydroascidiacyclamide produced by *Lissoclinum patella*

The ability to oxidise heterocycles following macrocyclisation was determined by assessing the conversion of thioazolines to thiazoles. Reduced cyclo-(I(MeOxn)V(Thn)I(MeOxn)V(Thn)) (SEQ ID NO: 76) produced from substrate peptide ITVCITVC (SEQ ID NO: 30) was subjected to oxidation using MnO$_2$ in dichloromethane for three days at 28° C. The resulting mixture was subjected to silica gel and celite column chromatography followed by HPLC chromatography to yield the oxidized product (FIG. 25). Far UV CD spectra of cyclo-(I(MeOxn)V(Thn)I(MeOxn)V(Thn)) (SEQ ID NO: 76) (reduced form), cyclo-I(MeOxz)V(Thz)I(MeOxz)V(Thz)) (SEQ ID NO: 80) (oxidised form) and ascidiacyclamide isolated from *Lissoclinum patella* were recorded at room temperature in a 0.02 cm pathlength quartz cuvette using notional concentrations of ~1 mg/mL. The CD spectrum of the oxidised cyclo-I(MeOxz)V(Thz)I(MeOxz)V(Thz)) (SEQ ID NO: 80) was found to correspond to the CD spectrum of ascidiacyclamide (FIG. 26).

Example 10: Use of SUMO (Small Ubiquitin-Like Modifier) Tags

A peptide substrate was engineered with a SUMO-tag (Marblestone et al Protein Sci. 2006 January; 15(1): 182-189) and a cassette sequence that previously showed no soluble expression. SUMO tags are small solubility tags (linked to a His$_6$tag) of total size 13.6 kDa (MBP=42 kDa, GST=30 kDa) which can be used to increase the level of soluble expression of a target protein. SDS-PAGE analysis showed that the peptide substrate was expressed in soluble form and the SUMO tag could be removed from the substrate with TEV protease.

Example 11: Use of a Reduced Leader Sequence

It has previously been reported that the leader sequence of PatE is essential for heterocyclisation. We probed the interaction of $^{15}$N-PatE with TruD (titrating until two-fold molar excess of TruD to PatE).

Residues 1-15 undergo no change and thus appear uninvolved in binding to TruD. The remainder of the residue signals are broadened to such an extent that they become invisible, indicating that binding occurs at or after residue 16. The most highly conserved sequence in the leader region of PatE spans residues 26-34. A synthetic peptide with the first 25 residues of PatE (Δ25PatE) deleted is processed as efficiently by TruD as native PatE. Three additional peptides were tested Δ37PatE (has only the five residue protease signature prior to the core peptide), Δ42PatE (first residue is core peptide) and the eight-residue core peptide itself. No reaction is seen with the core peptide alone, and surprisingly both Δ37PatE and Δ42PatE peptides are processed at a rate within an order of magnitude of the native, but only one residue of the core peptide (the terminal cysteine) reacts.

Targeting individual residues within the conserved leader region revealed S30 was unimportant (S30F has wild type activity), but L29 and E31 were important. L29R and E31R both processed more slowly and gave mixtures of one and two heterocycles. Mutations G38I, L39N and A41I (within GLEAS protease signature) had no effect on heterocyclisation, while S42Q was processed at a much slower rate and intriguingly gave a mixture of 0 and 2 heterocycles while S42C was processed like wild-type. The mutation A52D was processed much slower, at the rate of S42Q, and also gave a mixture of 0 and 2 heterocycles. In contrast mutations Y53A and D54R, also within the macrocyclization sequence "AYDG" immediately C-terminal, were both processed.

Two PatE mutants with core peptide sequences ITACITFP (SEQ ID NO: 103) (C51P) and ITACITFA (SEQ ID NO: 104) (C51A) were analyzed. The internal cysteine in C51P heterocyclised (judged by mass spectrometry) within 60 min at 37° C. (similar to native). The C51A mutant PatE without a five-membered ring at the C-terminus on the other hand reacted much more slowly, requiring 16 h at 37° C. for ~50% product formation.

Example 12: Dimer Formation from Cys Containing Cyclic Peptide

The MALDI mass spectrum of the novel cyclo[VGICAGFP] (SEQ ID NO: 81) macrocyclic peptide (6; FIG. 27), exhibited a peak at 1509 Da, which provided indication that it was in a dimeric form, (21; FIG. 27) where two cyclic peptides were linked via a disulfide bond between their cysteine residues (FIG. 27). The VGICAGFP (SEQ ID NO: 81) cyclic monomer has a mass of 744 Da, and dimerization through the thiols would result in a mass of 2×744 (cyclic monomer)−2 (two hydrogens lost on disulfide bond formation)=1486 Da, and the sodiated ion would produce the peak at 1486+23=1509 Da.

Modification of the peptides at the cysteine residues could not be carried out without reducing the disulfide bond first. Reduction was attempted using several different reducing agents, namely TCEP, DTT, mercaptoethanol and TCEP immobilized on resin. Reduction with TCEP and DTT were shown to be the most effective, achieving complete reduction of the dimer at t=1 hr, where the peak at 1509 Da completely disappeared and peaks at 745 Da and 767 Da (corresponding to the protonated and sodiated forms of the monomeric cyclic peptide, respectively) appeared. TCEP immobilized on resin and β-mercaptoethanol resulted in partial reduction.

Example 13: Formation of Cyclotides Using the Engineered PatGmac

Cyclotides e.g. katala B1 are a family of plant proteins (28-40 amino acids) that have a unique topology, which combines a circular peptide backbone and a tightly knotted disulfide network that forms a CCK (cyclic cysteine knot) motif and makes the more than 80 known cyclotides exceptionally stable. The cyclotides are resistant to thermal unfolding, chemical denaturants and proteolytic degradation. There is a wide interest in making these compounds for wide range of applications.

We tested the ability of the engineered PatGmac to macrocyclise the linear peptide sequence of katala B1, monitored the reaction using MALDI and compared the MS of the synthetic product with that of the purified native Katala B1. The reaction substrates were the oxidised and reduced form of the linear peptide sequence and contain at their C-term the recognition signal of PatG (AYDG) (SEQ ID NO: 20). PatGmac was found to cyclise both the reduced and oxidised precursors. The reduced precursor gave no traceable starting material after reaction with the enzyme and the oxidised version being less efficient.

Example 14: Formation of Imidazolines Using PatD or TruD

A minimal peptide ITASITFXAYDG (SEQ ID NO: 82) (where X is g the unnatural amino acid 2,3-diaminopropanoic acid) was incubated with TruD or PatD as described above The reaction was analysed by MALDI MS and shows a loss of 18 Da consistent with heterocycle formation (formation of imidazoline) for both reactions, although the enzyme TruD was more efficient in this reaction (FIG. 28).

Compounds

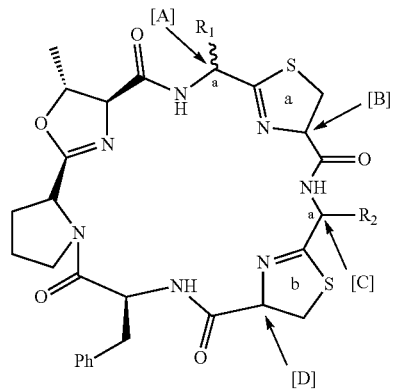

|  | $R_1$ | $R_2$ | $R_3$ | $R_4$ | $R_5$ |
|---|---|---|---|---|---|
| Patellamide A (1) | CHMeEt | $CHMe_2$ | CHMeEt | H | $CHMe_2$ |
| Patellamide B (2) | $CH_2CHMe_2$ | Me | CHMeEt | Me | $CH_2Ph$ |
| Patellamide C (3) | $CHMe_2$ | Me | CHMeEt | Me | $CH_2Ph$ |
| Patellamide D (4) | CHMeEt | Me | CHMeEt | Me | $CH_2Ph$ |
| Patellamide E (5) | $CHMe_2$ | $CHMe_2$ | CHMeEt | Me | $CH_2Ph$ |
| Patellamide F (6) | $CHMe_2$ | $CHMe_2$ | $CHMe_2$ | Me | $CH_2Ph$ |
| Patellamide G (7) | CHMeEt | Me | $CH_2CHMe_2$ | Me | $CH_2Ph$ |
| Ascidiacyclamide (8) | CHMeEt | $CHMe_2$ | CHMeEt | Me | $CHMe_2$ |

|  | $R_1$ | $R_2$ |  | Stereochemistry |
|---|---|---|---|---|
| Lissoclinamide 1 (9) | $CHMe_2$ | CHMeEt | a = b = thiazole | [A] = S [C] = R |
| Lissoclinamide 2 (10) | CHMeEt | Me | a = thiazoline, b = thiazole | [A] = R [C] = R |
| Lissoclinamide 3 (11) | CHMeEt | Me | a = thiazoline, b = thiazole | [A] = R [B] = R [C] = S |

-continued

| | | | |
|---|---|---|---|
| Lissoclinamide 4 (12) | CHMe$_2$ | CH$_2$Ph | a = thiazoline, b = thiazole | [A] = S [B] = R [C] = R |
| Lissoclinamide 5 (13) | CHMe$_2$ | CH$_2$Ph | a = b = thiazole | [A] = S [C] = R |
| Lissoclinamide 6 (14) | CHMe$_2$ | CH$_2$Ph | a = thiazoline, b = thiazole | [A] = R [B] = R [C] = R |
| Lissoclinamide 7 (15) | CHMe$_2$ | CH$_2$Ph | a = b = thiazoline | |
| Lissoclinamide 8 (16) | CHMe$_2$ | CH$_2$Ph | a = thiazoline, b = thiazole | |
| Lissoclinamide 9 (17) | CHMeEt | CHMe$_2$ | a = thiazoline, b = thiazole | [A] = S [B] = R [C] = R |
| Lissoclinamide 10 (18) | CHMeEt | CHMeEt | a = thiazoline, b = thiazoline | [A] = S [B] = R [C] = S [D] = R |
| Ulicyclamide (19) | CHMeEt | Me | a = b = thiazole | [A] = S [C] = R |

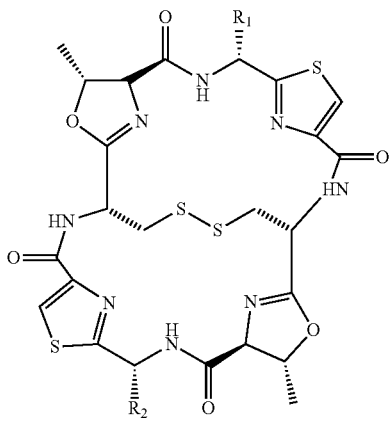

| | R$_1$ | R$_2$ |
|---|---|---|
| Ulithiacyclamide A (20) | CH$_2$CHMe$_2$ | CH$_2$CHMe$_2$ |
| Ulithiacyclamide B (21) | CH$_2$Ph | CH$_2$CHMe$_2$ |

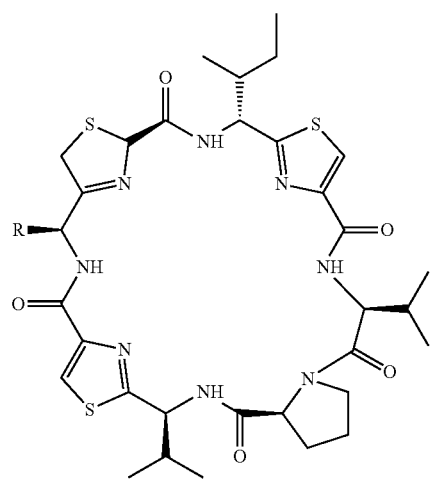

| | R |
|---|---|
| Tawicyclamide A (22) | CH$_2$CHMe$_2$ |
| Tawicyclamide B (23) | CH$_2$Ph |

-continued
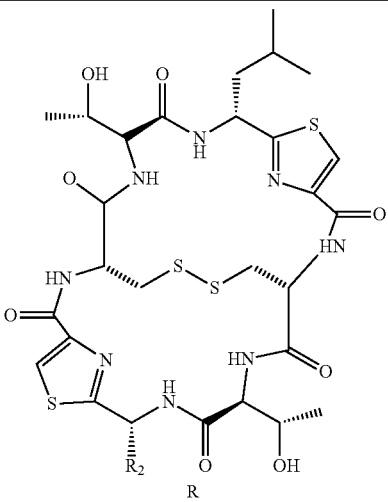
| Ulithiacyclamide E (24) | CH₂Ph |
| Preuiithiacyclamide (25) | CH₂CHMe₂ |
(26)
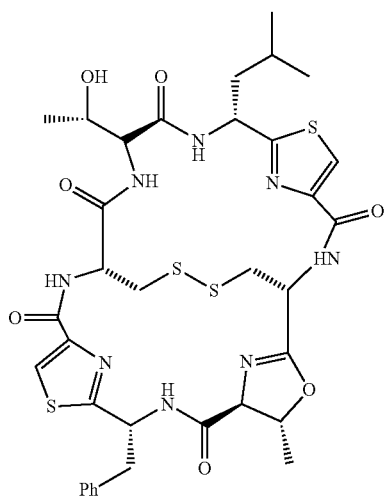
Ulithiacyclamide F
(27)
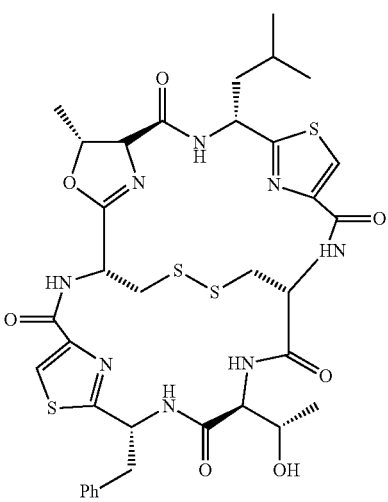
Ulithiacyclamide G -continued
(28)
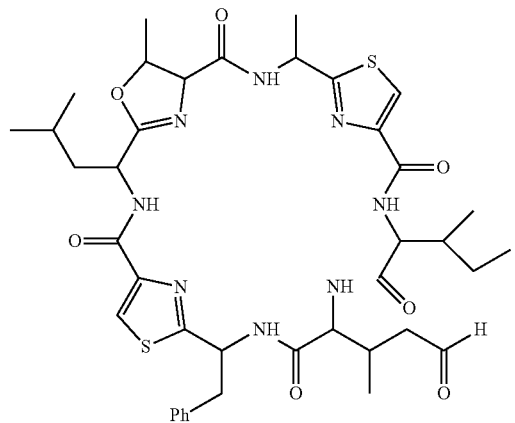 [SMILES: CCC(C)C(C=O)NC(=O)c1csc(C(C)NC(=O)C2N=C(C(CC(C)C)NC(=O)c3csc(C(Cc4ccccc4)NC(=O)C(N)C(C)CC=O)n3)OC2C)n1]
Ulithiacyclamide F
(29)
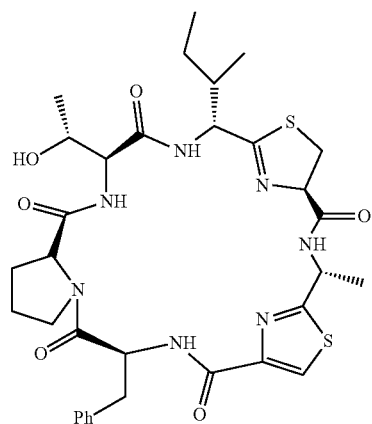
Prelissoclinamide-2
(30)
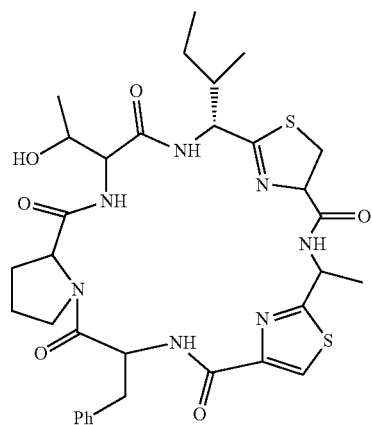 [SMILES: CCC(C)[C@H]1NC(=O)C(C(C)O)NC(=O)C2CCCN2C(=O)C(Cc2ccccc2)NC(=O)c2csc(n2)C(C)NC(=O)C2CSC1=N2]
Preulicyclamide

(31)
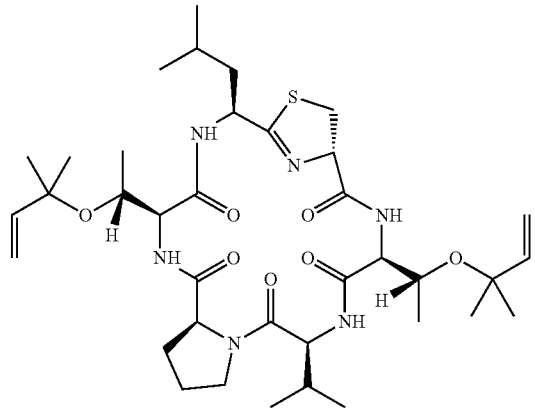 [SMILES: C=CC(C)(C)O[C@H](C)[C@@H]1NC(=O)[C@H]2CSC(=N2)[C@H](CC(C)C)NC(=O)[C@H]([C@@H](C)OC(C)(C)C=C)NC(=O)[C@@H]2CCCN2C(=O)[C@H](C(C)C)NC1=O]
Patellin 2
(32)
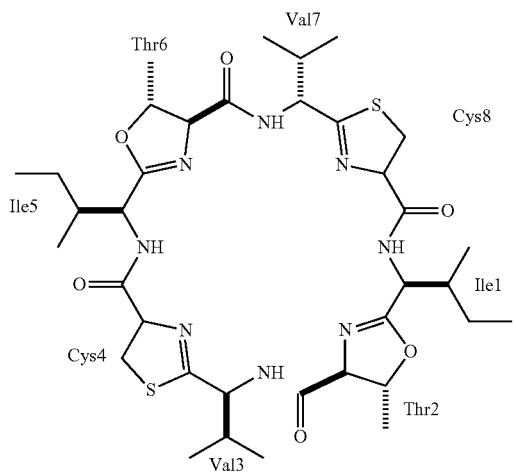
ITVCITVC
(33)
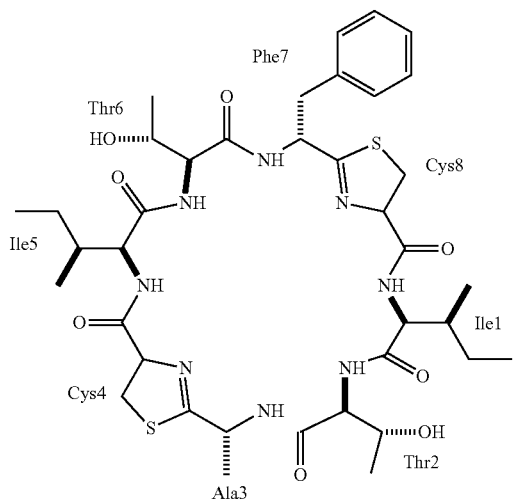
ITACITFC

TABLE 1

|  | PatGmac | PatGmac + Peptide |
|---|---|---|
| Data collection | | |
| Space group | C2 | C2 |
| Cell dimensions | | |
| a, b, c (Å) | 132.08, 67.58, 97.34 | 135.63, 67.32, 137.87 |
| α, β, γ (°) | 90, 115.01, 90 | 90, 116.76, 90 |
| Resolution (Å) | 2.19 (2.24-2.19) | 2.63 (2.77-2.63) |
| $R_{sym}$ or $R_{merge}$ | 6.1 (49.8) | 10.7 (52.2) |
| I I | 13.7 (2.9) | 10.1 (2.3) |
| Completeness (%) | 99.5 (98.8) | 99.3 (96.4) |
| Redundancy | 3.6 (3.5) | 3.7 (3.1) |
| Refinement | | |
| Resolution (Å) | 33.79-2.19 | 21.42-2.63 |
| No. reflections | 38,196 | 31,502 |
| $R_{work}/R_{free}$ | 0.203/0.224 | 0.191/0.218 |
| No. atoms | 4,877 | 5,108 |
| Protein | 4,653 | 4,897 |
| Ligand/ion | N/A | 69 |
| Water | 224 | 142 |
| B-factors | 50.11 | 60.56 |
| Protein | 50.04 | 60.70 |
| Ligand/ion | N/A | 77.98 |
| Water | 51.5 | 47.19 |
| R.m.s. deviations | | |
| Bond lengths (Å) | 0.009 | 0.009 |
| Bond angles (°) | 1.249 | 1.253 |

*1 crystal user per structure
*Values in parentheses are for highest-resolution shell.

TABLE 2

|  | Unprocessed ion count (%) (M + H = 1123) | Linear ion count (%) (M + H = 717) | Cyclic ion count (%) (M + H = 699) |
|---|---|---|---|
| PatGmac | 0 | 0 | 100 |
| PatGmacΔ1 | 8 | 92 | 0 |
| PatGmacΔ2 | <1 | >99 | 0 |
| PatGmac K598D | 0 | 100 | 0 |
| PatGmac K594D | 0 | 71 | 29 |
| PatGmac R589D | 94 | 6 | 0 |
| K594D K598D | | | |

TABLE 3

| Mass/Error (ppm) | Molecular Formula | Loss |
|---|---|---|
| 817.3735 (1.11) | $C_{38}H_{57}N_8O_8S_2$ | $[M + H]^+$ |
| 789.3752 (4.34) | $C_{37}H_{57}O_7N_8S_2$ | CO |
| 781.3490 (−4.35) | $C_{38}H_{53}O_6N_8S_2$ | $2H_2O$ |
| 771.3650 (−3.96) | $C_{37}H_{55}O_6N_8S_2$ | $CO + H_2O$ |
| 754.3388 (−3.57) | $C_{37}H_{52}O_6N_7S_2$ | $2H_2O + CNO$ |
| 686.2761 (4.13) | $C_{32}H_{44}O_6N_7S_2$ | Thr-Ala |
| 447.2040 (−4.47) | $C_{22}H_{31}N_4O_4S$ | Cys-Ile-Thr-Ala |
| 817.3735 (1.11) | $C_{38}H_{57}N_8O_8S_2$ | $[M + H]^+$ |

TABLE 4

GI: 62910837 AAY21150.1 subtilisin-like protein [*Prochloron didemni*]
>gi|167859094|gb|ACA04487.1| TruA [uncultured *Prochloron* sp. 06037A]
>gi|119492363|ref|ZP_01623699.1| hypothetical protein L8106_29035 [*Lyngbya* sp. PCC 8106]
>gi|389832535|emb|CCI23777.1| conserved hypothetical protein [*Microcystis aeruginosa* PCC 9809]
>gi|389678159|emb|CCH92969.1| conserved hypothetical protein [*Microcystis aeruginosa* PCC 9432]
>gi|159027542|emb|CAO86912.1| unnamed protein product [*Microcystis aeruginosa* PCC 7806]
>gi|158934368|emb|CAO82081.1| subtilisin-like protein [*Microcystis aeruginosa* NIES-298]
>gi|389788450|emb|CCI15917.1| Subtilisin-like protein [*Microcystis aeruginosa* PCC 9806]
>gi|167859086|gb|ACA04480.1| TenA [*Nostoc spongiaeforme* var. tenue str. Carmeli]
>gi|291571097|dbj|BAI93369.1| putative peptidase [*Arthrospira platensis* NIES-39]
>gi|376002137|ref|ZP_09779984.1| putative Subtilisin-like serine protease, PatA-like [*Arthrospira* sp. PCC 8005]
>gi|280987221|gb|ACK37888.2| anacyclamide synthesis protein AcyA [*Anabaena* sp. 90]
>gi|332002613|gb|AED99426.1| N-terminal cyanobactin protease [*Planktothrix agardhii* NIES-596]
>gi|300866524|ref|ZP_07111214.1| peptidase S8/S53 subtilisin kexin sedolisin [*Oscillatoria* sp. PCC 6506]
>gi|113475994|ref|YP_722055.1| peptidase S8/S53 subtilisin kexin sedolisin [*Trichodesmium erythraeum* IMS101]
>gi|389882390|emb|CCI37139.1| Peptidase S8 and S53, subtilisin, kexin,
>gi|389826374|emb|CCI23117.1| Peptidase S8 and S53, subtilisin, kexin, sedolisin [*Microcystis aeruginosa* PCC 9808]
>gi|389731215|emb|CCI04699.1| Peptidase S8 and S53, subtilisin, kexin, sedolisin [*Microcystis aeruginosa* PCC 9443]
>gi|389802077|emb|CCI18837.1| Peptidase S8 and S53, subtilisin, kexin, sedolisin [*Microcystis aeruginosa* PCC 9807]
>gi|119512478|ref|ZP_01631559.1| hypothetical protein N9414_11234 [*Nodularia spumigena* CCY9414]
>gi|307591572|ref|YP_003900371.1| peptidase S8 and S53 subtilisin kexin sedolisin [*Cyanothece* sp. PCC 7822]
>gi|220905947|ref|YP_002481258.1| peptidase S8/S53 subtilisin kexin sedolisin [*Cyanothece* sp. PCC 7425]
>gi|217316976|gb|ACK37899.1| subtilisin-like protease [*Microcystis* sp. 130]
>gi|217316978|gb|ACK37900.1| subtilisin-like protease [*Oscillatoria* sp. 327/2]
>gi|217316980|gb|ACK37901.1| subtilisin-like protease [*Tolypothrix* sp. TOL328]

TABLE 4-continued

>gi|113475997|ref|YP_722058.1| peptidase S8/S53 subtilisin kexin sedolisin [*Trichodesmium erythraeum* IMS101]
>gi|217316950|gb|ACK37886.1| subtilisin-like protease [*Aphanizomenon flos-aquae* TR183]
>gi|217316958|gb|ACK37890.1| subtilisin-like protease [*Nodularia spumigena* AV1]
>gi|217316952|gb|ACK37887.1| subtilisin-like protease [*Anabaena lemmermannii* var. minor NIVA-CYA 83/1]
>gi|217316956|gb|ACK37889.1| subtilisin-like protease [*Anabaena planctonica* 1tu33s10]
>gi|217316968|gb|ACK37895.1| subtilisin-like protease [*Planktothrix* sp. 28]
>gi|217316974|gb|ACK37898.1| subtilisin-like protease [*Planktothrix agardhii* NIVA-CYA 126/8]
>gi|217316970|gb|ACK37896.1| subtilisin-like protease [*Planktothrix agardhii* 2]
>gi|217316972|gb|ACK37897.1| subtilisin-like protease [*Planktothrix agardhii* 49]
>gi|217316948|gb|ACK37885.1| subtilisin-like protease [*Anabaena lemmermannii* 202A2/41]
>gi|284053852|ref|ZP_06384062.1| peptidase S8 and S53 subtilisin kexin sedolisin [*Arthrospira platensis* str. Paraca]
>gi|217316964|gb|ACK37893.1| subtilisin-like protease [*Snowella litoralis* 0tu35s07]
>gi|217316984|gb|ACK37903.1| subtilisin-like protease [*Oscillatoria sancta* PCC 7515]
>gi|217316966|gb|ACK37894.1| subtilisin-like protease [*Snowella litoralis* 0tu37s04]
>gi|217316982|gb|ACK37902.1| subtilisin-like protease [*Lyngbya aestuarii* PCC 7419]

TABLE 5 gi|62910840|gb|AAY21153.1| adenylation/heterocyclization protein
>gi|167859097|gb|ACA04490.1| TruD [uncultured *Prochloron* sp. 06037A]
>gi|167859089|gb|ACA04483.1| TenD [*Nostoc spongiaeforme* var. tenue str. Carmeli]
>gi|389788447|emb|CCI15911.1| heterocyclization protein [*Microcystis aeruginosa* PCC 9806]
>gi|158934371|emb|CAO82084.1| heterocyclization protein [*Microcystis aeruginosa* NIES-298]
>gi|159027545|emb|CAO86915.1| unnamed protein product [*Microcystis aeruginosa* PCC 7806]
>gi|389832532|emb|CCI23771.1| heterocyclization protein [*Microcystis aeruginosa* PCC 9809]
>gi|119492367|ref|ZP_01623703.1| hypothetical protein L8106_29055 [*Lyngbya* sp. PCC 8106]
>gi|389678157|emb|CCH92967.1| conserved hypothetical protein [*Microcystis aeruginosa* PCC 9432]
>gi|284051362|ref|ZP_06381572.1| hypothetical protein AplaP_07802 [*Arthrospira platensis* str. Paraca]
>gi|291571091|dbj|BAI93363.1| hypothetical protein [*Arthrospira platensis* NIES-39]
>gi|376002141|ref|ZP_09779988.1| conserved hypothetical protein, PatD-like [*Arthrospira* sp. PCC 8005]
>gi|300866528|ref|ZP_07111218.1| conserved hypothetical protein [*Oscillatoria* sp. PCC 6506]
gi|113475987|ref|YP_722048.1| hypothetical protein [*Trichodesmium erythraeum* IMS101]
>gi|220905960|ref|YP_002481271.1| hypothetical protein [*Cyanothece* sp. PCC 7425]
>gi|307591570|ref|YP_003900369.1| hypothetical protein Cyan7822_6535 [*Cyanothece* sp. PCC 7822]
>gi|254415697|ref|ZP_05029455.1| YcaO-like family protein [*Microcoleus chthonoplastes* PCC 7420]
>gi|307592449|ref|YP_003900040.1| Cyan7822_6146 [*Cyanothece* sp. PCC 7822]
>gi|218442712|ref|YP_002381032.1| PCC7424_5737 [*Cyanothece* sp. PCC 7424]
>gi|307592454|ref|YP_003900045.1| Cyan7822_6152 [*Cyanothece* sp. PCC 7822]
>gi|389804481|emb|CCI16484.1| Genome sequencing data, contig C264 [*Microcystis aeruginosa* PCC 9807]
>gi|389714868|emb|CCI00585.11| Genome sequencing data, contig C264 [*Microcystis aeruginosa* PCC 9717]
>gi|307150541|ref|YP_003885925.1| hypothetical protein Cyan7822_0614 [*Cyanothece* sp. PCC 7822]
>gi|389883469 emb|CCI36141.1| Genome sequencing data, contig C264 [*Microcystis aeruginosa* PCC 9701]
>gi|374996241|ref|YP_004971740.1| bacteriocin biosynthesis cyclodehydratase domain protein [*Desulfosporosinus orientis* DSM 765]
>gi|389732059|emb|CCI03939.1| Genome sequencing data, contig C264 [*Microcystis aeruginosa* PCC 9443]
>gi|114567303|ref|YP_754457.1| hypothetical protein Swol_1788 [*Syntrophomonas wolfei* subsp. *wolfei* str. Goettingen]
>gi|300864741|ref|ZP_07109593.1| conserved hypothetical protein [*Oscillatoria* sp. PCC 6506]
>gi|159026417|emb|CAO87926.1| unnamed protein product [*Microcystis aeruginosa* PCC 7806]
>gi|126661106|ref|ZP_01732187.1| hypothetical protein CY0110_05027 [*Cyanothece* sp. CCY0110]
>gi|335387282|gb|AEH57221.1| cyclodehydratase/YcaO-domain protein [*Prochloron didemni* P1-Palau]
>gi|115375227|ref|ZP_01462493.1| adenylation/heterocyclization protein [*Stigmatella aurantiaca* DW4/3-1]
>gi|166366054|ref|YP_001658327.1| hypothetical protein MAE_33130 [*Microcystis aeruginosa* NIES-843]
>gi|389830836|emb|CCI26902.1| Genome sequencing data, contig C264 [*Microcystis aeruginosa* PCC 9809]
>gi|172039012|ref|YP_001805513.1| hypothetical protein cce_4099 [*Cyanothece* sp. ATCC 51142]
gi|357391463|ref|YP_004906304.1| adenylation/heterocyclization protein [*Kitasatospora setae* KM-6054]
>gi|330467969|ref|YP_004405712.1| [*Verrucosispora mans* AB-18-032]
>gi|78042201|dbj|BAE46919.1| goadsporin biosynthetic protein [*Streptomyces* sp. TP-A0584]
>gi|269126981|ref|YP_003300351.1| Tcur_2767 [*Thermomonospora curvata* DSM 43183]

TABLE 6

| Residue/Atom | | In vitro $\delta_C$/ppm | In vitro $\delta_{H/ppm}$ |
|---|---|---|---|
| Ile1[a] | | | |
| α | CH | 56.7 | 4.52 |
| β | CH | 38.4 | 1.76 |
| γ₁ | CH₃ | 15.3 | 0.88 |
| γ₂ | CH₂ | 25.0 | 1.48/1.12 |
| δ | CH₃ | 11.0 | 0.89 |
| C=O | C | n.o. | — |
| NH | — | — | 7.56 |
| Thr2[b] | | | |
| α | CH | 56.6 | 4.32 |
| β | CH | 65.1 | 4.44 |
| γ | CH₃ | 18.4 | 1.14 |
| C=O | C | 172.6 | — |
| NH | — | — | 7.07 |
| Ala3 | | | |
| α | CH | 48.4 | 4.69 |
| β | CH | 20.7 | 1.37 |
| C=N | C | 174.9 | — |
| NH | — | 8.48 | — |
| Cys4 | | | |
| α | CH | 77.6 | 5.05 |
| β | CH₂ | 36.6 | 3.70 |
| C=O | C | 170.3 | — |
| Ile5[a] | | | |
| α | CH | 56.8 | 4.53 |
| β | CH | 38.4 | 1.76 |
| γ₁ | CH₃ | 14.1 | 0.85 |
| γ₂ | CH₂ | 25.0 | 1.45/1.10 |
| δ | CH₃ | 11.0 | 0.83 |
| C=O | C | n.o. | — |
| NH | — | — | 7.42 |
| Thr6[b] | | | |
| α | CH | 56.2 | 4.30 |
| β | CH | 65.1 | 4.41 |
| γ | CH₃ | 17.27 | 1.10 |
| C=O | C | 170.6 | — |
| NH | — | — | 7.07 |
| Phe7 | | | |
| α | CH | 54.2 | 4.86 |
| β | CH₂ | 40.9 | 3.18/2.72 |
| γ | C | 136.2 | — |
| δ | (CH)₂ | 129.2 | 7.18 |
| ε | (CH)₂ | 128.3 | 7.24 |
| ζ | CH | 127.1 | 7.21 |
| C=N | C | 173.3 | — |
| NH | — | — | 8.46 |
| Cys8 | | | |
| α | CH | 77.12 | 4.94 |
| β | CH₂ | 36.53 | 157/3.44 |
| C=O | C | 170.2 | — | a/b—Residues may be exchanged
n.o.—not observed

TABLE 7

| Residue/Atom | | Natural $\delta_C$/ppm | In vitro $\delta_C$/ppm | Natural $\delta_H$/ppm | In vitro $\delta_H$/ppm |
|---|---|---|---|---|---|
| Ile1/Ile5 | | | | | |
| α | CH | 51.2 | 51.1 | 4.68 | 4.73 |
| β | CH | 38.5 | 38.6 | 1.81 | 1.85 |
| γ₁ | CH₃ | 15.2 | 15.1 | 0.84 | 0.89 |
| γ₂ | CH₂ | 24.7 | 25.2 | 1.41/1.08 | 1.46/1.11 |
| δ | CH₃ | 11.2 | 11.3 | 0.83 | 0.88 |
| C=N | C | 169.4 | 170.0 | — | — |
| NH | — | — | — | 7.42 | 7.39 |
| Thr2/Thr6 | | | | | |
| α | CH | 74.3 | 74.3 | 4.21 | 4.22 |
| β | CH | 80.6 | 80.6 | 4.85 | 4.85 |
| γ | CH₃ | 21.8 | 21.7 | 1.46 | 1.50 |
| C=O | C | 170.7 | 170.8 | — | — |
| Val3/Val7 | | | | | |
| α | CH | 55.4 | 55.1 | 4.78 | 4.81 |
| β | CH | 32.0 | 32.1 | 2.12 | 2.14 |
| γ₁ | CH₃ | 19.3 | 19.3 | 0.97 | 0.98 |
| γ₂ | CH₃ | 16.6 | 17.0 | 0.86 | 0.91 |
| C=N | C | 174.0 | 174.7 | — | — |
| NH | — | — | — | 7.24 | 7.22 |
| Cys4/Cys8 | | | | | |
| α | CH | 77.3 | 78.6 | 5.10 | 5.13 |
| β | CH₂ | 35.9 | 35.6 | 3.64 | 3.68 |
| C=O | C | 170.9 | 170.7 | — | — |

MAIN REFERENCES

Blunt, J. W. et al *Nat Prod Rep* 29, 144-222 (2012).
Mayer, A. M. et al *Comp Biochem Physiol C Toxicol Pharmacol* 153, 191-222 (2011).
Driggers, E. M. et al *Nat Rev Drug Discov* 7, 608-624 (2008).
Cuevas, C. et al *Nat Prod Rep* 26, 322-337 (2009).
McIntosh, J. A. et al. *Nat Prod Rep* 26, 537-559 (2009).
Sivonen, K. et al *Appl Microbiol Biotechnol* 86, 1213-1225 (2010).
Schmidt, E. W. et al. *PNAS. USA* 102, 7315-7320 (2005).
Long, P. F. et al *Chembiochem* 6, 1760-1765 (2005).
Schmidt, E. W., *BMC Biol* 8, 83 (2010).
Houssen, W. E. & Jaspars, M. *Chembiochem* 11, 1803-1815 (2010).
Donia, M. S. et al. *Nat Chem Biol* 2, 729-735 (2006).
Donia, M. S. et al *Nat Chem Biol* 4, 341-343 (2008).
Houssen, W. E. et al. *Chembiochem* 11, 1867-1873 (2010).
Lee, J. et al. *J. Am. Chem. Soc.* 131, 2122-2124 (2009).
McIntosh, J. A. et al. *J. Am. Chem. Soc.* 132, 15499-15501 (2010).
Schechter, I. et al *Biochem. Biophys. Res. Commun.* 27, 157 (1967).
Katoh, T. et al *Chem. Commun.* 47, 9946-9958 (2011).
Trauger, J. W. et al *Nature* 407, 215-218 (2000).
Schneider, A. et al *Archives of Microbiology* 169, 404-410 (1998).
Cane, D. E. et al. *Chemistry & Biology* 6, R319-R325 (1999).
Liu, H. et al *Protein Expr Purif* 63, 102-111 (2009).
Dodson, G. et al *Trends Biochem. Sci.* 23, 347-352 (1998).
Perona, J. J. et al *Protein Sci* 4, 337-360 (1995).
Ziemert, N. et al. *Appl Environ Microbiol* 74, 1791-1797 (2008).
Donia, M. S. et al. *Chem Biol* 18, 508-519 (2011).
Popp, M. W. et al *Angew Chem Int Ed Engl* 50, 5024-5032 (2011).
Ahvazi, B. et al. *Exp Mol Med* 35, 228-242 (2003).
Zhu, X. et al *J. Am. Chem. Soc.* 129, 14597-14604 (2007).
Milne, B. F. et al *Org Biomol Chem* 4, 631-638 (2006).
Liu, H. *Protein Expr Purif* 63, 102-111 (2009).
Studier, F. W. *Protein expression and purification* 41, 207-234 (2005).

Winter, G. *Journal of Applied Crystallography* 43, 186-190 (2009).

Storoni, L. C. et al. *Acta Crystallographica Section D-Biological Crystallography* 60, 432-438 (2004).

McCoy, A. J. et al. *Acta Crystallographica Section D-Biological Crystallography* 61, 458-464 (2005).

Adams, P. D. et al. *Journal of Synchrotron Radiation* 11, 53-55 (2004).

Emsley, P. *Acta Crystallographica Section D-Biological Crystallography* 60, 2126-2132 (2004).

Murshudov, G. N. et al. *Acta Crystallographica Section D-Biological Crystallography* 53, 240-255 (1997).

CCP4. The CCP4 suite: Programs for Protein Crystallography. *Acta Crystallographica Section D* 50, 760-763 (1994).

Cammish, L. E. & Kates, S. A. Fmoc Solid Phase Peptide Synthesis: A Practical Approach. (2000).

```
Sequences
PatG from Prochloron didemni (AAY21156.1)
                                                                    SEQ ID NO: 1
   1 mfsimitidy pftvslnrdi qvtstedyyt lqvtesdpsa wltfattpam dmafdhlkag 61 ttteslvqtl aelggpaare qfaltlqqld ergwlsyavl plaeaipmve saelnlpgnp 121 hwmetgvtls rfayqhpyeg tmvlesplsk frvklldwra sallaqlaqp qtlgtiappp 181 ylgpetayqf lnllwatgfl asdhepvslq lwdfhnllfh srsrlgrhdy pgtdlnvdnw 241 sdfpvvkppm sdrivplprp nlealmsnda tlteaietrk svreydddnp itieqlgell 301 yraarvtkll speerfgklw qqnkpvfeea gvdegefshr pypgggamye leiypvvrlc 361 qglsqgvyhy dplnhqleqi veskddifav sgsplasklg phvllvitar fgrlfrlyrs 421 vayalvlkhv gvlqqnlylv atnmglapca ggagdsdafa qvtgidyvee savgefilgs 481 lasevesdvv egedeiesag vsasevessa tkqkvalhph dlderipgla dlhnqtlgdp 541 qitiviidgd pdytlscfeg aevskvfpyw hepaepitpe dyaafqsird qglkgkekee 601 aleavipdtk drivlndhac hvtstivgqe hspvfgiapn crvinmpqda virgnyddvm 661 splnlaraid lalelganii hcafcrptqt segeeilvqa ikkcqdnnvl ivsptgnnsn 721 eswclpavlp gtlavgaakv dgtpchfsnw ggnntkegil apgeeilgaq pcteepvrlt 781 gtsmaapvmt gisallmslq vqqgkpvdae avrtallkta ipcdpevvee perclrgfvn 841 ipgamkvlfg qpsvtvsfag gqatrtehpg yatvapasip epmaeratpa vqaatatemv 901 iapstepanp atveastafs gnvyalgtig ydfgdearrd tfkermadpy darqmvdyld 961 rnpdearsli wtlnlegdvi yaldpkgpfa tnvyeiflqm lagqlepets adfierlsvp 1021 arrttrtvel fsgevmpvvn vrdprgmygw nvnalvdaal atveyeeade dslrqgltaf 1081 lnrvyhdlhn lgqtsrdral nftvtntfqa astfaqaias grqldtievn kspycrlnsd 1141 cwdvlltfyd pehgrrsrrv frftldvvyv lpvtvgsiks wslpgkgtvs k PatA from Prochloron didemni
                                                                    SEQ ID NO: 2
   1 mnrdilrtls lkgdhnirva ildgpvdiah pcfqgadltv lptlaptaar sdgfmsahgt 61 hvasiifgqp etsvpgiapq crglivpifs ddrrritqld largieravn agahiinisg 121 geltdfgead gwlenayslc rqnnvllvaa agnngcdclh vpaalpavla vgamddhghp 181 ldfsnwgsty eqqgilapge dilgakpggg terlsgtsfa tpivsgvaal llseqvrrge 241 tpdpqkvrql llqsalpcdd dapegarrcl agrlnvsgaf tllkggnmse elatasfpsv 301 eascgcnggl vaaepttnsg smpalsyssf agaspatmea agpldepqpl pspaqpltqm 361 paqplpspaq pltqmpaqpl pfpaqpltqm paqpltqmpa ptqtlsmttn qvtpsqapse 421 lansqfayvl gtlgydfgte arrdtfkqlm ppfdfagnmv panpydarqm vdylgnnise 481 arsliwtvni eltpvyaidp tgpfasstyh alqellsgqi qaedneeyve rvsipgvltn 541 rsvklfsgqv vpvvepqstr glygwkvngl vnaaleavra eggdageari rqtldgflnr 601 iyydlrnlgt tsqdralnfa vtnafqaaqt fsqsvaagme ldsvtveksp fcrldsdcwd 661 iklkffdpen nrrakkiyrf tidvsdlvpv tmgevrswss sy
```

PatD from *Prochloron didemni*

SEQ ID NO: 3

```
  1 mqptalqikp hfhveiiepk qvyllgeqgn haltgqlycq ilpflngeyt reqivekldg
 61 qvpeeyidfv lsrlvekgyl tevapelsle vaafwselgi apsvvaeglk qpvtvttagk
121 giregivanl aaaleeagiq vsdpkapkap kagdstaqlq vvltddylqp elaainkeal
181 erqqpwllvk pvgsilwlgp lfvpgetgcw hclaqrlrgn reveasvlqq kralqerngq
241 nkngaysclp taratlpstl qtglqwaate iakwmvkrhl naiapgtarf ptlagkiftf
301 nqttlelkah plsrrpqcpt cgdqeilqrr gfeplklesr pkhftsdggh rattpeqtvq
361 kyqhligpit gvvtelvris dpanplvhty raghsfgssa gslrglrntl rykssgkgkt
421 dsqsrasglc eaierysgif lgdeprkrat laelgdlaih peqclhfsdr qydnrdalna
481 egsaaayrwi phrfaasqai dwtplwslte qkhkyvptai cyynyllppa drfckadsng
541 naagnsleea ilqgfmelve rdsvalwwyn rlrrpevels sfeepyflql qqfyrsqnre
601 lwvldltadl gipafaglsr rtvgsservs igfgahldpk iailraltev sqvgleldkv
661 pdekldgesk dwmlevtlet hpclapdpsq prktandypk rwsddiytdv macvemakva
721 gletivldqt rpdiglnvvk vmipgmrtfw srygpgrlyd vpvqlgwlke plaeaemnpt
781 nipf
```

TruD from *Prochloron didemni*

SEQ ID NO: 4

```
  1 mqptalqikp hfhveiiepk qvyllgeqgn haltgqlycq ilpflngeyt reqivekldg
 61 qvpeeyidfv lsrlvekgyl tevapelsle vaafwselgi apsvvaeglk qpvtvttagk
121 giregivanl aaaleeagiq vsdprdpkap kagdstaqlq vvltddylqp elaainkeal
181 erqqpwllvk pvgsilwlgp lfvpgetgcw hclaqrlqgn reveasvlqq kralqerngq
241 nkngaysclp taratlpstl qtglqwaate iakwmvkrhl naiapgtarf ptlagkiftf
301 nqttlelkah plsrrpqcpt cgdretlqrr gfeplklesr pkhftsdggh ramtpeqtvq
361 kyqhligpit gvvtelvris dpanplvhty raghsfgsat slrglrnvlr hkssgkgktd
421 sqsrasglce aierysgifq gdeprkratl aelgdlaihp eqclhfsdrq ydnressner
481 atvthdwipq rfdaskandw tpvwslteqt hkylptalcy yrypfppehr fcrsdsngna
541 agntleeail qgfmelverd svclwwynrv srpavdlssf depyflqlqq fyqtqnrdlw
601 vldltadlgi pafvgvsnrk agsseriilg fgahldptva ilraltevnq igleldkvsd
661 eslkndatdw lvnatlaasp ylvadasqpl ktakdyprrw sddiytdvmt cveiakqagl
721 etlvldqtrp diglnvvkvi vpgmrfwsrf gsgrlydvpv klgwreqpla eaqmnptpmp
781 f
```

PatF from *Prochloron didemni*

SEQ ID NO: 5

```
  1 mdlidrlqnn qrkdrrlqfv rthqeafdvk ptfplplfee aileiegscs vesscqvegd
 61 rlqggryevc nnqgttwpes lthafklldk idsqlgvrin rdsfdrfaaa hvnsrkiinn
121 tigvhlgskl edssvmlyih ikpeedteel artalvldgg rysdeltrvl lrdtmvigfe
181 lffdgrsrvd lgpcapgksg tlkmkgkhle qytqknlsrk vnsifregyl fgaffsktrv
241 epilffyhsi ikdlpkyftf nslgdkiynf cqsqgcitdv aiavtetele ksrlenfcfy
301 ydqwdeckps sdydterhlh
```

The invention claimed is:

1. A method of producing a cyclic peptide comprising:
   (i) providing a linear peptide substrate comprising a target peptide having 6 to 11 residues and a C terminal cyclisation signal consisting of AND, AYE, SYD, AFD, FAG or AYR; and,
   (ii) treating said linear peptide substrate with an isolated cyanobacterial macrocyclase to produce a cyclic peptide, wherein the residue in the target peptide adjacent the cyclisation signal is pseudoproline, a thiazoline, a thiazole, an oxazoline, or an oxazole.

2. The method according to claim 1, wherein the cyanobacterial macrocyclase comprises an amino acid sequence having at least 60% sequence identity to the amino sequence of residues 492-851 of PatG (SEQ ID NO:1) or an amino sequence selected from the group consisting of SEQ ID NOs: 7 to 19.

3. The method according to claim 1, wherein the cyanobacterial macrocyclase comprises one or more residues for substitution that includes R589, K594, K598 or H746 of PatG (SEQ ID NO: 1), and the linear peptide substrate comprises a modified cyclisation signal.

4. The method according to claim 1, wherein the Cyanobacterial macrocyclase comprises a K598D substitution at the residue equivalent to K598 of PatG and the linear peptide substrate comprises the cyclisation signal AYR.

5. The method according to claim 1, wherein the linear peptide substrate is treated with the cyanobacterial macrocyclase in 500 mM NaCl and/or pH 9.

6. The method according to claim 1, wherein the linear peptide substrate is provided by a method comprising;
   (i) providing a pro-peptide comprising a peptide substrate linked to a pro-sequence by a protease recognition site; and,
   (ii) treating said pro-peptide with an isolated protease to produce the linear peptide substrate.

7. The method according to claim 6, wherein the protease recognition site is a heterologous protease recognition site and the protease is a heterologous protease.

8. The method according to claim 7, wherein the heterologous protease recognition site is a K residue and the heterologous protease is trypsin; the heterologous protease site is Y and the protease is chymotrypsin; or the heterologous protease site is ENLYFQ(G/S) (SEQ ID NO: 57) and the protease is Tobacco Etch Virus (TEV) protease.

9. The method according to claim 1, wherein the linear peptide substrate is provided by a method comprising;
   (iii) providing a pre-pro-peptide comprising one or more heterocyclisable amino acids; and
   (iv) treating said pre-pro-peptide with a PatD or TruD heterocyclase to convert the heterocyclisable amino acids into heterocyclic residues,
   thereby producing the linear peptide substrate.

10. The method according to claim 9, wherein the PatD heterocyclase comprises an amino acid sequence having at least 60% sequence identity to PatD (SEQ ID NO:3) or TruD (SEQ ID NO:4).

11. The method according to claim 9, wherein the method comprises treating the linear peptide substrate or the cyclic peptide to oxidise the heterocyclic residues.

12. The method according to claim 1, wherein the cyclic peptide is treated with a cyanobacterial prenylase to produce a prenylated or geranylated cyclic peptide.

13. The method according to claim 1, wherein the cyclic peptide is labelled with a detectable label.

14. The method according to claim 1, wherein the linear peptide substrate is immobilised on a bead.

15. The method according to claim 14, wherein a reference copy of said linear peptide substrate is additionally immobilised to said bead, said reference copy lacking a cyclisation signal.

16. The method according to claim 15, wherein the cyclic peptide is released from the bead following said treatment with the cyanobacterial macrocyclase and the reference copy remains immobilised to the bead.

17. The method according to claim 16, further comprising isolating and screening said cyclic peptide to identify a biological activity.

18. The method according to claim 17, further comprising identify the bead which released the cyclic peptide and sequencing the reference copy immobilised on said bead.

19. The method according to claim 1, wherein the linear peptide substrate is provided by a method comprising;
   (i) providing a pro-peptide comprising a peptide substrate linked to a pro-sequence by a heterologous protease recognition site; and,
   (ii) treating said pro-peptide with an isolated heterologous protease to produce the linear peptide substrate,
   wherein the heterologous protease recognition site is a K residue and the heterologous protease is trypsin; or the heterologous protease site is Y and the protease is chymotrypsin.

20. The method according to claim 6, wherein the pro-peptide is provided by a method comprising;
   (i) providing a pre-pro-peptide comprising one or more heterocyclisable amino acids; and
   (ii) treating said pre-pro-peptide with a PatD or TruD heterocyclase to convert the heterocyclisable amino acids into heterocyclic residues,
   thereby producing the pro-peptide.

21. The method according to claim 6, wherein the method comprises treating the pro-peptide to oxidise the heterocyclic residues.

* * * * *

UNITED STATES PATENT AND TRADEMARK OFFICE
CERTIFICATE OF CORRECTION

PATENT NO. : 10,494,657 B2
APPLICATION NO. : 15/683266
DATED : December 3, 2019
INVENTOR(S) : Wael Houssen Ibrahim et al.

Page 1 of 1

It is certified that error appears in the above-identified patent and that said Letters Patent is hereby corrected as shown below:

In the Claims

Claim 1, Column 127, Line 5, replace "AND" with --AYD--.

Signed and Sealed this
Second Day of June, 2020

Andrei Iancu
*Director of the United States Patent and Trademark Office*